United States Patent [19]

Wolf

[11] Patent Number: 4,931,081
[45] Date of Patent: Jun. 5, 1990

[54] HERBICIDAL DIAZOLES SULFONAMIDES

[75] Inventor: Anthony D. Wolf, Elkton, Md.

[73] Assignee: E. I. Du Pont de Nemours and Company, Wilmington, Del.

[21] Appl. No.: 486,092

[22] Filed: Apr. 25, 1983

Related U.S. Application Data

[63] Continuation-in-part of Ser. No. 384,043, Jun. 1, 1982, abandoned.

[51] Int. Cl.$^5$ .................... A01N 43/36; A01N 43/40; C07D 239/42; C07D 239/47
[52] U.S. Cl. .......................................... 71/92; 71/77; 71/93; 544/216; 544/217; 544/218; 544/219; 544/298; 544/320; 544/321; 544/331; 544/212; 544/278; 548/262.6
[58] Field of Search ............... 544/256, 298, 320, 321, 544/331; 71/92

[56] References Cited

U.S. PATENT DOCUMENTS

| | | | |
|---|---|---|---|
| 4,368,067 | 1/1983 | Budzinski | 71/92 |
| 4,398,939 | 8/1983 | Levitt | 71/90 |
| 4,416,683 | 11/1983 | Burow | 71/92 |

FOREIGN PATENT DOCUMENTS 30142 6/1981 European Pat. Off. .
64804 11/1982 European Pat. Off. .

Primary Examiner—Cecilia Shen

[57] ABSTRACT

This invention relates to herbicidal heterocyclic aminocarbonyl diazole sulfonamides compounds, compositions thereof and a method for their use to control the growth of undesired vegetation.

82 Claims, No Drawings

HERBICIDAL DIAZOLES SULFONAMIDES

RELATED APPLICATION

This application is a continuation-in-part of my co-pending application U.S. Ser. No. 384,043, filed June 1, 1982 now abandoned.

BACKGROUND OF THE INVENTION

This invention relates to novel diazoles, to herbicidal compositions containing them and to the method of using them for controlling the growth of undesired vegetation.

The control of undesired vegetation is desired in many instances. In the most common situation, it is desired to selectively control the growth of weeds in useful crops such as cotton, rice, corn, wheat and soybeans, to name a few. Unchecked weed growth in such useful crops can cause significant losses, reducing profit to the farmer and increasing costs to the consumer. In other situations, herbicides are desired which will control all plant growth. Examples of areas in which complete control of all vegetation is desired are areas around fuel storage tanks, ammunition depots and industrial storage areas. There are many products commercially available for these purposes, but the search continues for products which are more effective, less costly and environmentally safe.

U.S. Pat. No. 4,127,405, issued to Levitt on Nov. 28, 1978, discloses herbicidal sulfonamides of the formula

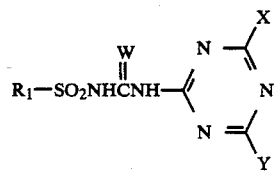

where
$R_1$ is selected from

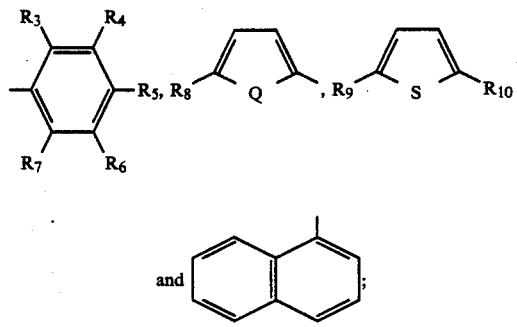

and where W and Q are independently O or S.

U.S. Pat. No. 4,169,719, issued to Levitt on Oct. 2, 1979, discloses pyrimidine compounds corresponding to the triazines disclosed in the '405 patent.

European Patent Application No. 81301874.4, published on Nov. 4, 1981, discloses herbicidal pyrrole sulfonamides of the formulas

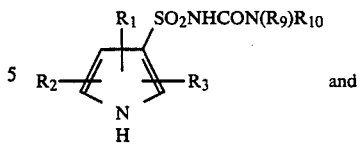

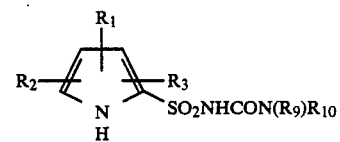

where $R_{10}$ is selected from

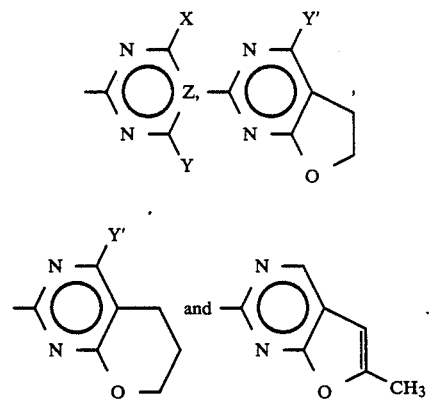

European Patent Application No. 80304287.8, published on June 10, 1981, discloses herbicidal compounds of the formulas

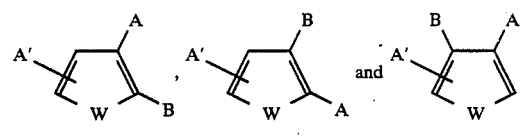

where
W is O or S;
B is

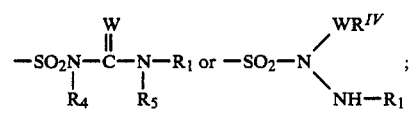

$R_1$ is

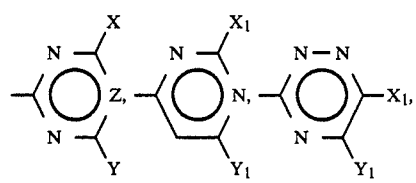

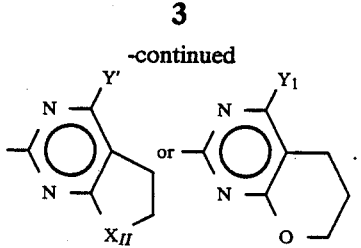

European Patent Application No. 81302461.9, published on Dec. 9, 1981, discloses herbicidal thiophenesulfonamides of the formula

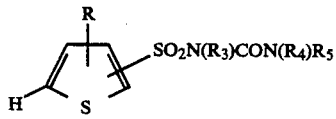

where
R₅ is selected from

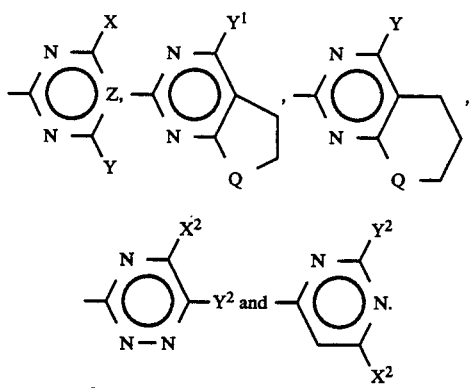

Nowhere in the art is there any indication that N-[(heterocyclic)aminocarbonyl]diazole sulfonamides could be prepared or that they would possess herbicidal utility.

SUMMARY OF THE INVENTION

It has now been found that the compounds of Formula I have utility as plant growth regulants and/or herbicides.

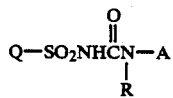

where
R is H or CH$_3$;
Q is

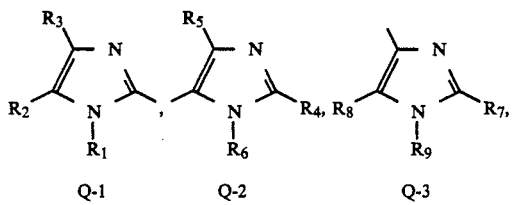

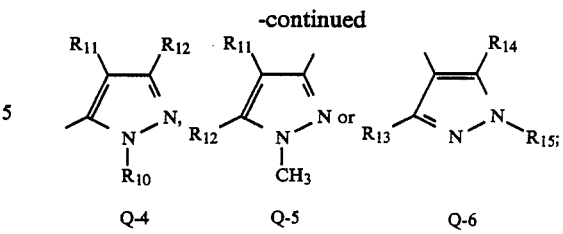

R$_1$ is H, C$_1$–C$_8$ alkyl, C$_3$–C$_6$ alkenyl, C$_5$–C$_6$ cycloalkyl, C$_5$–C$_6$ cycloalkenyl, C$_3$–C$_6$ alkynyl, C$_4$–C$_7$ cycloalkylalkyl, (R$_{17}$CH)$_n$C(O)R$_{16}$, (R$_{17}$CH)$_n$CO$_2$R$_{18}$, (R$_{17}$CH)$_n$COSR$_{19}$, (R$_{17}$CH)$_n$CONR$_{20}$R$_{21}$, (R$_{17}$CH)$_n$SO$_2$NR$_{20}$R$_{21}$, (R$_{17}$CH)$_n$SO$_2$R$_{22}$,

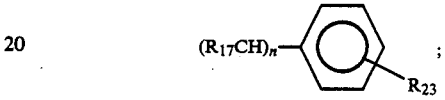

or C$_1$–C$_6$ alkyl substituted either with
(a) 1–3 atoms of F, Br or Cl; or
(b) OR$_{16}$;
provided that,
(1) the total number of carbon atoms in R$_1$ is less than or equal to 8; and
(2) if R$_1$ is other than C$_1$–C$_3$ alkyl, then R$_3$ must be H;
R$_2$, R$_3$ and R$_4$ are independently H or CH$_3$;
R$_5$ is H, C$_1$–C$_4$ alkyl, —OR$_6$, NO$_2$, F, Cl, Br, CO$_2$R$_{24}$, S(O)$_m$R$_{25}$ or SO$_2$NR$_{20}$R$_{21}$;
R$_6$ is H, C$_1$–C$_4$ alkyl, C$_3$–C$_4$ alkenyl C$_3$–C$_4$ alkynyl, CO$_2$R$_{18}$, SO$_2$NR$_{20}$R$_{21}$, SO$_2$R$_{22}$ or C$_1$–C$_4$ alkyl substituted with (a) 1–3 atoms of F, Cl or Br; or (b) OCH$_3$;
provided that,
(1) when R$_5$ is other than H, CH$_3$, OCH$_3$ or NO$_2$, then R$_6$ is H or CH$_3$; and
(2) when R$_6$ is CO$_2$R$_{18}$, SO$_2$NR$_{20}$R$_{21}$ or SO$_2$R$_{22}$, then R$_5$ is H, CH$_3$, OCH$_3$ or NO$_2$;
R$_7$ is H or CH$_3$;
R$_8$ is H, C$_1$–C$_4$ alkyl, —OR$_{16}$, NO$_2$, F, Cl, Br, CO$_2$R$_{24}$, S(O)$_m$R$_{25}$ or SO$_2$NR$_{20}$R$_{21}$;
R$_9$ is CH$_3$ or C$_2$H$_5$;
R$_{10}$ is H, C$_1$–C$_4$ alkyl, C$_3$–C$_4$ alkenyl, C$_3$–C$_4$ alkynyl, CO$_2$R$_{24}$, SO$_2$NR$_{20}$R$_{21}$ or SO$_2$R$_{22}$;
R$_{11}$ is H, C$_1$–C$_3$ alkyl, F, Cl, Br, NO$_2$, —OR$_{16}$, CO$_2$R$_{24}$, S(O)$_m$R$_{25}$ or SO$_2$NR$_{20}$R$_{21}$; provided that, when R$_{10}$ is other than C$_1$–C$_3$ alkyl, then R$_{11}$ is H, Cl, OCH$_3$, NO$_2$ or CH$_3$;
R$_{12}$ is H or CH$_3$;
R$_{13}$ and R$_{14}$ are independently H, C$_1$–C$_3$ alkyl —OR$_{16}$, F, Cl, Br, NO$_2$, CO$_2$R$_{24}$, S(O)$_m$R$_{25}$ or SO$_2$NR$_{20}$R$_{21}$; provided that, when either of R$_{13}$ or R$_{14}$ is CO$_2$R$_{24}$, S(O)$_m$R$_{25}$ or SO$_2$NR$_{20}$R$_{21}$, then the other is H, Cl, CH$_3$, OCH$_3$ or NO$_2$;
R$_{15}$ is H or CH$_3$;
R$_{16}$ is C$_1$–C$_3$ alkyl;
R$_{17}$ is H or CH$_3$;
R$_{18}$ is C$_1$–C$_4$ alkyl, C$_3$–C$_4$ alkenyl, C$_3$–C$_4$ alkynyl, CH$_2$CH$_2$Cl or CH$_2$CH$_2$OCH$_3$;
R$_{19}$ is C$_1$–C$_4$ alkyl, C$_3$–C$_4$ alkenyl, C$_3$–C$_4$ alkynyl or CH$_2$CH$_2$OCH$_3$;
R$_{20}$ and R$_{21}$ are independently CH$_3$ or C$_2$H$_5$;
R$_{22}$ is C$_1$–C$_3$ alkyl or CF$_3$;
R$_{23}$ is H, Cl, Br, CH$_3$, F, CF$_3$, OCH$_3$ or NO$_2$;

$R_{24}$ is $C_1$-$C_3$ alkyl or allyl;
$R_{25}$ is $C_1$-$C_3$ alkyl;
m is 0, 1 or 2;
n is 0 or 1;
A is

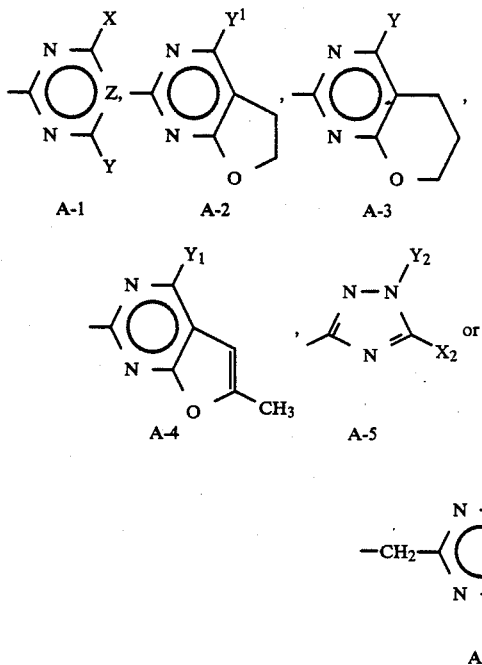

X is $CH_3$, $OCH_3$, Cl, F, $OCF_2H$ or $SCF_2H$;
Y is $CH_3$, $C_2H_5$, $OCH_3$, $OC_2H_5$, $CH_2OCH_3$, $CH(OCH_3)_2$, $OCH_2CF_3$, $OCF_3$, $NH_2$, $NHCH_3$, $N(CH_3)_2$ or $GCF_2T$ where G is O or S and T is H, CHClF, CHBrF, $CF_2H$ or $CHFCF_3$;
Z is CH or N;
$Y_1$ is H, Cl, $CH_3$, $OCH_3$ or $OCF_2H$;
$X_2$ is $OCH_3$, $CH_3$, $CH_2CH_3$, $OCH_2CH_3$, $SCH_3$ or $SCH_2CH_3$;
$Y_2$ is $CH_3$, $CH_2CH_3$ or $CH_2CF_3$;
$X_3$ is $OCH_3$ or $CH_3$;
provided that,
when X is Cl or F, then Z is CH and Y is $OCH_3$, $NH_2$, $NHCH_3$ or $N(CH_3)_2$;
and agriculturally suitable salts thereof.

This invention therefore relates to compounds of Formula I, to herbicidal compositions containing the compounds and to methods of using the compounds to control the growth of undesired vegetation.

Certain groups of compounds are preferred because of their high herbicidal and/or plant growth regulant activity and/or because of the ease with which they may be prepared. These preferred groups are as follows:

1. Compounds of Formula I where Q is Q-1 and R is H.
  1a. Compounds of Preferred 1 where A is A-1, and Z is CH.
  1b. Compounds of Preferred 1a where X is $CH_3$, Cl, $OCH_3$ or $OCF_2H$ and Y is $CH_3$, $OCH_3$ or $OCF_2H$.
  1c. Compounds of Preferred 1b where $R_1$ is H or $C_1$-$C_4$ alkyl, and $R_3$ is H.
2. Compounds of Formula I where Q is Q-2, and R is H.
  2a. Compounds of Preferred 2 where A is A-1, Z is CH and $R_4$ is H.
  2b. Compounds of Preferred 2a where X is $CH_3$, Cl, $OCH_3$ or $OCF_2H$ and Y is $CH_3$, $OCH_3$ or $OCF_2H$.
  2c. Compounds of Preferred 2b where $R_5$ is H, $CH_3$, $OCH_3$, Cl, $NO_2$, $CO_2R_{24}$ or $SO_2NR_{20}R_{21}$ and $R_6$ is H or $C_1$-$C_4$ alkyl.
3. Compounds of Formula I where Q is Q-3 and R is H.
  3a. Compounds of Preferred 3 where A is A-1, Z is CH and $R_7$ is H.
  3b. Compounds of Preferred 3a where X is $CH_3$, Cl, $OCH_3$ or $OCF_2H$ and Y is $CH_3$, $OCH_3$ or $OCF_2H$.
  3c. Compounds of Preferred 3b where $R_8$ is Br, $C_1$-$C_4$ alkyl, $OCH_3$, Cl, $NO_2$, $CO_2R_{24}$, $S(O)_mR_{25}$ or $SO_2NR_{20}R_{21}$.
4. Compounds of Formula I where Q is Q-4 and R is H.
  4a. Compounds of Preferred 4 where A is A-1 and Z is CH.
  4b. Compounds of Preferred 4a where X is $CH_3$, Cl, $OCH_3$ or $OCF_2H$ and Y is $CH_3$, $OCH_3$ or $OCF_2H$.
  4c. Compounds of Preferred 4b where $R_{10}$ is H, $C_1$-$C_3$ alkyl, $CO_2CH_3$, $SO_2CH_3$ or $SO_2N(CH_3)_2$ and $R_{11}$ is H, $CH_3$, $OCH_3$, Cl, Br, $NO_2$, $CO_2CH_3$, $SO_2CH_3$ or $SO_2N(CH_3)_2$.
5. Compounds of Formula I where Q is Q-5 and R is H.
  5a. Compounds of Preferred 5 where A is A-1 and Z is CH.
  5b. Compounds of Preferred 5a where X is $CH_3$, Cl, $OCH_3$ or $OCF_2H$ and Y is $CH_3$, $OCH_3$ or $OCF_2H$.
  5c. Compounds of Preferred 5b where $R_{11}$ is H, $CH_3$, $OCH_3$, Cl, Br, $NO_2$, $CO_2CH_3$, $SO_2CH_3$ or $SO_2N(CH_3)_2$.
6. Compounds of Formula I where Q is Q-6 and R is H.
  6a. Compounds of Preferred 6 where A is A-1 and Z is CH.
  6b. Compounds of Preferred 6a where X is $CH_3$, Cl, $OCH_3$ or $OCF_2H$ and Y is $CH_3$, $OCH_3$ or $OCF_2H$.
  6c. Compounds of Preferred 6b where $R_{13}$ and $R_{14}$ are independently H, $CH_3$, $OCH_3$, Cl, Br, $NO_2$, $CO_2CH_3$, $SO_2CH_3$ or $SO_2N(CH_3)_2$.

The following compounds are specifically preferred because of their high herbicidal and/or plant growth regulant activity and/or because of the ease with which they may be synthesized.

N-[(4,6-dimethylpyrimidin-2-yl)aminocarbonyl]-1-(1-methylethyl)-1H-imidazole-2-sulfonamide, m.p. 185°–186° C.(d);

N-[(4-methoxy-6-methylpyrimidin-2-yl)aminocarbonyl]-1-(1-methylethyl)-1H-imidazole-2-sulfonamide, m.p. 157°–158° C.(d);

N-[(4,6-dimethoxypyrimidin-2-yl)aminocarbonyl]-1-(1-methylethyl)-1H-imidazole-2-sulfonamide, m.p. 166°–167° C.;

N-[(4,6-dimethylpyrimidin-2-yl)aminocarbonyl]-1-ethyl-1H-imidazole-2-sulfonamide, m.p. 196°–197° C.;

N-[(4-methoxy-6-methylpyrimidin-2-yl)aminocarbonyl]-1-ethyl-1H-imidazole-2-sulfonamide, m.p. 178°–179° C.(d);

N-[(4,6-dimethoxypyrimidin-2-yl)aminocarbonyl]-1-ethyl-1H-imidazole-2-sulfonamide, m.p. 186°–187° C.; and N-[(4,6-dimethoxypyrimidin-2-yl)aminocarbonyl]-5-bromo-1-methyl-1H-imidazole-4-sulfonamide, m.p. 205°–206° C.

DETAILED DESCRIPTION OF THE INVENTION

Synthesis a. Compounds of the Invention

The diazolesulfonylureas of this invention can be prepared by a number of methods. These methods, and the publications or sources describing them, are as follows:

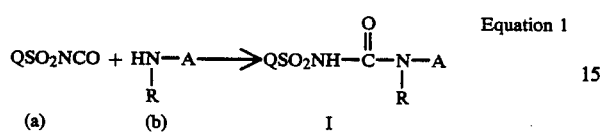

Equation 1

As shown in Equation 1, an appropriately substituted sulfonyl isocyanate (a) is reacted with an appropriate aminoheterocycle (b). The reaction is best carried out in an inert aprotic solvent, such as methylene chloride, tetrahydrofuran, acetonitrile, ether or chloroform, at temperatures ranging from about −20° to 50° C. In some cases, the desired product may crystallize from the reaction medium and may be filtered. Reaction products which are soluble in the reaction medium may be isolated by evaporation of the solvent, trituration of the residue with solvents such as diethyl ether, ethyl acetate, 1-chlorobutane or hexane. Chromatography (e.g., silica gel) may also be necessary for purification. This process is described in U.S. Pat. Nos. 4,127,405, 4,257,802 and 4,221,585.

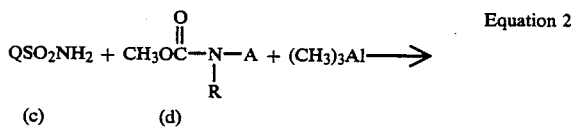

Equation 2

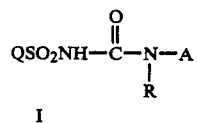

As shown in Equation 2, compounds of Formula (I) can also be prepared by reacting a sulfonamide (e) with an appropriate methyl carbamate (d) in the presence of an equimolar amount of trimethylaluminum. The reaction is best run in an inert aprotic solvent such as methylene chloride at about 25° to 40° C. for 10 to 96 hours under a nitrogen atmosphere. The product can be isolated by addition of an aqueous acetic acid solution followed by extraction of the product into methylene chloride, or by filtration of a product of low solubility. The product can be purified by trituration with solvents such as 1-chlorobutane, ethyl acetate or ethyl ether or by column chromatography on silica gel.

Equation 3

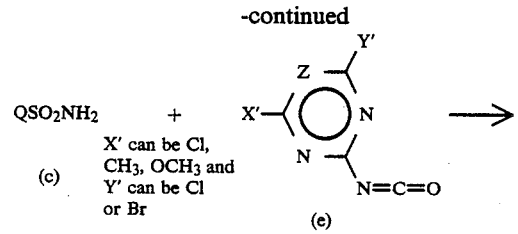

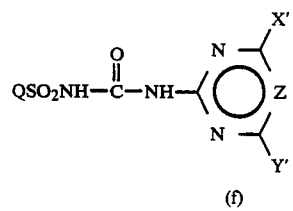

Equation 4

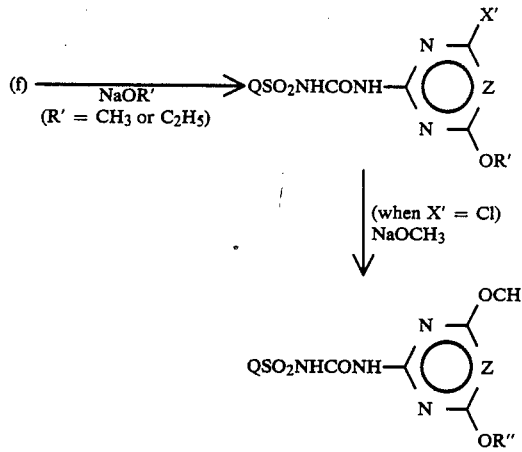

Examples of other methods for preparing compounds of this invention are illustrated in Equations 3 and 4 and described in European Patent Application No. 80304285.2, published June 10, 1981. The first step of this two-step process (Equation 3) involves reaction of a diazole sulfonamide and a heterocyclic isocyanate to yield an N-(haloheterocyclicaminocarbonyl)aromatic sulfonamide (f). This reaction is best run in an inert organic solvent such as acetonitrile, tetrahydrofuran, toluene, acetone or butanone, preferably at a temperature of about 25° to 110° C. The product can then be further reacted with selected nucleophiles, for example alkoxide —OR′, (Equation 4) to yield herbicidal N-(substituted heterocyclicaminocarbonyl)aromatic sulfonamides of this invention.

Equation 5

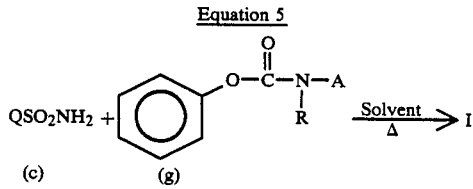

European Patent Application 81810282.4, published January 27, 1982

Equation 6

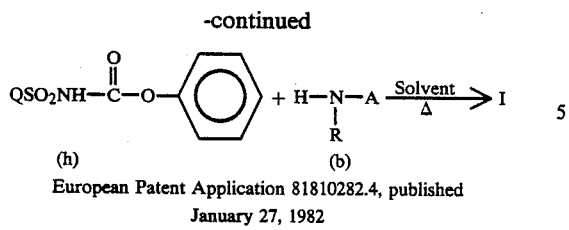

(h)                                    (b)

European Patent Application 81810282.4, published January 27, 1982

Equations 5 and 6 illustrate two additional methods for preparing the compounds of this invention. As shown in Equation 5, a diazole sulfonamide (e) is reacted with an N-heterocyclic carbamate (g) in the presence of a base. Alternatively, in Equation 6, an N-phenylsulfonylcarbamate (h) is reacted with an amine (b). Both of these processes are described in European Patent Application No. 81810281.6 (Publication No. 44,807, Jan. 27, 1982). Both reactions are best carried out in aprotic, inert organic solvents such as methylene chloride, tetrahydrofuran, acetonitrile, dioxane and toluene, at temperatures between $-20°$ and $120°$ C. Suitable bases for use in the process of Equation 5 are organic bases such as amines and inorganic bases such as hydrides, hydroxides, carbonates and bicarbonates.

Compounds of Formula I in which Q is Q-1, $R_1$ is as defined above except that n must be 1, and R, $R_2$, $R_3$ and A are as defined previously, are best prepared by the procedures outlined in Equations 2, 5 or 6.

Compounds of Formula I in which Q is Q-2, Q-3, Q-4, Q-5 or Q-6, m is 0 or 2 and all other substituents are as previously defined are best prepared by the procedures of Equations 2, 5 or 6. Many of these compounds may also be prepared by the procedure of Equation 1. When m is 1, the compounds can be prepared by oxidation of the corresponding sulfide (m=0) with m-chloroperbenzoic acid as described in European Patent Application No. 81300956.0, published Sept. 16, 1981.

Compounds of this invention represented below by Formula 4 (Q of Formula I is Q-1, $R_1$ is $(R_{17}CH)_nCOR_{16}$, $(R_{17}CH)_nCO_2R_{18}$, $(R_{17}CH)_nCOSR_{19}$, $(R_{17}CH)_nCONR_{20}R_{21}$, $(R_{17}CH)_nSO_2NR_{20}R_{21}$, or $(R_{17}CH)SO_2R_{22}$, and R, $R_2$, $R_3$ and A are as previously defined) may be prepared by the procedures outlined in Equations 7 or 8.

Equation 7

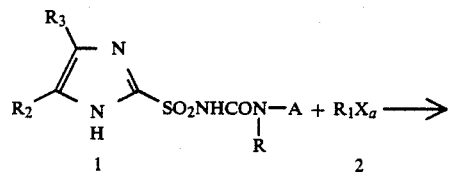

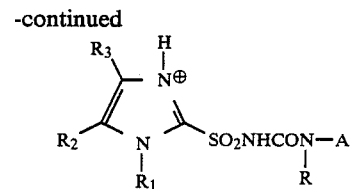

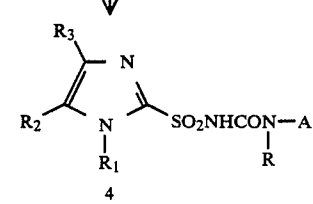

Equation 8

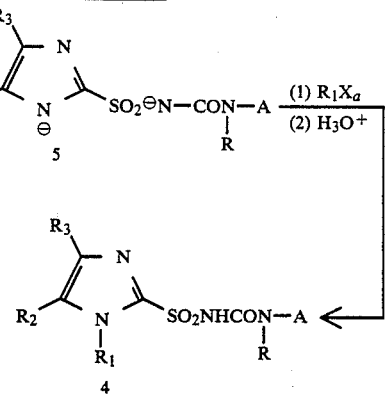

In both Equations 7 and 8, $X_a$ can be Cl, Br or I and, when n is 0 and $R_1$ is $C(O)R_{16}$, then $X_a$ can also be $-OCOR_{16}$, and when n is 0 and $R_1$ is $-SO_2R_{22}$, then $X_a$ can also be $-OSO_2R_{22}$.

In Equation 7, a sulfonylurea 1 is reacted with an appropriate alkylating or acylating agent, $R_1X_a$, in a suitable solvent such as $CH_2Cl_2$, xylene or tetrahydrofuran, for periods of 1 to 50 days at temperatures from ambient to the reflux temperature of the solvent. The salt 3 is neutralized to the product 4 by pouring the reaction mixture into water and reacting it with an appropriate amount of a base such as $NaHCO_3$ or $Na_2CO_3$. The product is isolated by extraction and then purified by the usual techniques of crystallization or chromatography.

In Equation 8, the sulfonylurea 1 is converted to its dianion 5 with two equivalents of a strong base such as NaH, sec-butyllithium or potassium tert-butoxide, in a suitable solvent such as tetrahydrofuran. The dianion is treated with an equivalent of an alkylating or acylating agent, $R_1X_a$, to yield the salt of 4. The reaction mixture is poured into water and acidified to pH 2–3 with a mineral acid such as aqueous hydrochloric acid. The product 4 is isolated and purified as described for Equation 7.

b. Intermediate Compounds

Heterocyclic amines of formula (b) are known in the art. For procedures of synthesis see U.S. Pat. No.

4,127,405, U.S. Pat. No. 4,221,585, EP No. 0015683 and European Patent Application No. 81303837.9, published Mar. 3, 1982 and South African Patent Application No. 82/5045.

Heterocyclic carbamates of Formula (d) are prepared by procedures taught in U.S. Ser. No. 337,934, filed Jan. 7, 1982.

Sulfonyl isocyanates may be prepared by procedures taught in U.S. Pat. No. 4,127,405 and European Patent Application No. 80301848.0, published Jan. 7, 1981.

Sulfonamides of Formula (c) in which Q is Q-1, $R_2$ and $R_3$ are as previously defined, and $R_1$ is H, $C_1$-$C_8$ alkyl; $C_4$-$C_7$ cycloalkylalkyl, $C_1$-$C_6$ alkyl substituted with 1-3 atoms of F, Br or Cl or with one —$OR_{16}$; or

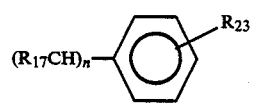

are prepared by procedures known in the art and also outlined in Equations 9, 10 and 10a.

Equation 9

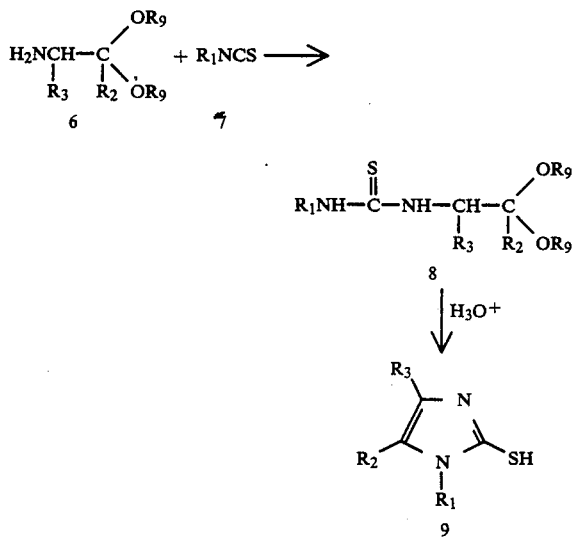

Equation 10a

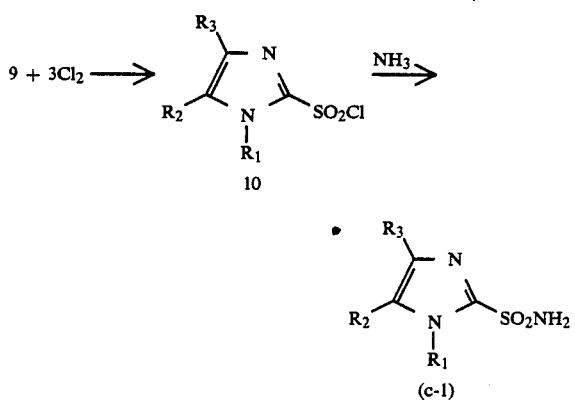

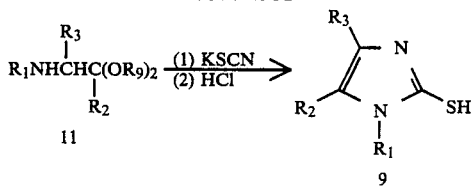

Mercapto imidazoles 9 are known in the art. For representative procedures see R. G. Jones, E. C. Kornfeld, K. C. McLaughlin and R. C. Anderson, *J. Am. Chem. Soc.*, 71 4000 (1949) and references cited therein.

The procedure for converting mercapto imidazoles 9 to sulfonamides (c-1), shown in Equation 10, is known in the art. Details can be found in R. O. Roblin, Jr. and James W. Clapp, *J. Am. Chem. Soc.*, 72 4890 (1950). Improved yields of sulfonamides are sometimes obtained when stoichiometric quantities of $Cl_2$ are used in this procedure, rather than an excess as described.

Compounds of Formula (c) in which Q is Q-1, $R_2$ and $R_3$ are as previously defined, and $R_1$ is $C_3$-$C_6$ alkenyl, $C_3$-$C_6$ alkynyl, $COR_{16}$, $CO_2R_{18}$, $COSR_{19}$, $CONR_{20}R_{21}$, $SO_2NR_{20}R_{21}$ or $SO_2R_{22}$ are best prepared by the procedure of Equation 11.

Equation 11

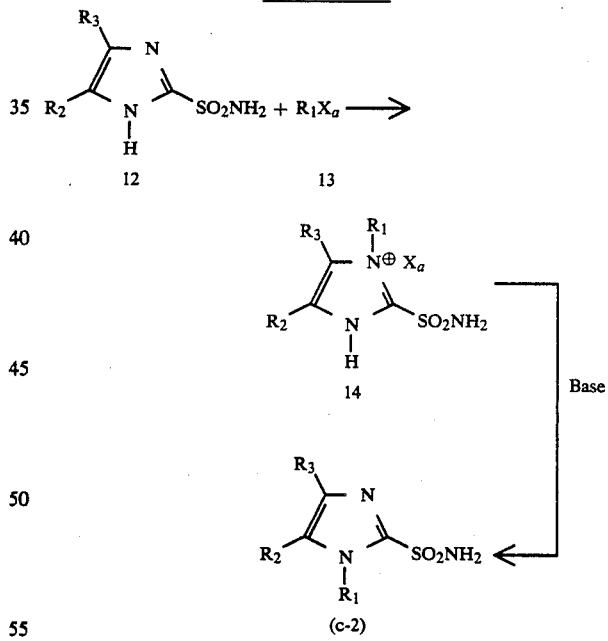

$X_a$ is Cl or Br;
when $R_1$ is $C_3$-$C_6$ alkenyl or $C_3$-$C_6$ alkynyl, $X_a$ can also be I;
when $R_1$ is $COR_{16}$, $X_a$ can also be $OCOR_{16}$, and
when $R_1$ is $SO_2R_{22}$, $X_a$ can also be $OSO_2R_{22}$.

This method is known to those skilled in the art and is carried out in a manner analogous to the process outlined in Equation 7.

Many of the sulfonamides of Formula (c) are known in the art or can be prepared from known imidazole intermediates by chemical transformations known to those skilled in the art. General literature references describing the chemistry of imidazoles include:

Elderfield, Chemistry of Heterocyclic Compounds, Vol. V, p. 194–297, 1957, John Wiley and Sons, Inc., New York.

T. Kauffman and R. Werthwein, Angew Chem., Int. Ed. Engl. 10 20–33 (1971).

M. R. Grimmett, Adv. Heterocycl. Chem. 12. 104–184 (1970).

The preparation of substituted nitro imidazolesulfonamides of Formulas (c-3) and (c-4) (Q is Q-2 or Q-3 and $R_5$ and $R_8$ are $-NO_2$) is shown in Equation 12.

_Equation 12_

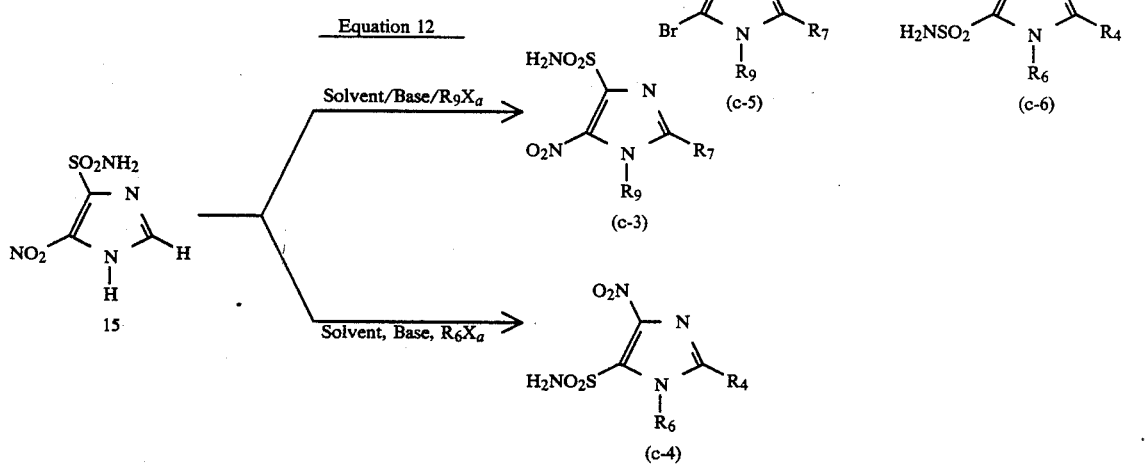

where
$R_4$ and $R_7$ are H;
$R_6$ and $R_9$ are H, $CH_3$ or $CH_2C_6H_5$;
$X_a$ is Cl, Br or I; and
$R_9$ is $CH_3$ or $CH_3CH_2$.

This process is as described in B. S. Huang, M. J. Lauzon and J. C. Parham, J. Het. Chem. 16, 811 (1979). Using similar procedures compounds of structure (c-3) in which $R_9$ is $CH_3CH_2$, and $R_7$ is H or $CH_3$ can be prepared. Also, intermediates of structure (c-4) in which $R_4$ is $CH_3$ or H and $R_6$ is $C_2$–$C_4$ alkyl; $C_3$–$C_4$ alkenyl; $C_1$–$C_4$ alkyl substituted with 1–3 atoms of F, Cl, Br or with $OCH_3$; $CO_2R_{18}$; $SO_2NR_{19}R_{20}$; or $SO_2R_{21}$ can be prepared.

The preparation of bromo or chloro imidazole sulfonamides of formula (c-5) and (c-6) (Q is Q-2 or Q-3 and $R_5$ and $R_8$ are Br or Cl) is outlined in Equation 12a.

The preparation of 4(5)bromo imidazole 16 is described by I. E. Balaban and F. L. Pyman, _J. Chem. Soc._, 121 947 (1922). The preparation of the 4(5)bromo-5(4)sulfonamide imidazole 17 is taught in L. L. Bennett and H. T. Baker, _J. Am. Chem. Soc._, 79, 2188 (1956).

The preparation of additional intermediates for use in preparing the compounds of this invention from readily available imidazole intermediates is outlined in Scheme 1.

_Scheme 1_

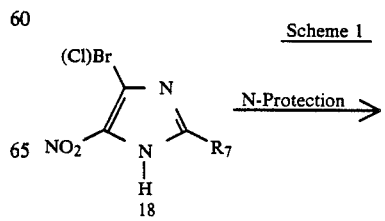

-continued
Scheme 1

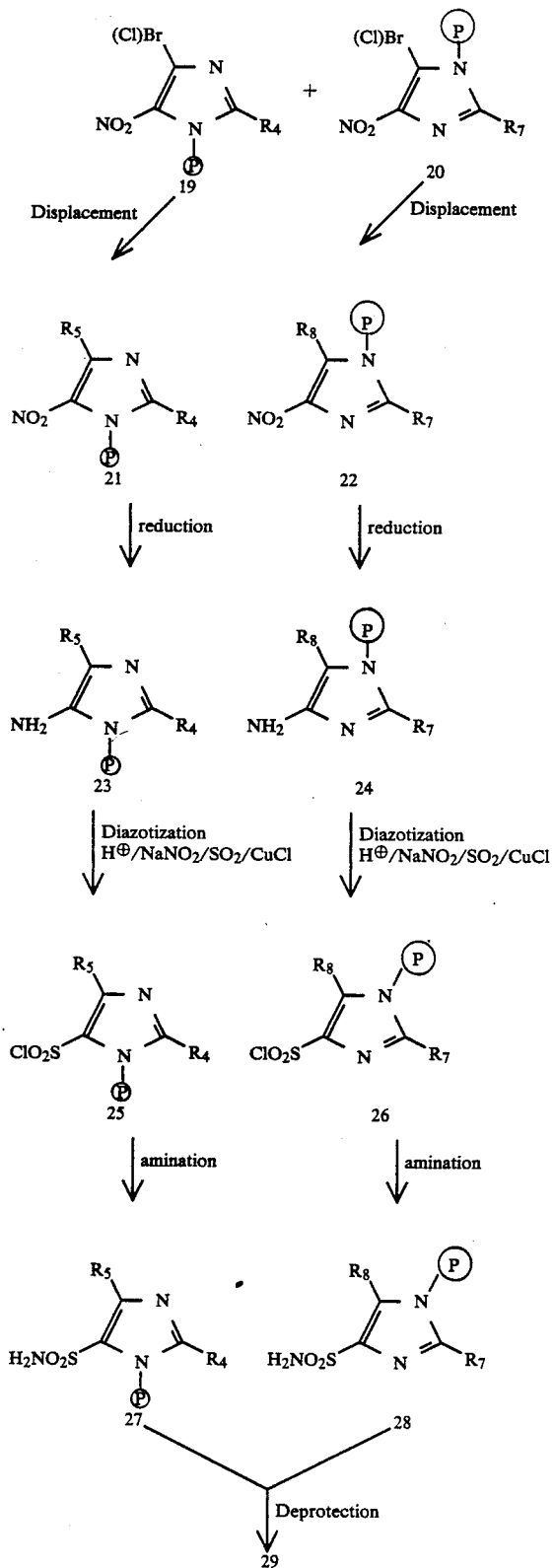

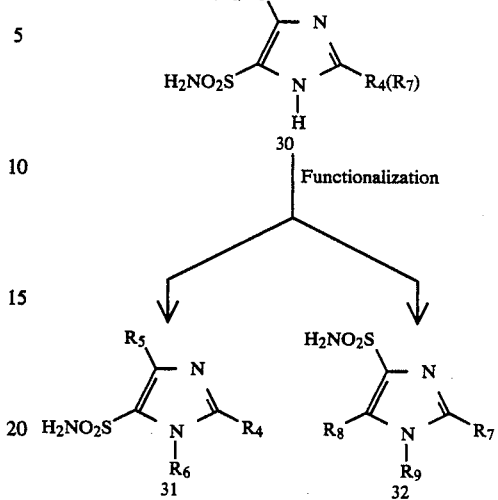

The preparation of 4-chloro or bromo-5-nitroimidazole 18 is accomplished by procedures taught in I. E. Balaban and F. L. Pyman, J. Chem. Soc., 121 947 (1922).

Protection of the imidazole nitrogen for further manipulation of the ring is accomplished with such groups as $CH_3OCH_2$— or $CH_3OCH_2CH_2O$—$CH_2$—. These groups can be introduced and removed by procedures taught in C. Tang, D. Davalian, P. Huang, and R. Breslow, J. Am. Chem. Soc., 3918 (1978) and E. J. Corey, J. L. Cras and P. Ulrich, Tet. Let. 809 (1976).

Protection and deprotection can also be accomplished with groups such as

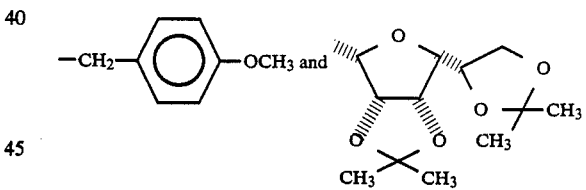

by procedures taught in T. Brown, G. Shaw and G. Durant, J. C. S. Perkin I 2310, (1980).

Protection of the imidazole as shown in Scheme I leads to a mixture of isomers 19 and 20.

The mixture is used without separation of the isomers in the following steps, since deprotection of either isomer eventually leads to the same product 30.

Introduction of $R_5$ or $R_8$ as F can be accomplished by procedures taught in U.S. Pat. No. 4,069,262 in which fluoronitrobenzene is produced from chloronitrobenzene by displacement with KF and CsF as catalyst.

Replacement of halogen in 19 and 20 to produce 21 and 22 in which $R_5$ and $R_8$ are —$S(C_1$-$C_3$ alkyl) is accomplished by displacement of halogen with the appropriate mercaptide salt as shown in Scheme 1. Details for displacement of halogen by mercaptides in halonitroimidazoles can be found in L. L. Bennett and H. T. Baker, J. Am. Chem. Soc., 79, 2188, (1957). See this same reference for methods of oxidizing nitroalkylthioimidazoles to nitroalkylsulfonylimidazoles of Formulas 21 and 22 in which $R_5$ and $R_8$ are $-SO_2(C_1-C_3$ alkyl).

Compounds of Formulas 21 and 22 in which $R_5$ and $R_8$ are $-SO_2NR_{20}R_{21}$ are produced by oxidative chlorination of the corresponding thiol or benzylmercaptide to the sulfonyl chloride. Treatment of the sulfonyl chloride with two equivalents of $R_{20}R_{21}NH$ produces the desired intermediates. This procedures is outlined in Scheme 2.

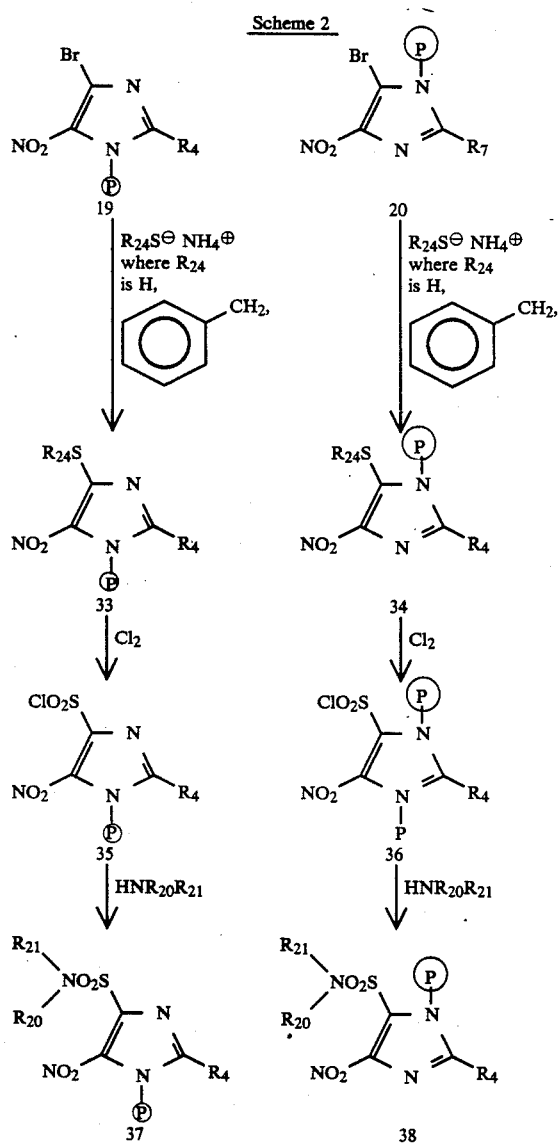

Conditions for carrying out the transformations outlined in Scheme 2 are known in the art. For example, see M. H. Fisher, W. H. Nichlolson and R. S. Stuart, Can. J. Chem., 39, 501 (1961), R. O. Roblin and J. W. Clapp, J. Am. Chem. Soc., 72, 4890 (1950) and U.S. Pat. No. 4,310,346.

Compounds of Formula 21 and 22 in which $R_5$ and $R_8$ and $OR_{16}$ and $R_{16}$ is $C_1-C_3$ alkyl are produced by displacement of halogen in 19 and 20 with the appropriate alkoxide. Suitable procedures for replacement of an activated halogen with alkoxide can be found in R. S. Kittila, "Dimethylformamide Chemical Uses", Chapter 15, E. I. du Pont de Nemours and Company, Wilmington, Delaware 19898.

Reduction of nitroimidazoles (shown in Scheme 1) of Formulas 21 and 22 in which $R_4$, $R_5$, $R_7$ and $R_8$ are as defined for Formula I can be accomplished by treatment with Adam's platinum catalyst, hydrogen and ethanol at room temperature and atmospheric pressure. For details see M. H. Fisher, W. H. Nicholson and R. S. Stuart, Can. J. Chem., 39, 501 (1961). Other suitable procedures which employ Raney nickel catalyst are taught in L. Bennett, Jr. and H. T. Baker, J. Am. Chem. Soc., 79 2188 (1957). Stannous chloride may also be used. See Fieser and Fieser, "Reagents for Organic Synthesis", Vol. I, p. 1113, J. Wiley and Sons, Inc., New York (1967) for details and references.

Imidazoles of Formula 39

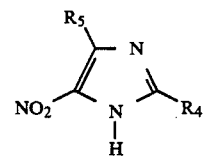

in which $R_4$ is H or $CH_3$ and $R_5$ is H or $C_1-C_4$ alkyl are produced by nitration of the corresponding imidazole 40

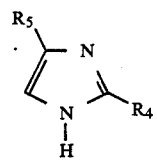

using procedures well known in imidazole chemistry. For example, see V. K. Bhagwat and F. L. Pyman, J. Chem. Soc., 127, 1832 (1925).

Conversion of 39 into the sulfonamides 41 in which $R_4$ is H or $CH_3$ and $R_5$ is H or $C_1-C_4$ alkyl is accomplished by procedures

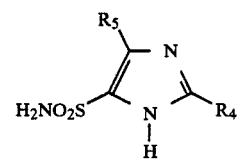

analagous to those outlined in Scheme 1.

Functionalization of 41 to produce sulfonamides 42 and 43 is outlined in Scheme 3.

Scheme 3

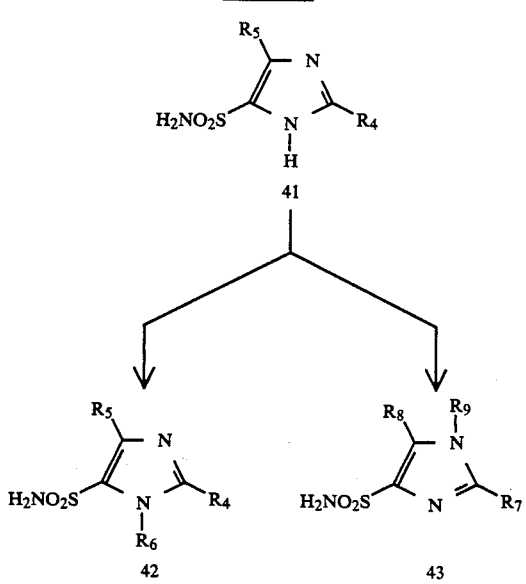

This procedure, carried out under typical conditions for alkylating or acylating nitrogen, produces the mixture of isomeric sulfonamides 42 and 43 in which $R_6$ and $R_9$ are as defined for Formula I.

Compounds of Formula 44

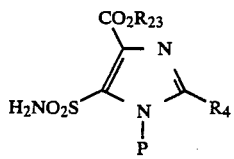

in which $R_4$ is H or $CH_3$ and $R_{23}$ is $C_1$-$C_3$ alkyl or allyl and (P) is a suitable protecting group such as t-butyl or a glycosyl group such as

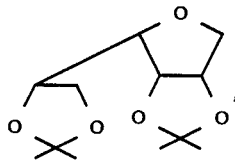

are prepared from the corresponding amino compound by diazotization, followed by coupling with $SO_2$ and HCl in the presence of a copper catalyst. The sulfonyl chlorides produced are converted to the sulfonamides by treatment with ammonia solution. This procedure is outlined in Scheme 4.

Scheme 4

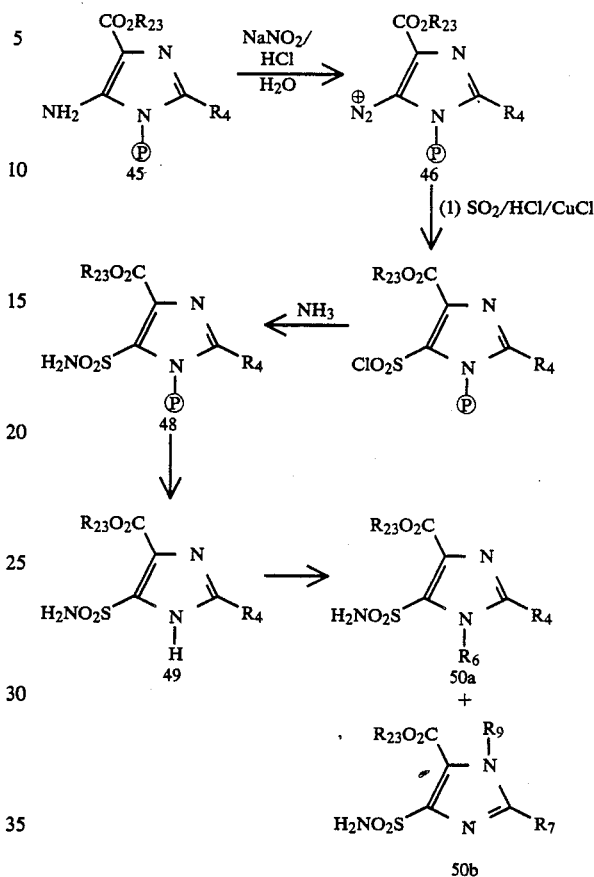

Protected amino esters 45 and the subsequent diazotization to produce diazonium chlorides 46 is taught in T. Brown, G. Shaw and G. Durant in J. Chem. Soc., Perkin Trans. I, 2304 (1980). The reaction of diazonium chlorides to produce sulfonamides is also outlined in Schemes 1 and 2. See the pertinent references cited there for the necessary details for these transformations.

Intermediates of Formula (c) in which Q is Q-4, Q-5 or Q-6 may be prepared by procedures analogous to those outlined above for the imidazole intermediates. A number of references are available which teach chemical transformations and preparation of pyrazole intermediates needed for this invention. For example:

A. N. Kost and I. I. Groundberg, Advan. Heterocyclic Chem 6, 347–429 (1966).

T. L. Jacobs, In "Heterocyclic Compounds" (R. C. Elderfield, ed.), Vol. 5, pp. 45–161, Wiley, New York, 1957.

Many of the compounds of Formula (c) in which Q is Q-4 or Q-5, for example 51, can be made by the procedures outlined in Equation 13 and Scheme 5.

Equation 13

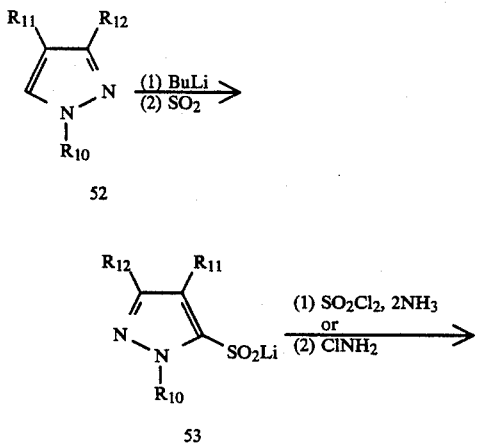

Scheme 5

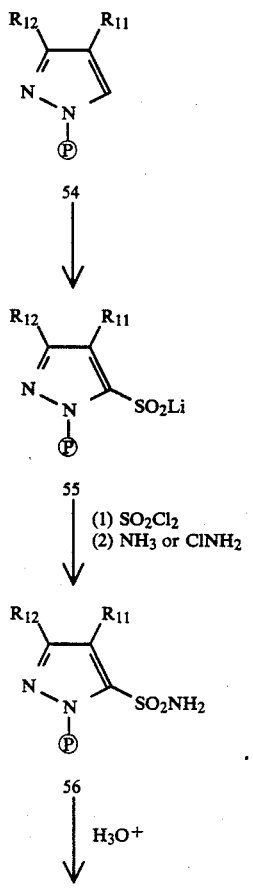

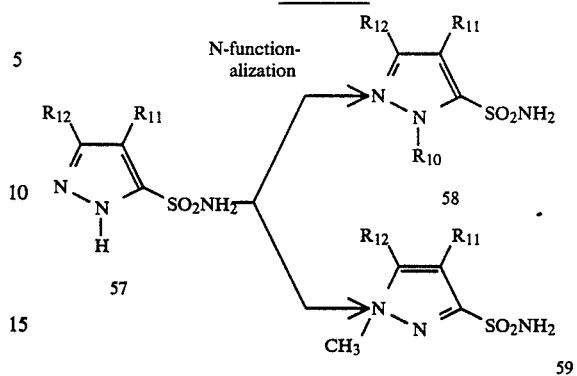

The procedure of Equation 13 is suitable for those substituents which can survive the pyrazole metallation; for example $R_{12}$ is H or $CH_3$, $R_{10}$ is $C_1$-$C_4$ alkyl, $C_3$-$C_4$ alkenyl, $C_3$-$C_4$ alkynyl or $SO_2NR_{20}R_{21}$.

Metallation reactions of pyrazoles are discussed in H. W. Gschwend and H. R. Rodriguez, "Organic Reactions", Vol. 26, p. 23, 24, John Wiley and Sons, Inc., New York, 1979.

For the pyrazoles cited above, as well as pyrazoles with groups sensitive to metallation conditions, the procedure of Scheme 5 can be used. For example, compounds in which $R_{10}$ and $R_{12}$ are as defined for Formula I and $R_{11}$ is H, $C_1$-$C_3$ alkyl, F, Cl, Br, $OR_{16}$, $S(O)_2NR_{20}R_{21}$ may be prepared. Suitable protecting groups include

$CH_2OCH_2CH_2OCH_3$ and t-butyl. See the previously cited reference for details.

Compounds of Formulas 58 and 59 in which $R_{12}$ is H or $CH_3$ and $R_{11}$ is F, Cl, Br, $OR_{16}$, $CO_2R_{24}$, $S(O)_mR_{25}$ or $SO_2NR_{20}R_{21}$ and $R_{10}$ is as defined for Example I can also be made from intermediates of Formulas 60 and 61 by using the procedures disclosed for the imidazoles in Schemes 1–4.

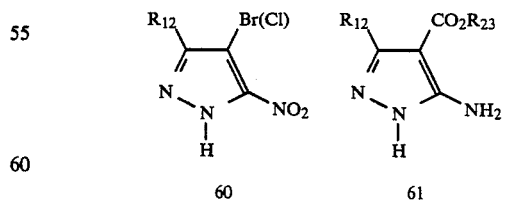

Compounds of Formula (c) in which Q is Q-6 and $R_{13}$ and $R_{14}$ are H, $C_1$-$C_3$ alkyl, $OR_{16}$, F, Cl, Br, $CO_2R_{24}$, $S(O)_mR_{25}$ and $SO_2NR_{20}R_{21}$ and $R_{15}$ is H or $CH_3$ are made by metallation at the appropriate pyrazole intermediate 64 as shown in Scheme 6.

Scheme 6

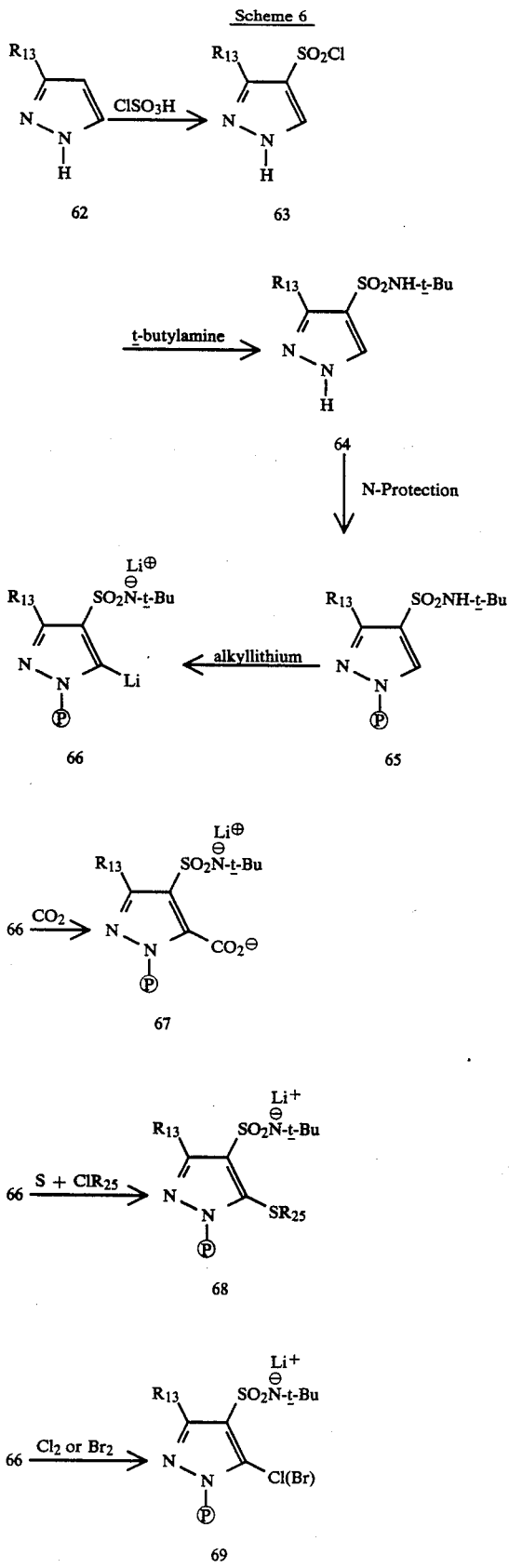

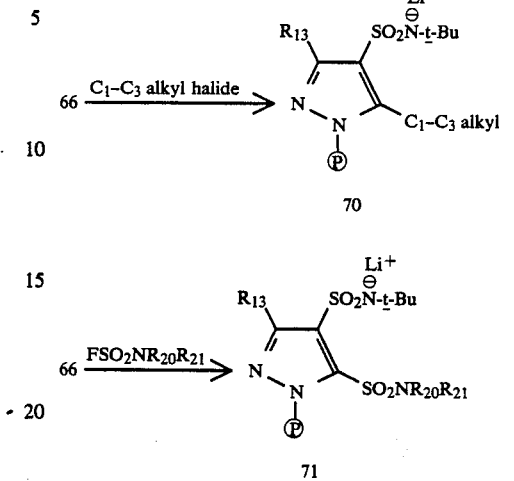

The chlorosulfonation of pyrazoles 62 and conversion to sulfonamides 64 in which $R_{13}$ is H, F, Cl, Br or $OR_{16}$ where $R_{16}$ is $C_1$-$C_3$ alkyl is carried out by procedures taught in U.S. Pat. No. 3,665,009.

Protection of the pyrazole ring can be accomplished using the tetrahydropyranyl group

(TPE) or —$CH_2OCH_2CH_2OCH_3$ (MEM). For details of this procedure with (TPE) see H. W. Gschwend and H. R. Rodriguez "Organic Reactions", Vol. 26, p. 24, John Wiley and Sons, Inc., New York, 1979. For details of this procedure with (MEM) see E. J. Corey, J. L. Grus and P. Ulrich, Tet. Let., 809 (1976).

The lithiation of protected pyrazoles and subsequent reactions with electrophiles is taught in H. W. Gschwend and H. R. Rodriguez "Organic Reactions", Vol. 26, p. 24, John Wiley and Sons, Inc., New York, 1979.

Further reaction of 67–71 to produce the appropriate sulfonamide intermediates of this invention is shown in Equations 14–16.

Equation 14

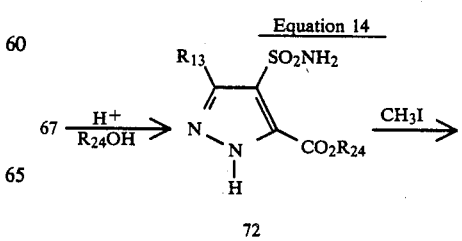

Equation 14

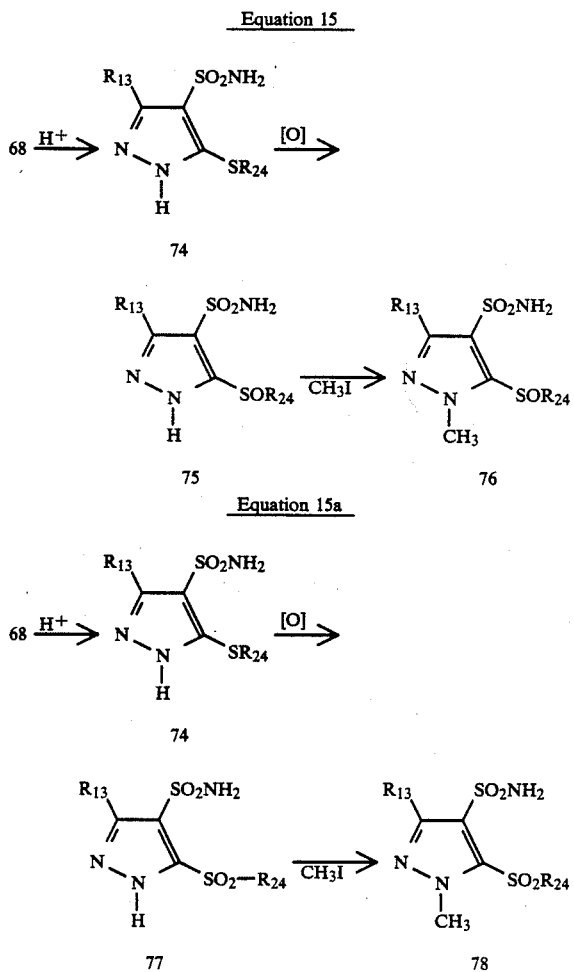

Deprotection of the sulfonamide and pyrazole is accomplished with an acid such as trifluoroacetic acid. Use of HCl in alcohol $R_{24}OH$ leads simultaneously to esterification and deprotection to yield sulfonamide 72. Alkylation of 72 with $CH_3I$ under conditions well known to those skilled in the art leads to additional intermediates 73.

Alkylthio, alkylsulfinyl and alkylsulfonyl analogs are produced from 68 using the procedure of Equations 15 or 15a. Details of this type of transformation can be found in U.S. Ser. No. 345,935, filed Feb. 8, 1982.

Equation 15

Equation 15a

The halo derivatives 79 and 80 are obtained from 69 by deprotection as shown in Equation 16.

Equation 16

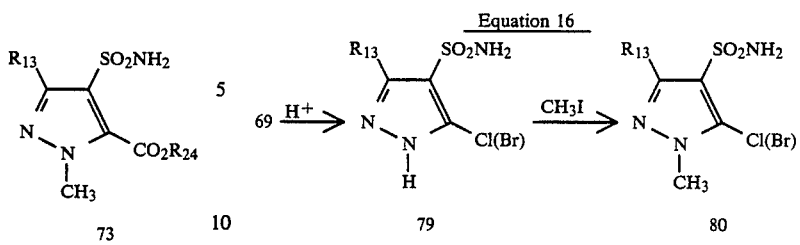

Treatment of heteroaryllithium reagents with halogens is well known in the art. Details are available in H. W. Gschwend and H. R. Rodriguez "Organic Reactions", Vol. 26, John Wiley and Sons, Inc., New York, 1979. Using similar procedures, the analogous compounds in which $R_{14}$ is $C_1$–$C_3$ alkyl 81 and $SO_2NR_{20}R_{21}$ 82 are produced.

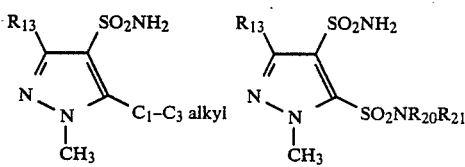

Agriculturally suitable salts of compounds of Formula I are also useful herbicides and can be prepared in a number of ways known to the art. For example, metal salts can be made by treating compounds of Formula I with a solution of alkali or alkaline earth metal salt having a sufficiently basic anion (e.g., hydroxide, alkoxide, carbonate or hydride). Quaternary amine salts can be made by similar techniques.

Salts of compounds of Formula I can also be prepared by exchange of one cation for another. Cationic exchange can be effected by direct treatment of an aqueous solution of a salt of a compound of Formula I (e.g., alkali metal or quaternary amine salt) with a solution containing the cation to be exchanged. This method is most effective when the desired salt containing the exchanged cation is insoluble in water, e.g., a copper salt, and can be separated by filtration.

Exchange may also be effected by passing an aqueous solution of a salt of a compound of Formula I (e.g., an alkali metal or quaternary amine salt) through a column packed with a cation exchange resin containing the cation to be exchanged. In this method, the cation of the resin is exchanged for that of the original salt and the desired product is eluted from the column. This method is particularly useful when the desired salt is water-soluble, e.g., a potassium, sodium or calcium salt.

Acid addition salts, useful in this invention, can be obtained by reacting a compound of Formula I or II with a suitable acid, e.g., p-toluenesulfonic acid, trichloroacetic acid or the like.

The preparation of the compounds of this invention is further illustrated by the following specific examples. Unless otherwise indicated, temperatures are in degrees centigrade.

EXAMPLE 1

1-Ethyl-1H-imidazole-2-thiol 52.2 g of Ethylisothiocyanate was added dropwise to 79.8 g of aminoacetaldehyde diethyl acetal in 600 ml of ethanol. After the addition was complete, the mixture was heated to reflux for thirty minutes. The ethanol was removed at reduced pressure on a rotary evaporator. One liter of 10% HCl was added, and the mixture was heated to reflux for thirty minutes and then cooled to room temperature. The pH of the solution was then adjusted to 3 with 50% NAOH. The product was extracted with $CH_2Cl_2$. The extracts were then dried with $MgSO_4$, filtered and concentrated on a rotary evaporator. The crude product was chromatographed on silica with 75% ethyl acetate hexane. 18.4 g of the title compound, a solid with m.p. 71°–72°, was obtained.

EXAMPLE 2

1-Ethyl-1H-imidazole-2-sulfonamide

To 17.0 g 1-ethyl-1H-imidazole-2-thiol in 180 ml 2N HCl cooled to 0° to −8° was added dropwise 19.3 ml of $Cl_2$. The temperature of the reaction was maintained at less than 10° during the addition. The reaction was stirred for about thirty minutes at 0°–10° after the addition was complete. Enough 50% NaOH was added dropwise to the reaction while maintaining the temperature, to raise the pH to 4.0. The white precipitate which formed was filtered and added to a mixture of 100 ml concentrated aqueous ammonia cooled to 0° to 10° C. The mixture was stirred for thirty minutes and then concentrated on a rotary evaporator. The concentrate was boiled three times with $CH_3CN$ and the insolubles were filtered and discarded. The $CH_3CN$ extracts were dried over $MgSO_4$, filtered and concentrated on a rotary evaporator.

11.8 g of the title compound, a white solid with m.p. 123°–125°, was obtained.

EXAMPLE 3

1-Ethyl-N-[(4-methoxy-6-methylpyrimidin-2-yl)aminocarbonyl]-1H-imidazole-2-sulfonamide (I; Q=Q-1, $R_1=C_2H_5$, $R_2=R_3=H$; A=A-1, Z=CH, X=$OCH_3$, Y=$CH_3$; R=H)

1.75 g of 1-Ethyl-1H-imidazole-2-sulfonamide in 80 ml of dry $CH_2Cl_2$ at ambient temperature under $N_2$ was treated dropwise with 6.0 ml of a 2.0M solution in hexane of $(CH_3)_3Al$. The mixture was stirred for a period of fifteen to thirty minutes. 1.97 g of methyl (4-methoxy-6-methylpyrimidin-2-yl)carbamate was then added and the mixture was refluxed for a period of sixteen hours. Enough of a 5% solution of aqueous acetic acid was then added to lower the pH to 3.0. The crude reaction mixture was extracted three times with $CH_2Cl_2$. The extracts were dried with $MgSO_4$, filtered and concentrated on a rotary evaporator. The concentrate was boiled with hot ethyl acetate and the product was filtered to yield 0.8 g of the title compound, a white solid with m.p. 178°–179° (d).

EXAMPLE 4

1-Methylpyrazole-3-sulfonyl chloride

To 120 ml of water and 120 ml of 12N hydrochloric acid was added 45 g of 1-methylpyrazole-3-amine at −10° C. followed by the dropwise addition of 33.9 g sodium nitrite dissolved in 75 ml water. The temperature was maintained at −10° C. and the mixture was stirred for an additional half hour after the additions were completed.

The above solution was then added portionwise with stirring at −10° C. to a mixture containing 348 ml acetic acid, 5.8 g of CuCl and 48 ml (liquified) of sulfur dioxide. After being stirred for one hour at −10° C., the reaction mixture was allowed to warm to 10° C. and was poured into 1500 ml of ice and water. The resultant mixture was extracted three times with 500 ml portions of methylene chloride. The extracts were combined, dried over anhydrous magnesium sulfate, filtered and evaporated in vacuo to yield a red oil. This material was used for the preparation of 1-methylpyrazole-3-sulfonamide without further purification.

EXAMPLE 5

1-Methylpyrazole-3-sulfonamide

A mixture containing chloroform (100 ml), 13.6 g of 1-methylpyrazole-3-sulfonyl chloride and 13.6 g ammonium carbonate was heated to reflux for six hours, cooled, filtered and the solid was washed with water. The water-insoluble solid which was recrystallized from 50% ethanol-water melted at 149°–151° and showed absorption peaks in the infrared at 3100 and 3200 $cm^{-1}$, consistent for the $NH_2$ in the desired product.

Anal. Calc. for $C_4H_7N_3O_2S$: C, 29.8; H, 4.38; N, 26.07; S, 19.9. Found: C, 29.3; H, 4.6; N, 25.3; S, 19.2.

EXAMPLE 6

5-Bromo-1-methyl-1H-imidazole-1-sulfonamide, 20 ml of chlorosulfonic acid was added dropwise to 6.0 g of 1H-imidazole-5-bromo-1-methyl with stirring at room temperature. The reaction mixture was heated to 100° C. for 16 hours then 140° C. for 4 hours. The reaction mixture was cooled to 0° C. and poured over cracked ice. The resulting tan solid was collected by filtration and dried under vacuum. This crude sulfonyl chloride (m.p. 84°–86° C.) was added to 200 ml of anhydrous ammonia and allowed to sit overnight at ambient temperature. Excess ammonia was removed under a flow of nitrogen and the resulting solid was crystallized from 25 ml of water yielding 3.2 g of the desired sulfonamide melting at 204°–205.5° C.

EXAMPLE 7

1,3-Dimethylpyrazole-4-sulfonamide 59 g (0.615 mmol) of 1,3-dimethylpyrazole is added slowly to 300 g (2.5 mmol) of chlorosulfonic acid at 0° C. The reaction is warmed to 90° C. for 3 hours, cooled and poured onto 500 g of ice. The aqueous solution is extracted with 3×100 ml of ether. The organic extract is dried over anhydrous sodium sulfate and filtered. The ether solution is added dropwise to a solution of 55 grams of anhydrous ammonia (2.5 mmol) in 250 ml of ether. After standing overnight, water is added and the layers separated. The aqueous solution is extracted with ethyl acetate, the organic solutions combined and dried over anhydrous sodium sulfate. After removal of the drying agent, the solvent is removed in vacuo giving 20.5 g of product, m.p. =97°–105° C.

EXAMPLE 8

N-[(4-Methoxy-6-methylpyrimidin-2-yl)aminocarbonyl]-1,3-dimethylpyrazol-4-sulfonamide (I; Q=Q-6, $R_{13}=R_{15}=CH_3$, $R_{14}=H$; A=A-1, Z=CH, X=OCH$_3$, Y=CH$_3$; R=H)

1,3-Dimethylpyrazole-4-sulfonamide (1.75 g, 10 mmol) is placed in 100 ml of 1,2-dichloroethane. Trimethylaluminum in toluene (2M, 10 ml) is added. The reaction is brought to reflux and methyl 4-methoxy-6-methyl-2-aminopyrimidine carbamate (2.0 g, 10 mmols) is added. After refluxing overnight, the reaction is cooled, poured into ice water and treated with 60 ml of 10% HCl. The layers are separated, the organic phase extracted with methylene chloride, and the organic solutions combined. The organic solution is dried with anhydrous sodium sulfate and decolorized with charcoal. The solvent is removed in vacuo. The solid is triturated with ether and collected giving 1.5 g, m.p. =207°–210° C.

By using the procedures of Examples 1-8 and the general procedures taught in Equations 1-16 and Schemes 1-6, the following compounds can be prepared.

TABLE Ia

| $R_1$ | $R_2$ | $R_3$ | R | Z | X | Y | m.p.(°C.) |
|---|---|---|---|---|---|---|---|
| H | H | H | H | CH | CH$_3$ | OCH$_3$ | |
| CH$_3$— | H | H | H | CH | CH$_3$ | CH$_3$ | 174–178° |
| CH$_3$— | H | H | H | CH | CH$_3$ | OCH$_3$ | 182–183° |
| CH$_3$— | H | H | H | CH | OCH$_3$ | OCH$_3$ | 158–165° |
| CH$_3$— | H | H | H | N | OCH$_3$ | OCH$_3$ | 170–172° |
| CH$_3$CH$_2$— | H | H | H | CH | CH$_3$ | CH$_3$ | 196–197°(d) |
| CH$_3$CH$_2$— | H | H | H | CH | CH$_3$ | OCH$_3$ | 178–179°(d) |
| CH$_3$CH$_2$— | H | H | H | CH | OCH$_3$ | OCH$_3$ | 186–187° |
| CH$_3$CH$_2$— | H | H | H | N | CH$_3$ | CH$_3$ | 141–143°(d) |
| CH$_3$CH$_2$— | H | H | H | N | CH$_3$ | OCH$_3$ | |
| CH$_3$CH$_2$— | H | H | H | N | OCH$_3$ | OCH$_3$ | 160–161° |
| CH$_3$CH$_2$— | H | H | H | CH | Cl | OCH$_3$ | |
| CH$_3$CH$_2$CH$_2$— | H | H | H | CH | CH$_3$ | CH$_3$ | 178–180° |
| CH$_3$CH$_2$CH$_2$— | H | H | H | CH | CH$_3$ | OCH$_3$ | 156–159.5° |
| CH$_3$CH$_2$CH$_2$— | H | H | H | CH | OCH$_3$ | OCH$_3$ | |
| CH$_3$CH$_2$CH$_2$— | H | H | H | CH | Cl | OCH$_3$ | |
| CH$_3$CH$_2$CH$_2$— | H | H | H | N | CH$_3$ | CH$_3$ | 122–124° |
| CH$_3$CH$_2$CH$_2$— | H | H | H | N | CH$_3$ | OCH$_3$ | |
| CH$_3$CH$_2$CH$_2$— | H | H | H | N | OCH$_3$ | OCH$_3$ | 172–174° |
| (CH$_3$)$_2$CH— | H | H | H | N | CH$_3$ | CH$_3$ | |
| (CH$_3$)$_2$CH— | H | H | H | N | OCH$_3$ | OCH$_3$ | 170–172° |
| (CH$_3$)$_2$CH— | H | H | H | N | OCH$_3$ | CH$_3$ | |
| (CH$_3$)$_2$CH— | H | H | H | CH | CH$_3$ | CH$_3$ | 185–186°(d) |
| (CH$_3$)$_2$CH— | H | H | H | CH | OCH$_3$ | OCH$_3$ | 166–167° |
| (CH$_3$)$_2$CH— | H | H | H | CH | CH$_3$ | OCH$_3$ | 157–158°(d) |
| (CH$_3$)$_2$CH— | H | H | H | CH | Cl | OCH$_3$ | |
| CH$_3$(CH$_2$)$_3$— | H | H | H | CH | CH$_3$ | OCH$_3$ | |
| CH$_3$(CH$_2$)$_3$— | H | H | H | CH | CH$_3$ | CH$_3$ | |
| CH$_3$(CH$_2$)$_3$— | H | H | H | CH | OCH$_3$ | OCH$_3$ | |
| CH$_3$(CH$_2$)$_3$— | H | H | H | CH | Cl | OCH$_3$ | |
| CH$_3$(CH$_2$)$_3$— | H | H | H | N | CH$_3$ | OCH$_3$ | |
| CH$_3$(CH$_2$)$_3$— | H | H | H | N | OCH$_3$ | OCH$_3$ | |
| CH$_3$—CH—CH$_2$CH$_3$ | H | H | H | CH | CH$_3$ | OCH$_3$ | |
| (CH$_3$)$_3$C— | H | H | H | CH | CH$_3$ | OCH$_3$ | |
| CH$_3$—CH—CH$_2$—<br>      \|<br>     CH$_3$ | H | H | H | CH | CH$_3$ | OCH$_3$ | |
| CH$_3$(CH$_2$)$_4$— | H | H | H | CH | CH$_3$ | OCH$_3$ | |
| CH$_3$CH—CH$_2$CH$_2$—<br> \|<br>CH$_3$ | H | H | H | CH | CH$_3$ | OCH$_3$ | |

TABLE Ia-continued

| $R_1$ | $R_2$ | $R_3$ | R | Z | X | Y | m.p.(°C.) |
|---|---|---|---|---|---|---|---|
| $(CH_3)_3CCH_2-$ | H | H | H | CH | $CH_3$ | $OCH_3$ | |
| $CH_3CH_2-CH-CH_2CH_3$ | H | H | H | CH | $CH_3$ | $OCH_3$ | |
| $CH_3CH-CH_2CH_2CH_3$ | H | H | H | CH | $CH_3$ | $OCH_3$ | |
| $CH_3(CH_2)_5-$ | H | H | H | CH | $CH_3$ | $OCH_3$ | |
| $CH_3(CH_2)_3CH-CH_3$ | H | H | H | CH | $CH_3$ | $OCH_3$ | |
| $CH_3(CH_2)_2CHCH_2-CH_3$ | H | H | H | CH | $CH_3$ | $OCH_3$ | |
| $CH_3CH=CH-CH_2-$ | H | H | H | CH | $CH_3$ | $OCH_3$ | |
| $CH_3C=CH_2$ | H | H | H | CH | $CH_3$ | $OCH_3$ | |
| $CH_3CH=CH-CH_2-CH_2-$ | H | H | H | CH | $CH_3$ | $OCH_3$ | |
| $CH_2=CH-CH-CH_2-CH_2CH_2$ | H | H | H | CH | CH | OCH | |
| $CH\equiv C-CH_2-CH_2-$ | H | H | H | CH | $CH_3$ | $OCH_3$ | |
| $CH\equiv C-CH-CH_3$ | H | H | H | CH | $CH_3$ | $OCH_3$ | |
| $CH\equiv C-CH-CH_2CH_3$ | H | H | H | CH | $CH_3$ | $OCH_3$ | |
| $CH_3-C\equiv C-CH-CH_2CH_3$ | H | H | H | CH | $CH_3$ | $OCH_3$ | |
| $CH_3(CH_2)_7-$ | H | H | H | CH | $CH_3$ | $OCH_3$ | |
| $CH_3(CH_2)_6-$ | H | H | H | CH | $CH_3$ | $OCH_3$ | |
| 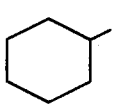 | H | H | H | CH | $CH_3$ | $OCH_3$ | |
| 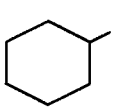 | H | H | H | CH | $CH_3$ | $OCH_3$ | |
| 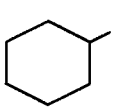 | H | H | H | CH | $CH_3$ | $CH_3$ | 182–184°(d) |

TABLE Ia-continued

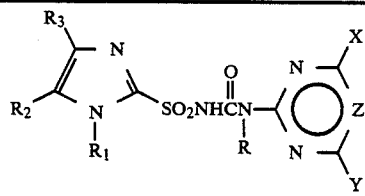

| R₁ | R₂ | R₃ | R | Z | X | Y | m.p.(°C.) |
|---|---|---|---|---|---|---|---|
| cyclohexyl | H | H | H | CH | OCH₃ | OCH₃ | 131–134°(d) |
| cyclohexyl | H | H | H | N | OCH₃ | OCH₃ | 172–174°(d) |
| cyclopropyl-CH₂ | H | H | H | CH | CH₃ | OCH₃ | |
| cyclobutyl-CH₂ | H | H | H | CH | CH₃ | OCH₃ | |
| cyclopentyl-CH₂ | H | H | H | CH | CH₃ | OCH₃ | |
| cyclohexyl-CH₂ | H | H | H | CH | CH₃ | OCH₃ | |
| 2-methylcyclopentyl-CH₂ | H | H | H | CH | CH₃ | OCH₃ | |
| CH₂=CH—CH₂— | H | H | H | CH | CH₃ | OCH₃ | |
| CH₂=CH—CH₂— | H | H | H | CH | CH₃ | CH₃ | |
| CH₂=CH—CH₂— | H | H | H | CH | OCH₃ | OCH₃ | |
| CH₂=CH—CH₂— | H | H | H | CH | Cl | OCH₃ | |
| CH₂=CH—CH₂— | H | H | H | N | CH₃ | OCH₃ | |
| CH₂=CH—CH₂— | H | H | H | N | OCH₃ | OCH₃ | |
| CH₂=CH—CH₂— | H | H | H | N | CH₃ | CH₃ | |
| —CH₂—C≡CH | H | H | H | CH | CH₃ | OCH₃ | |
| —CH₂—C≡CH | H | H | H | CH | CH₃ | CH₃ | |
| —CH₂—C≡CH | H | H | H | CH | OCH₃ | OCH₃ | |
| —CH₂—C≡CH | H | H | H | CH | Cl | OCH₃ | |
| —CH₂—C≡CH | H | H | H | N | CH₃ | CH₃ | |
| —CH₂—C≡CH | H | H | H | N | OCH₃ | OCH₃ | |
| —CH₂—C≡CH | H | H | H | N | CH₃ | OCH₃ | |
| CF₃ | H | H | H | CH | CH₃ | OCH₃ | |
| CH₂CF₃ | H | H | H | CH | CH₃ | OCH₃ | |
| CF₂CH₃ | H | H | H | CH | CH₃ | OCH₃ | |
| CF₃—CH—CH₃ | H | H | H | CH | CH₃ | OCH₃ | |
| CFH₂—CH—CH₃ | H | H | H | CH | CH₃ | OCH₃ | |
| CF₂H—CH₂—CH₂— | H | H | H | CH | CH₃ | OCH₃ | |
| CH₂Cl—CH—CH₃ | H | H | H | CH | CH₃ | OCH₃ | |

TABLE Ia-continued

| $R_1$ | $R_2$ | $R_3$ | R | Z | X | Y | m.p.(°C.) |
|---|---|---|---|---|---|---|---|
| CHCl₂—CH—CH₃<br>\| | H | H | H | CH | CH₃ | OCH₃ | |
| CCl₃—CH₂—CH₂— | H | H | H | CH | CH₃ | OCH₃ | |
| CH₂BrCH₂—CH₂— | H | H | H | CH | CH₃ | OCH₃ | |
| CF₃CH₂CH₂CH₂— | H | H | H | CH | CH₃ | OCH₃ | |
| H₂CF(CH₂)₄— | H | H | H | CH | CH₃ | OCH₃ | |
| H₂CF(CH₂)₅— | H | H | H | CH | CH₃ | OCH₃ | |
| CH₃OCH₂CH₂— | H | H | H | CH | CH₃ | OCH₃ | |
| CH₃CH₂OCH₂— | H | H | H | CH | CH₃ | OCH₃ | |
| CH₃OCH₂— | H | H | H | CH | CH₃ | OCH₃ | |
| (CH₃)₂CH—OCH₂CH₂— | H | H | H | CH | CH₃ | OCH₃ | |
| CH₃CH₂CH₂OCH₂— | H | H | H | CH | CH₃ | OCH₃ | |
| —CH₂COCH₃ | H | H | H | CH | CH₃ | OCH₃ | |
| —CH₂COCH₂CH₃ | H | H | H | CH | CH₃ | OCH₃ | |
| —CH₂COCH(CH₃)₂ | H | H | H | CH | CH₃ | OCH₃ | |
| $-\overset{O}{\underset{\|}{C}}-CH_3$ | H | H | H | CH | CH₃ | OCH₃ | |
| $-\overset{O}{\underset{\|}{C}}-CH_2CH_3$ | H | H | H | CH | CH₃ | OCH₃ | |
| $-\overset{O}{\underset{\|}{C}}-CH(CH_3)_2$ | H | H | H | CH | CH₃ | OCH₃ | |
| —CH—CO—CH₃<br>\|<br>CH₃ | H | H | H | CH | CH₃ | OCH₃ | |
| —CH₂—C(O)—OCH₃ | H | H | H | CH | CH₃ | OCH₃ | |
| —CH₂—C(O)—OCH₂CH₃ | H | H | H | CH | CH₃ | OCH₃ | |
| —CH₂—C(O)—OCH₂CH₂CH₃ | H | H | H | CH | CH₃ | OCH₃ | |
| —CH₂—C(O)—OCH(CH₃)₂ | H | H | H | CH | CH₃ | OCH₃ | |
| —CH₂—C(O)—O(CH₂)₃CH₃ | H | H | H | CH | CH₃ | OCH₃ | |
| —CH₂—C(O)—OCH₂CH(CH₃)₂ | H | H | H | CH | CH₃ | OCH₃ | |
| —CH₂—C(O)—O—CH(CH₃)CH₂CH₃ | H | H | H | CH | CH₃ | OCH₃ | |
| —CH—C(O)—OCH₃<br>\|<br>CH₃ | H | H | H | CH | CH₃ | OCH₃ | |
| —C(O)—OCH₃ | H | H | H | CH | CH₃ | OCH₃ | |

TABLE Ia-continued

| R₁ | R₂ | R₃ | R | Z | X | Y | m.p.(°C.) |
|---|---|---|---|---|---|---|---|
| −C(=O)−OCH₂CH₃ | H | H | H | CH | CH₃ | OCH₃ | |
| −C(=O)−OCH₂CH₂CH₃ | H | H | H | CH | CH₃ | OCH₃ | |
| −C(=O)−OCH(CH₃)₂ | H | H | H | CH | CH₃ | OCH₃ | |
| −C(=O)−O(CH₂)₃CH₃ | H | H | H | CH | CH₃ | OCH₃ | |
| −C(=O)OCH₂−CH(CH₃)₂ | H | H | H | CH | CH₃ | OCH₃ | |
| −C(=O)OCH(CH₃)CH₂CH₃ | H | H | H | CH | CH₃ | OCH₃ | |
| −CH₂−C(=O)−OCH₂CH=CH₂ | H | H | H | CH | CH₃ | OCH₃ | |
| −CH(CH₃)−C(=O)−OCH₂CH=CH₂ | H | H | H | CH | CH₃ | OCH₃ | |
| −C(=O)−OCH₂CH=CH₂ | H | H | H | CH | CH₃ | OCH₃ | |
| −C(=O)−O−CH₂−CH=CH−CH₃ | H | H | H | CH | CH₃ | OCH₃ | |
| −CH₂−C(=O)−OCH₂C≡CH | H | H | H | CH | CH₃ | OCH₃ | |
| −CH(CH₃)−C(=O)−OCH₂C≡CH | H | H | H | CH | CH₃ | OCH₃ | |
| −C(=O)−OCH₂C≡CH | H | H | H | CH | CH₃ | OCH₃ | |
| −C(=O)−OCH₂−C≡C−CH₃ | H | H | H | CH | CH₃ | OCH₃ | |
| −C(=O)−OCH₂CH₂Cl | H | H | H | CH | CH₃ | OCH₃ | |
| −C(=O)−OCH₂CH₂OCH₃ | H | H | H | CH | CH₃ | OCH₃ | |
| −C(=O)−SCH₃ | H | H | H | CH | CH₃ | OCH₃ | |

TABLE Ia-continued

[Structure: imidazole ring with R3, R2, R1 substituents, connected via SO2NHC(O)N(R) to a pyrimidine ring with X, Y, Z substituents]

| R₁ | R₂ | R₃ | R | Z | X | Y | m.p.(°C.) |
|---|---|---|---|---|---|---|---|
| −C(O)−S−(CH₂)₃CH₃ | H | H | H | CH | CH₃ | OCH₃ | |
| −C(O)−S−CH₂−CH=CH₂ | H | H | H | CH | CH₃ | OCH₃ | |
| −C(O)−S−CH₂−CH=CH−CH₃ | H | H | H | CH | CH₃ | OCH₃ | |
| −C(O)−N(CH₃)₂ | H | H | H | CH | CH₃ | OCH₃ | |
| −C(O)−N(CH₃)CH₂CH₃ | H | H | H | CH | CH₃ | OCH₃ | |
| −C(O)−N(CH₂CH₃)₂ | H | H | H | CH | CH₃ | OCH₃ | |
| −CH₂−C(O)−N(CH₃)₂ | H | H | H | CH | CH₃ | OCH₃ | |
| −CH₂−SO₂−N(CH₃)₂ | H | H | H | CH | CH₃ | OCH₃ | |
| −CH(CH₃)−SO₂−N(CH₂CH₃)₂ | H | H | H | CH | CH₃ | OCH₃ | |
| −CH₂−SO₂−N−(CH₃)CH₂CH₃ | H | H | H | CH | CH₃ | OCH₃ | |
| −SO₂−N(CH₃)₂ | H | H | H | CH | CH₃ | OCH₃ | |
| −SO₂N(CH₃)(CH₂CH₃) | H | H | H | CH | CH₃ | OCH₃ | |
| −SO₂N(CH₂CH₃)₂ | H | H | H | CH | CH₃ | OCH₃ | |
| −CH₂−SO₂CH₃ | H | H | H | CH | CH₃ | OCH₃ | |
| −CH₂SO₂CF₃ | H | H | H | CH | CH₃ | OCH₃ | |
| −CH₂SO₂CH₂CH₃ | H | H | H | CH | CH₃ | OCH₃ | |
| −CH₂SO₂CH₂CH₂CH₃ | H | H | H | CH | CH₃ | OCH₃ | |
| −SO₂CH₃ | H | H | H | CH | CH₃ | OCH₃ | |
| −SO₂CF₃ | H | H | H | CH | CH₃ | OCH₃ | |
| −SO₂CH₂CH₃ | H | H | H | CH | CH₃ | OCH₃ | |
| −SO₂CH₂CH₂CH₃ | H | H | H | CH | CH₃ | OCH₃ | |
| −SO₂−CH(CH₃)₂ | H | H | H | CH | CH₃ | OCH₃ | |
| −CH(CH₃)−SO₂CH₃ | H | H | H | CH | CH₃ | OCH₃ | |
| −CH₂−SO₂CH(CH₃)₂ | H | H | H | CH | CH₃ | OCH₃ | |
| −SO₂CH₃ | H | H | H | CH | CH₃ | CH₃ | |
| −SO₂CH₃ | H | H | H | CH | OCH₃ | OCH₃ | |
| −SO₂CH₃ | H | H | H | CH | Cl | OCH₃ | |
| −SO₂CF₃ | H | H | H | CH | OCH₃ | OCH₃ | |
| −SO₂CF₃ | H | H | H | CH | Cl | OCH₃ | |
| −CH₂SO₂CH₃ | H | H | H | CH | OCH₃ | OCH₃ | |
| −CH₂SO₂CH₃ | H | H | H | CH | Cl | OCH₃ | |
| −CH₂−C₆H₅ | H | H | H | CH | CH₃ | OCH₃ | |

TABLE Ia-continued

*Structure: Imidazole (with R3 at 4-position N, R2 at 5-position, R1 on N1) — SO2NHC(=O)N(R) — pyrimidine/triazine ring (with X, Z, Y substituents)*

| R1 | R2 | R3 | R | Z | X | Y | m.p.(°C.) |
|---|---|---|---|---|---|---|---|
| —CH2—C6H4—Cl (4-Cl benzyl) | H | H | H | CH | CH3 | OCH3 | |
| —CH2—C6H4—F (2-F benzyl) | H | H | H | CH | CH3 | OCH3 | |
| —C6H4—NO2 (4-NO2 phenyl) | H | H | H | CH | CH3 | OCH3 | |
| —C6H4—Br (3-Br phenyl) | H | H | H | CH | CH3 | OCH3 | |
| —C6H4—OCH3 (4-OCH3 phenyl) | H | H | H | CH | CH3 | OCH3 | |
| —C6H4—CF3 (4-CF3 phenyl) | H | H | H | CH | CH3 | OCH3 | |
| —CH2CH3 | H | H | CH3 | CH | CH3 | OCH3 | |
| —CH2CH3 | H | H | CH3 | CH | OCH3 | OCH3 | |
| —CH2CH3 | H | H | CH3 | CH | CH3 | CH3 | |
| —CH2CH3 | H | H | CH3 | N | OCH3 | OCH3 | |
| —CH2CH3 | H | H | CH3 | N | CH3 | OCH3 | |
| —CH2CH3 | CH3 | H | H | CH | CH3 | CH3 | |
| —CH2CH3 | H | CH3 | H | CH | CH3 | CH3 | |
| —CH2CH3 | CH3 | CH3 | H | CH | CH3 | CH3 | |
| —CH2CH3 | H | H | H | CH | CH3 | CH2CH3 | |
| —CH2CH3 | H | H | H | CH | CH3 | OCH2CH3 | |
| —CH2CH3 | H | H | H | CH | CH3 | CH2OCH3 | |
| —CH2CH3 | H | H | H | N | CH3 | CH(OCH3)2 | |
| —CH2CH3 | H | H | H | CH | OCH3 | —NH2 | |
| —CH2CH3 | H | H | H | N | OCH3 | CH3NH— | |
| —CH2CH3 | H | H | H | N | OCH3 | (CH3)2N— | |
| —CH2CH3 | H | H | H | CH | OCF2H | CH3 | |
| —CH2CH3 | H | H | H | CH | OCF2H | OCH3 | |
| —CH2CH3 | H | H | H | N | OCF2H | CH3 | |
| —CH2CH3 | H | H | H | CH | SCF2H | CH3 | |
| —CH2CH3 | H | H | H | CH | SCF2H | OCH3 | |
| —CH2CH3 | H | H | H | CH | SCF2H | OCF3 | |
| —CH2CH3 | H | H | H | CH | CH3 | OCH2CF3 | |
| —CH2CH3 | H | H | H | CH | OCH3 | OCH2CF3 | |
| —CH2CH3 | H | H | H | CH | CH3 | OCF3 | |
| —CH2CH3 | H | H | H | CH | OCH3 | OCF3 | |
| —CH2CH3 | H | H | H | N | CH3 | OCF3 | |
| —CH2CH3 | H | H | H | CH | CH3 | OCF2CHClF | |
| —CH2CH3 | H | H | H | CH | CH3 | OCF2CF2H | |
| —CH2CH3 | H | H | H | CH | OCH3 | OCF2CF2H | |
| —CH2CH3 | H | H | H | N | CH3 | OCF2CF2H | |
| —CH2CH3 | H | H | H | CH | CH3 | OCF2CHFCF3 | |
| —CH2CH3 | H | H | H | CH | OCH3 | OCF2CHFCF3 | |

TABLE Ia-continued

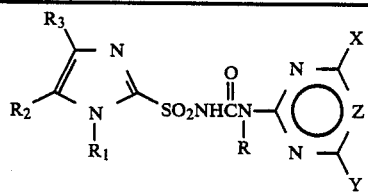

| $R_1$ | $R_2$ | $R_3$ | R | Z | X | Y | m.p.(°C.) |
|---|---|---|---|---|---|---|---|
| —$CH_2CH_3$ | H | H | H | CH | $OCF_2H$ | $CH_2CH_3$ | |
| —$CH_2CH_3$ | H | H | H | CH | $OCF_2H$ | $OCH_2CH_3$ | |
| —$CH_2CH_3$ | H | H | H | CH | $OCF_2H$ | $CH_2OCH_3$ | |
| —$CH_2CH_3$ | H | H | H | CH | $OCF_2H$ | $CH(OCH_3)_2$ | |
| —$CH_2CH_3$ | H | H | H | CH | $OCF_2H$ | $OCH_2CF_3$ | |
| —$CH_2CH_3$ | H | H | H | CH | $OCF_2H$ | $OCF_3$ | |
| —$CH_2CH_3$ | H | H | H | CH | $OCF_2H$ | $NH_2$ | |
| —$CH_2CH_3$ | H | H | H | CH | $OCF_2H$ | $NHCH_3$ | |
| —$CH_2CH_3$ | H | H | H | CH | $OCF_2H$ | $N(CH_3)_2$ | |
| —$CH_2CH_3$ | H | H | H | CH | $OCF_2H$ | $OCF_2H$ | |
| —$CH_2CH_3$ | H | H | H | CH | $OCF_2H$ | $OCF_2CHClF$ | |
| —$CH_2CH_3$ | H | H | H | CH | $OCF_2H$ | $OCF_2CHBrF$ | |
| —$CH_2CH_3$ | H | H | H | CH | $OCF_2H$ | $OCF_2CF_2H$ | |
| —$CH_2CH_3$ | H | H | H | CH | $OCF_2H$ | $OCF_2CHFCF_3$ | |
| —$CH_2CH_3$ | H | H | H | CH | $CH_3$ | $OCF_2CF_2H$ | |
| —$CH_2CH_3$ | H | H | H | N | $OCF_2H$ | $CH_2CH_3$ | |
| —$CH_2CH_3$ | H | H | H | N | $OCF_2H$ | $CH_2OCH_3$ | |
| —$CH_2CH_3$ | H | H | H | N | $OCF_2H$ | $OCH_2CF_3$ | |
| —$CH_2CH_3$ | H | H | H | N | $OCF_2H$ | $NH_2$ | |
| —$CH_2CH_3$ | H | H | H | N | $OCF_2H$ | $N(CH_3)_2$ | |
| —$CH_2CH_3$ | H | H | H | N | $OCF_2H$ | $OCF_2CHBrF$ | |
| —$CH_2CH_3$ | H | H | H | N | $OCF_2H$ | $OCF_2CHFCF_3$ | |
| —$CH_2CH_3$ | H | H | H | N | $OCF_2H$ | $OCF_2H$ | |
| —$CH_2CH_3$ | H | H | H | N | $CH_3$ | $OCF_2H$ | |

TABLE Ib

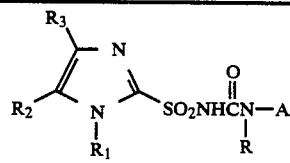

TABLE Ib-continued

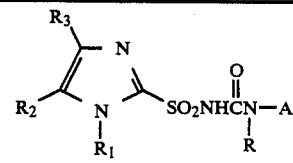

| $R_1$ | $R_2$ | $R_3$ | R | A | $Y^1$ | m.p. (°C.) | $R_1$ | $R_2$ | $R_3$ | R | A | $Y^1$ | m.p. (°C.) |
|---|---|---|---|---|---|---|---|---|---|---|---|---|---|
| —$CH_2CH_3$ | H | H | H | A-2 | H | | —$CH_2CH_3$ | H | H | H | A-3 | $OCH_3$ | |
| —$CH_2CH_3$ | H | H | H | A-2 | $CH_3$ | | —$CH_2CH_3$ | H | H | H | A-3 | $OCF_2H$ | |
| —$CH_2CH_3$ | H | H | H | A-2 | Cl | | —$CH_2CH_3$ | H | H | H | A-4 | H | |
| —$CH_2CH_3$ | H | H | H | A-2 | $OCH_3$ | | —$CH_2CH_3$ | H | H | H | A-4 | Cl | |
| —$CH_2CH_3$ | H | H | H | A-2 | $OCF_2H$ | | —$CH_2CH_3$ | H | H | H | A-4 | $CH_3$ | |
| —$CH_2CH_3$ | H | H | H | A-3 | H | | —$CH_2CH_3$ | H | H | H | A-4 | $OCH_3$ | |
| —$CH_2CH_3$ | H | H | H | A-3 | Cl | | —$CH_2CH_3$ | H | H | H | A-4 | $OCF_2H$ | |
| —$CH_2CH_3$ | H | H | H | A-3 | $CH_3$ | | | | | | | | |

TABLE Ic

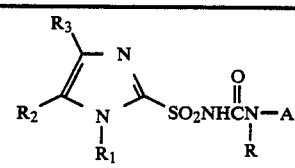

| $R_1$ | $R_2$ | $R_3$ | R | A | $X^2$ | $Y^2$ | $X^3$ | m.p. (°C.) |
|---|---|---|---|---|---|---|---|---|
| —$CH_2CH_3$ | H | H | H | A-5 | $OCH_3$ | $CH_3$ | — | |
| —$CH_2CH_3$ | H | H | H | A-5 | $CH_3$ | $CH_2CH_3$ | — | |
| —$CH_2CH_3$ | H | H | H | A-5 | $CH_3$ | $CH_2CF_3$ | — | |
| —$CH_2CH_3$ | H | H | H | A-5 | $OCH_3$ | $CH_3$ | — | |
| —$CH_2CH_3$ | H | H | H | A-5 | $OCH_3$ | $CH_2CH_3$ | — | |
| —$CH_2CH_3$ | H | H | H | A-5 | $OCH_3$ | $CH_2CF_3$ | — | |
| —$CH_2CH_3$ | H | H | H | A-5 | $CH_2CH_3$ | $CH_3$ | — | |
| —$CH_2CH_3$ | H | H | H | A-5 | $CH_2CH_3$ | $CH_2CH_3$ | — | |
| —$CH_2CH_3$ | H | H | H | A-5 | $CH_2CH_3$ | $CH_2CF_3$ | — | |
| —$CH_2CH_3$ | H | H | H | A-5 | $OCH_2CH_3$ | $CH_3$ | — | |
| —$CH_2CH_3$ | H | H | H | A-5 | $OCH_2CH_3$ | $CH_2CH_3$ | — | |
| —$CH_2CH_3$ | H | H | H | A-5 | $OCH_2CH_3$ | $CH_2CF_3$ | — | |

TABLE Ic-continued

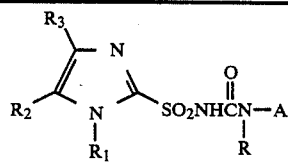

| R₁ | R₂ | R₃ | R | A | X² | Y² | X³ | m.p. (°C.) |
|---|---|---|---|---|---|---|---|---|
| —CH₂CH₃ | H | H | H | A-5 | SCH₃ | CH₃ | — | |
| —CH₂CH₃ | H | H | H | A-5 | SCH₃ | CH₂CH₃ | — | |
| —CH₂CH₃ | H | H | H | A-5 | SCH₃ | CH₂CF₃ | — | |
| —CH₂CH₃ | H | H | H | A-5 | SCH₂CH₃ | CH₃ | — | |
| —CH₂CH₃ | H | H | H | A-5 | SCH₂CH₃ | CH₂CH₃ | — | |
| —CH₂CH₃ | H | H | H | A-5 | SCH₂CH₃ | CH₂CF₃ | — | |
| —CH₂CH₃ | H | H | H | A-6 | — | — | OCH₃ | |
| —CH₂CH₃ | H | H | H | A-6 | — | — | CH₃ | |

TABLE IIa

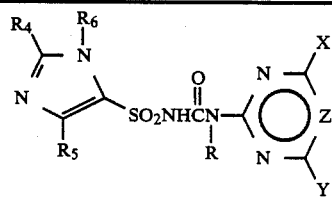

| R₆ | R₅ | R₄ | R | Z | X | Y | m.p. (°C.) |
|---|---|---|---|---|---|---|---|
| —CH₃ | H | CH₃ | H | CH | CH₃ | OCH₃ | |
| —CH₃ | H | H | H | CH | CH₃ | OCH₃ | 158–163° |
| CH₃ | H | H | H | CH | CH₃ | CH₃ | 171–179° |
| CH₃CH₂— | H | H | H | CH | CH₃ | OCH₃ | |
| CH₃CH₂CH₂— | H | H | H | CH | CH₃ | OCH₃ | |
| (CH₃)₂CH— | H | H | H | CH | CH₃ | OCH₃ | |
| CH₃CH—CH₂—<br>    \|<br>    CH₃ | H | H | H | CH | CH₃ | OCH₃ | |
| CH₃CH—CH₂CH₃<br>   \| | H | H | H | CH | CH₃ | OCH₃ | |
| (CH₃)₃C— | H | H | H | CH | CH₃ | OCH₃ | |
| CH₃CH=CH— | H | H | H | CH | CH₃ | OCH₃ | |
| —CH₂CH=CH₂ | H | H | H | CH | CH₃ | OCH₃ | |
| CH₃—CH=CH—CH₂— | H | H | H | CH | CH₃ | OCH₃ | |
| HC≡C—CH₂— | H | H | H | CH | CH₃ | OCH₃ | |
| CH₃—C≡C—CH₂— | H | H | H | CH | CH₃ | OCH₃ | |
| CF₃ | H | H | H | CH | CH₃ | OCH₃ | |
| CF₃CH₂— | H | H | H | CH | CH₃ | OCH₃ | |
| H₂CFCH₂CH₂— | H | H | H | CH | CH₃ | OCH₃ | |
| ClCH₂CH₂CH₂— | H | H | H | CH | CH₃ | OCH₃ | |
| HCFClCH₂CH₂CH₂— | H | H | H | CH | CH₃ | OCH₃ | |
| Br(CH₂)₄— | H | H | H | CH | CH₃ | OCH₃ | |
| CH₃OCH₂— | H | H | H | CH | CH₃ | OCH₃ | |
| CH₃OCH₂CH₂— | H | H | H | CH | CH₃ | OCH₃ | |
| —CO₂CH₃ | H | H | H | CH | CH₃ | OCH₃ | |
| —CO₂CH₂CH₃ | H | H | H | CH | CH₃ | OCH₃ | |
| —CO₂CH₂CH₂CH₃ | H | H | H | CH | CH₃ | OCH₃ | |
| —CO₂CH(CH₃)₂ | H | H | H | N | CH₃ | OCH₃ | |
| —CO₂CH₂CH=CH₂ | H | H | H | N | CH₃ | OCH₃ | |
| —CO₂CH₂—C≡CH | H | H | H | N | CH₃ | OCH₃ | |
| —CO₂CH₂CH=CH—CH₃ | H | H | H | N | CH₃ | OCH₃ | |
| —CO₂CH₂—C≡C—CH₃ | H | H | H | N | CH₃ | OCH₃ | |
| —CO₂CH₂CH₂OCH₃ | H | H | H | N | CH₃ | OCH₃ | |
| —CO₂CH₂CH₂Cl | H | H | H | N | CH₃ | OCH₃ | |
| —SO₂N(CH₃)₂ | H | H | H | N | CH₃ | OCH₃ | |
| —SO₂N(CH₃)(CH₂CH₃) | H | H | H | N | CH₃ | OCH₃ | |
| —SO₂N(CH₂CH₃)₂ | H | H | H | N | CH₃ | OCH₃ | |
| —SO₂CH₃ | H | H | H | N | CH₃ | OCH₃ | |
| —SO₂CF₃ | H | H | H | N | CH₃ | OCH₃ | |
| —SO₂CH₂CH₃ | H | H | H | N | CH₃ | OCH₃ | |
| —SO₂CH₂CH₂CH₃ | H | H | H | N | CH₃ | OCH₃ | |
| —SO₂CH(CH₃)₂ | H | H | H | N | CH₃ | OCH₃ | |
| CH₃CH₂— | H | H | H | CH | CH₃ | CH₃ | |
| CH₃CH₂— | H | H | H | CH | Cl | OCH₃ | |

TABLE IIa-continued

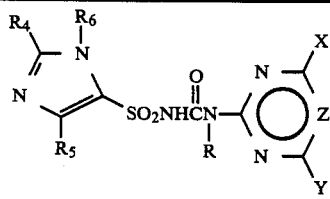

| R6 | R5 | R4 | R | Z | X | Y | m.p. (°C.) |
|---|---|---|---|---|---|---|---|
| CH3CH2— | H | H | H | CH | OCH3 | OCH3 | |
| CH3CH2— | H | H | H | N | OCH3 | OCH3 | |
| CH3CH2— | H | H | H | N | CH3 | OCH3 | |
| CH3CH2— | H | H | H | N | CH3 | CH3 | |
| CH3CH2— | H | H | CH3 | CH | OCH3 | CH3 | |
| CH3CH2— | H | H | CH3 | CH | CH3 | CH3 | |
| CH3CH3— | H | H | CH3 | CH | OCH3 | OCH3 | |
| CH3CH2— | H | H | CH3 | N | OCH3 | OCH3 | |
| CH3CH2— | H | H | CH3 | N | OCH3 | CH3 | |
| CH3 | CH3 | H | H | CH | CH3 | OCH3 | |
| CH3 | Cl | H | H | CH | CH3 | OCH3 | |
| CH3 | CO2CH3 | H | H | CH | CH3 | OCH3 | |
| CH3 | NO2 | H | H | CH | CH3 | OCH3 | |
| CH3 | SO2N(CH3)2 | H | H | CH | CH3 | OCH3 | |
| —CO2CH3 | CH3 | H | H | CH | CH3 | OCH3 | |
| —SO2N(CH3)2 | CH3 | H | H | CH | CH3 | OCH3 | |
| H | F | H | H | CH | CH3 | OCH3 | |
| H | Br | H | H | CH | CH3 | OCH3 | |
| CH3CH3 | CH2 | H | H | CH | CH3 | OCH3 | |
| CH3 | CH3CH2CH2 | H | H | CH | CH3 | OCH3 | |
| CH3 | CH3(CH2)3— | H | H | CH | CH3 | OCH3 | |
| CH3 | (CH3)2CHCH2— | H | H | CH | CH3 | OCH3 | |
| CH3 | CH3CHCH2CH3 | H | H | CH | CH3 | OCH3 | |
| CH3 | —CO2CH3 | H | H | CH | CH3 | OCH3 | |
| CH3 | —CO2CH2CH3 | H | H | CH | CH3 | OCH3 | |
| CH3 | —CO2CH2CH2CH3 | H | H | CH | CH3 | OCH3 | |
| CH3 | —CO2CH(CH3)2 | H | H | CH | CH3 | OCH3 | |
| CH3 | SO2N(CH3)2 | H | H | CH | OCH3 | OCH3 | |
| CH3 | SO2N(CH3)(CH2CH3) | H | H | CH | OCH3 | OCH3 | |
| CH3 | SO2N(CH2CH3) | H | H | CH | OCH3 | OCH3 | |
| CH3 | SCH3 | H | H | CH | OCH3 | OCH3 | |
| CH3 | SOCH3 | H | H | CH | OCH3 | OCH3 | |
| CH3 | SO2CH2CH3 | H | H | CH | OCH3 | OCH3 | |
| CH3 | SO2CH2CH2CH3 | H | H | CH | OCH3 | OCH3 | |
| CH3 | SCH2CH3 | H | H | CH | OCH3 | OCH3 | |
| CH3 | SCH2CH2CH3 | H | H | CH | OCH3 | OCH3 | |
| CH3 | SO2CH(CH3)2 | H | H | CH | OCH3 | OCH3 | |
| CH3CH2— | H | H | H | CH | CH3 | CH3CH2 | |
| H | H | H | H | CH | CH3 | CH3 | 240–242 |
| H | H | H | H | CH | CH3 | OCH3 | 207–208.5 |
| H | H | H | H | CH | OCH3 | OCH3 | 211–216 |
| H | H | H | H | N | CH3 | CH3 | 188–193 |
| H | H | H | H | N | CH3 | OCH3 | |
| H | H | H | H | N | OCH3 | OCH3 | 150–158 |
| CH3CH2— | H | H | H | CH | CH3 | —OCH2CH3 | |
| CH3CH2— | H | H | H | CH | CH3 | —CH2OCH3 | |
| CH3CH2— | H | H | H | CH | CH3 | —CH2(OCH3)2 | |
| CH3CH2— | H | H | H | CH | OCH3 | —NH2 | |
| CH3CH2— | H | H | H | N | OCH3 | —NHCH3 | |
| CH3CH2— | H | H | H | N | OCH3 | —N(CH3)2 | |
| —CH2CH3 | H | H | H | CH | OCF2H | CH3 | |
| —CH2CH3 | H | H | H | CH | OCF2H | OCH3 | |
| —CH2CH3 | H | H | H | N | OCF2H | CH3 | |
| —CH2CH3 | H | H | H | CH | SCF2H | CH3 | |
| —CH2CH3 | H | H | H | CH | SCF2H | OCH3 | |
| —CH2CH3 | H | H | H | CH | SCF2H | OCF3 | |
| —CH2CH3 | H | H | H | CH | CH3 | OCH2CF3 | |
| —CH2CH3 | H | H | H | CH | OCH3 | OCH2CF3 | |
| —CH2CH3 | H | H | H | CH | CH3 | OCF3 | |
| —CH2CH3 | H | H | H | CH | OCH3 | OCF3 | |
| —CH2CH3 | H | H | H | N | CH3 | OCF3 | |
| —CH2CH3 | H | H | H | CH | CH3 | OCF2CHClF | |
| —CH2CH3 | H | H | H | CH | CH3 | OCF2CF2H | |
| —CH2CH3 | H | H | H | CH | OCH3 | OCF2CF2H | |
| —CH2CH3 | H | H | H | N | CH3 | OCF2CF2H | |
| —CH2CH3 | H | H | H | CH | CH3 | OCF2CHFCF3 | |
| —CH2CH3 | H | H | H | CH | OCH3 | OCF2CHFCF3 | |

TABLE IIa-continued

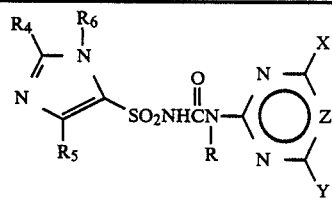

| R6 | R5 | R4 | R | Z | X | Y | m.p. (°C.) |
|---|---|---|---|---|---|---|---|
| —CH2CH3 | H | H | H | CH | OCF2H | CH2CH3 | |
| —CH2CH3 | H | H | H | CH | OCF2H | OCH2CH3 | |
| —CH2CH3 | H | H | H | CH | OCF2H | CH2OCH3 | |
| —CH2CH3 | H | H | H | CH | OCF2H | CH(OCH3)2 | |
| —CH2CH3 | H | H | H | CH | OCF2H | OCH2CF3 | |
| —CH2CH3 | H | H | H | CH | OCF2H | OCF3 | |
| —CH2CH3 | H | H | H | CH | OCF2H | NH2 | |
| —CH2CH3 | H | H | H | CH | OCF2H | NHCH3 | |
| —CH2CH3 | H | H | H | CH | OCF2H | N(CH3)2 | |
| —CH2CH3 | H | H | H | CH | OCF2H | OCF2H | |
| —CH2CH3 | H | H | H | CH | OCF2H | OCF2CHClF | |
| —CH2CH3 | H | H | H | CH | OCF2H | OCF2CHBrF | |
| —CH2CH3 | H | H | H | CH | OCF2H | OCF2CF2H | |
| —CH2CH3 | H | H | H | CH | OCF2H | OCF2CHFCF3 | |
| —CH2CH3 | H | H | H | CH | CH3 | OCF2CF2H | |
| —CH2CH3 | H | H | H | N | OCF2H | CH2CH3 | |
| —CH2CH3 | H | H | H | N | OCF2H | CH2OCH3 | |
| —CH2CH3 | H | H | H | N | OCF2H | OCH2CF3 | |
| —CH2CH3 | H | H | H | N | OCF2H | NH2 | |
| —CH2CH3 | H | H | H | N | OCF2H | N(CH3)2 | |
| —CH2CH3 | H | H | H | N | OCF2H | OCF2CHBrF | |
| —CH2CH3 | H | H | H | N | OCF2H | OCF2CHFCF3 | |
| —CH2CH3 | H | H | H | N | OCF2H | OCF2H | |
| —CH2CH3 | H | H | H | N | CH3 | OCF2H | |

TABLE IIb

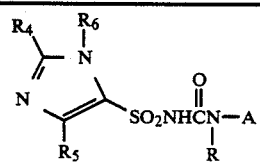

| R6 | R5 | R4 | R | A | Y1 | m.p. (°C.) |
|---|---|---|---|---|---|---|
| —CH3CH2 | H | H | H | A-2 | H | |
| —CH3CH2 | H | H | H | A-2 | Cl | |
| —CH3CH2 | H | H | H | A-2 | CH3 | |
| —CH3CH2 | H | H | H | A-2 | OCH3 | |
| CH3CH2 | H | H | H | A-2 | OCF2H | |
| H | —CO2CH3 | H | H | A-3 | H | |
| H | —CO2CH3 | H | H | A-3 | Cl | |
| H | —CO2CH3 | H | H | A-3 | CH3 | |

TABLE IIb-continued

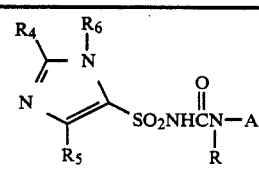

| R6 | R5 | R4 | R | A | Y1 | m.p. (°C.) |
|---|---|---|---|---|---|---|
| H | —CO2CH3 | H | H | A-3 | OCH3 | |
| CH3CH2 | H | H | H | A-2 | OCF2H | |
| H | SO2N(CH3)2 | H | H | A-4 | H | |
| H | SO2N(CH3)2 | H | H | A-4 | Cl | |
| H | SO2N(CH3)2 | H | H | A-4 | CH3 | |
| H | SO2N(CH3)2 | H | H | A-4 | OCH3 | |
| CH3CH2 | H | H | H | A-4 | OCF2H | |

TABLE IIc

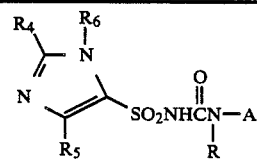

| R6 | R5 | R4 | R | A | X2 | Y2 | X3 | m.p. (°C.) |
|---|---|---|---|---|---|---|---|---|
| H | SO2CH3 | H | H | A-5 | OCH3 | CH3 | — | |
| H | SO2CH3 | H | H | A-5 | OCH3 | CH2CH3 | — | |
| H | SO2CH3 | H | H | A-5 | OCH3 | CH2CF3 | — | |
| H | SO2CH3 | H | H | A-5 | CH3 | CH3 | — | |
| H | SO2CH3 | H | H | A-5 | CH3 | CH2CH3 | — | |
| H | SO2CH3 | H | H | A-5 | CH3 | CH2CF3 | — | |
| H | SO2CH3 | H | H | A-5 | CH2CH3 | CH3 | — | |
| H | SO2CH3 | H | H | A-5 | CH2CH3 | CH2CH3 | — | |
| H | SO2CH3 | H | H | A-5 | CH2CH3 | CH2CF3 | — | |
| H | SO2CH3 | H | H | A-5 | OCH2CH3 | CH3 | — | |
| H | SO2CH3 | H | H | A-5 | OCH2CH3 | CH2CH3 | — | |
| H | SO2CH3 | H | H | A-5 | OCH2CH3 | CH2CF3 | — | |

TABLE IIc-continued

| R6 | R5 | R4 | R | A | X² | Y² | X³ | m.p. (°C.) |
|---|---|---|---|---|---|---|---|---|
| H | SO₂CH₃ | H | H | A-5 | SCH₃ | CH₃ | — | |
| H | SO₂CH₃ | H | H | A-5 | SCH₃ | CH₂CH₃ | — | |
| H | SO₂CH₃ | H | H | A-5 | SCH₃ | CH₂CF₃ | — | |
| H | SO₂CH₃ | H | H | A-5 | SCH₂CH₃ | CH₃ | — | |
| H | SO₂CH₃ | H | H | A-5 | SCH₂CH₃ | CH₂CH₃ | — | |
| H | SO₂CH₃ | H | H | A-5 | SCH₂CH₃ | CH₂CF₃ | — | |
| H | SO₂CH₃ | H | H | A-6 | — | — | OCH₃ | |
| H | SO₂CH₃ | H | H | A-6 | — | — | CH₃ | |

TABLE IIIa

| R8 | R9 | R7 | R | Z | X | Y | m.p. (°C.) |
|---|---|---|---|---|---|---|---|
| H | CH₃ | CH₃ | H | CH | CH₃ | OCH₃ | |
| H | CH₃ | H | H | CH | CH₃ | OCH₃ | |
| CH₃— | CH₃ | H | H | CH | CH₃ | OCH₃ | |
| CH₃CH₂— | CH₃ | H | H | CH | CH₃ | OCH₃ | |
| CH₃CH₂CH₂— | CH₃ | H | H | CH | CH₃ | OCH₃ | |
| CH₃(CH₂)₃— | CH₃ | H | H | CH | CH₃ | OCH₃ | |
| (CH₃)₂CHCH₂— | CH₃ | H | H | CH | CH₃ | OCH₃ | |
| (CH₃)₃C— | CH₃ | H | H | CH | CH₃ | OCH₃ | |
| CH₃CHCH₂CH₃ | CH₃ | H | H | CH | CH₃ | OCH₃ | |
| CH₂=CH—CH₂— | CH₃ | H | H | CH | CH₃ | OCH₃ | |
| CH₃CH=CH—CH₂— | CH₃ | H | H | CH | CH₃ | OCH₃ | |
| HC≡C—CH₂— | CH₃ | H | H | CH | CH₃ | OCH₃ | |
| CH₃C≡C—CH₂— | CH₃ | H | H | CH | CH₃ | OCH₃ | |
| —OCH₃ | CH₃ | H | H | CH | CH₃ | OCH₃ | |
| —OCH₂CH₃ | CH₃ | H | H | CH | CH₃ | OCH₃ | |
| —OCH(CH₃)₂ | CH₃ | H | H | CH | CH₃ | OCH₃ | |
| —OCH₂CH₂CH₃ | CH₃ | H | H | CH | CH₃ | OCH₃ | |
| —NO₂ | CH₃ | H | H | CH | CH₃ | OCH₃ | |
| —F | CH₃ | H | H | CH | CH₃ | OCH₃ | |
| —Cl | CH₃ | H | H | CH | CH₃ | OCH₃ | |
| —CO₂CH₃ | CH₃ | H | H | CH | CH₃ | OCH₃ | |
| —CO₂CH₂CH₃ | CH₃ | H | H | CH | CH₃ | OCH₃ | |
| —CO₂CH₂CH₂CH₃ | CH₃ | H | H | CH | CH₃ | OCH₃ | |
| —CO₂CH(CH₃)₂ | CH₃ | H | H | CH | CH₃ | OCH₃ | |
| —CO₂CH₂CH=CH₂ | CH₃ | H | H | CH | CH₃ | OCH₃ | |
| —S—CH₃ | CH₃ | H | H | CH | CH₃ | OCH₃ | |
| —SOCH₃ | CH₃ | H | H | CH | CH₃ | OCH₃ | |
| —SCH₂CH₃ | CH₃ | H | H | CH | CH₃ | OCH₃ | |
| —SCH₂CH₂CH₃ | CH₃ | H | H | CH | CH₃ | OCH₃ | |
| —SCH(CH₃)₂ | CH₃ | H | H | CH | CH₃ | OCH₃ | |
| —SO₂CH₃ | CH₃ | H | H | CH | CH₃ | OCH₃ | |
| —SO₂CH₂CH₃ | CH₃ | H | H | CH | CH₃ | OCH₃ | |
| —SO₂CH₂CH₂CH₃ | CH₃ | H | H | CH | CH₃ | OCH₃ | |
| —SO₂CH(CH₃)₂ | CH₃ | H | H | CH | CH₃ | OCH₃ | |
| —SO₂N(CH₃)₂ | CH₃ | H | H | CH | CH₃ | OCH₃ | |
| —SO₂N(CH₃)(CH₂CH₃) | CH₃ | H | H | CH | CH₃ | OCH₃ | |
| —CO₂CH₃ | CH₃CH₂— | H | H | CH | CH₃ | OCH₃ | |
| —CO₂CH₃ | CH₃ | H | H | CH | CH₃ | CH₃ | |
| —CO₂CH₃ | CH₃ | H | H | CH | OCH₃ | OCH₃ | |
| —CO₂CH₃ | CH₃ | H | H | CH | Cl | OCH₃ | |
| —CO₂CH₃ | CH₃ | H | H | N | CH₃ | CH₃ | |
| —CO₂CH₃ | CH₃ | H | H | N | CH₃O | CH₃ | |
| —CO₂CH₃ | CH₃ | H | H | N | CH₃O | CH₃O | |
| —CO₂CH₃ | CH₃ | H | H | N | CH₃O | NH₂ | |
| —CO₂CH₃ | CH₃ | H | H | N | CH₃O | NHCH₃ | |

TABLE IIIa-continued

| R8 | R9 | R7 | R | Z | X | Y | m.p. (°C.) |
|---|---|---|---|---|---|---|---|
| —CO₂CH₃ | CH₃ | H | H | N | CH₃O | N(CH₃)₂ | |
| —CO₂CH₃ | CH₃ | H | H | N | CH₃ | OCH₂CH₃ | |
| —CO₂CH₃ | CH₃ | H | H | N | CH₃ | CH₂OCH₃ | |
| —CO₂CH₃ | CH₃ | H | H | N | CH₃ | CH(OCH₃)₂ | |
| H | CH₃CH₂— | H | H | CH | CH₃ | OCH₃ | 215–216 |
| H | SO₂N(CH₃)₂ | H | H | CH | CH₃ | OCH₃ | 185–188 |
| H | SO₂N(CH₃)₂ | H | H | N | CH₃ | OCH₃ | 118–125 |
| H | SO₂N(CH₃)₂ | H | H | CH | CH₃ | CH₃ | 195–202 |
| H | CH₃ | H | H | CH | CH₃ | OCH₃ | 222–224.5 |
| H | CH₃ | H | H | N | CH₃ | CH₃ | 188–193 |
| Br | CH₃ | H | H | CH | CH₃ | CH₃ | 241–243 |
| Br | CH₃ | H | H | CH | CH₃ | OCH₃ | 208–210.5 |
| Br | CH₃ | H | H | CH | OCH₃ | OCH₃ | 205–206 |
| Br | CH₃ | H | H | N | CH₃ | CH₃ | 202.5–204 |
| Br | CH₃ | H | H | N | CH₃ | OCH₃ | 192–194 |
| Br | CH₃ | H | H | N | OCH₃ | OCH₃ | |
| Br | CH₃ | H | H | CH | CH₃ | OCF₂H | |
| Cl | CH₃ | H | H | CH | CH₃ | CH₃ | 233–235 |
| Cl | CH₃ | H | H | CH | CH₃ | OCH₃ | 204–207 |
| Cl | CH₃ | H | H | CH | OCH₃ | OCH₃ | 170–178 |
| Cl | CH₃ | H | H | N | CH₃ | CH₃ | 200–203 |
| Cl | CH₃ | H | H | N | CH₃ | OCH₃ | 191–193 |
| Cl | CH₃ | H | H | N | OCH₃ | OCH₃ | 194–200 |
| Cl | CH₃ | H | H | CH | CH₃ | OCF₂H | |
| Br | H | H | H | CH | CH₃ | CH₃ | 234.5–237 |
| Br | H | H | H | CH | OCH₃ | OCH₃ | 208–215 |
| Br | H | H | H | N | CH₃ | CH₃ | |
| Br | H | H | H | N | CH₃ | OCH₃ | |
| Br | H | H | H | N | OCH₃ | OCH₃ | |
| —CH₂CH₃ | CH₃ | H | H | CH | OCF₂H | CH₃ | |
| —CH₂CH₃ | CH₃ | H | H | CH | OCF₂H | OCH₃ | |
| —CH₂CH₃ | CH₃ | H | H | N | OCF₂H | CH₃ | |
| —CH₂CH₃ | CH₃ | H | H | CH | SCF₂H | CH₃ | |
| —CH₂CH₃ | CH₃ | H | H | CH | SCF₂H | OCH₃ | |
| —CH₂CH₃ | CH₃ | H | H | CH | SCF₂H | OCF₃ | |
| —CH₂CH₃ | CH₃ | H | H | CH | CH₃ | OCH₂CF₃ | |
| —CH₂CH₃ | CH₃ | H | H | CH | OCH₃ | OCH₂CF₃ | |
| —CH₂CH₃ | CH₃ | H | H | CH | CH₃ | OCF₃ | |
| —CH₂CH₃ | CH₃ | H | H | CH | OCH₃ | OCF₃ | |
| —CH₂CH₃ | CH₃ | H | H | N | CH₃ | OCF₃ | |
| —CH₂CH₃ | CH₃ | H | H | CH | CH₃ | OCF₂CHClF | |
| —CH₂CH₃ | CH₃ | H | H | CH | CH₃ | OCF₂CF₂H | |
| —CH₂CH₃ | CH₃ | H | H | CH | OCH₃ | OCF₂CF₂H | |
| —CH₂CH₃ | CH₃ | H | H | N | CH₃ | OCF₂CF₂H | |
| —CH₂CH₃ | CH₃ | H | H | CH | CH₃ | OCF₂CHFCF₃ | |
| —CH₂CH₃ | CH₃ | H | H | CH | OCH₃ | OCF₂CHFCF₃ | |
| —CH₂CH₃ | CH₃ | H | H | CH | OCF₂H | CH₂CH₃ | |
| —CH₂CH₃ | CH₃ | H | H | CH | OCF₂H | OCH₂CH₃ | |
| —CH₂CH₃ | CH₃ | H | H | CH | OCF₂H | CH₂OCH₃ | |
| —CH₂CH₃ | CH₃ | H | H | CH | OCF₂H | CH(OCH₃)₂ | |
| —CH₂CH₃ | CH₃ | H | H | CH | OCF₂H | OCH₂CF₃ | |
| —CH₂CH₃ | CH₃ | H | H | CH | OCF₂H | OCF₃ | |
| —CH₂CH₃ | CH₃ | H | H | CH | OCF₂H | NH₂ | |
| —CH₂CH₃ | CH₃ | H | H | CH | OCF₂H | NHCH₃ | |
| —CH₂CH₃ | CH₃ | H | H | CH | OCF₂H | N(CH₃)₂ | |
| —CH₂CH₃ | CH₃ | H | H | CH | OCF₂H | OCF₂H | |
| —CH₂CH₃ | CH₃ | H | H | CH | OCF₂H | OCF₂CHClF | |
| —CH₂CH₃ | CH₃ | H | H | CH | OCF₂H | OCF₂CHBrF | |
| —CH₂CH₃ | CH₃ | H | H | CH | OCF₂H | OCF₂CF₂H | |
| —CH₂CH₃ | CH₃ | H | H | CH | OCF₂H | OCF₂CHFCF₃ | |
| —CH₂CH₃ | CH₃ | H | H | CH | CH₃ | OCF₂CF₂H | |
| —CH₂CH₃ | CH₃ | H | H | N | OCF₂H | CH₂CH₃ | |
| —CH₂CH₃ | CH₃ | H | H | N | OCF₂H | CH₂OCH₃ | |
| —CH₂CH₃ | CH₃ | H | H | N | OCF₂H | OCH₂CF₃ | |
| —CH₂CH₃ | CH₃ | H | H | N | OCF₂H | NH₂ | |
| —CH₂CH₃ | CH₃ | H | H | N | OCF₂H | N(CH₃)₂ | |
| —CH₂CH₃ | CH₃ | H | H | N | OCF₂H | OCF₂CHBrF | |
| —CH₂CH₃ | CH₃ | H | H | N | OCF₂H | OCF₂CHFCF₃ | |
| —CH₂CH₃ | CH₃ | H | H | N | OCF₂H | OCF₂H | |

TABLE IIIa-continued

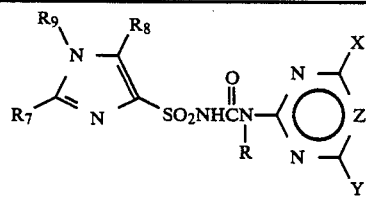

| R8 | R9 | R7 | R | Z | X | Y | m.p. (°C.) |
|---|---|---|---|---|---|---|---|
| —CH2CH3 | CH3 | H | H | N | CH3 | OCF2H | |

TABLE IIIb

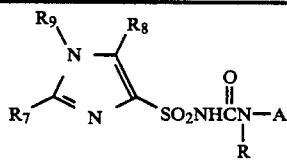

| R8 | R9 | R7 | R | A | Y1 | m.p. (°C.) |
|---|---|---|---|---|---|---|
| —SO2N(CH3)2 | CH3 | H | H | A-2 | H | |
| —SO2N(CH3)2 | CH3 | H | H | A-2 | Cl | |
| —SO2N(CH3)2 | CH3 | H | H | A-2 | CH3 | |
| —SO2N(CH3)2 | CH3 | H | H | A-2 | OCH3 | |
| —SO2N(CH3)2 | CH3 | H | H | A-2 | OCF2H | |
| —SO2N(CH3)2 | CH3 | H | H | A-3 | H | |
| —SO2N(CH3)2 | CH3 | H | H | A-3 | Cl | |
| —SO2N(CH3)2 | CH3 | H | H | A-3 | CH3 | |

TABLE IIIb-continued

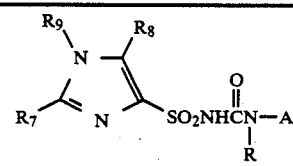

| R8 | R9 | R7 | R | A | Y1 | m.p. (°C.) |
|---|---|---|---|---|---|---|
| —SO2N(CH3)2 | CH3 | H | H | A-3 | OCH3 | |
| —SO2N(CH3)2 | CH3 | H | H | A-3 | OCF2H | |
| —SO2N(CH3)2 | CH3 | H | H | A-4 | H | |
| —SO2N(CH3)2 | CH3 | H | H | A-4 | CH3 | |
| —SO2N(CH3)2 | CH3 | H | H | A-4 | Cl | |
| —SO2N(CH3)2 | CH3 | H | H | A-4 | OCH3 | |
| —SO2N(CH3)2 | CH3 | H | H | A-4 | OCF2H | |

TABLE IIIc

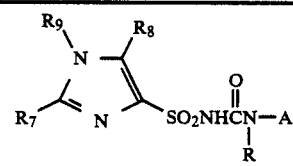

| R8 | R9 | R7 | R | A | X2 | Y2 | X3 | m.p. (°C.) |
|---|---|---|---|---|---|---|---|---|
| —SO2CH3 | CH3 | H | H | A-5 | OCH3 | CH3 | — | |
| —SO2CH3 | CH3 | H | H | A-5 | OCH3 | CH2CH3 | — | |
| —SO2CH3 | CH3 | H | H | A-5 | OCH3 | CH2CF3 | — | |
| —SO2CH3 | CH3 | H | H | A-5 | CH3 | CH3 | — | |
| —SO2CH3 | CH3 | H | H | A-5 | CH3 | CH2CH3 | — | |
| —SO2CH3 | CH3 | H | H | A-5 | CH3 | CH2CF3 | — | |
| —SO2CH3 | CH3 | H | H | A-5 | CH2CH3 | CH3 | — | |
| —SO2CH3 | CH3 | H | H | A-5 | CH2CH3 | CH2CH3 | — | |
| —SO2CH3 | CH3 | H | H | A-5 | CH2CH3 | CH2CF3 | — | |
| —SO2CH3 | CH3 | H | H | A-5 | OCH2CH3 | CH3 | — | |
| —SO2CH3 | CH3 | H | H | A-5 | OCH2CH3 | CH2CH3 | — | |
| —SO2CH3 | CH3 | H | H | A-5 | OCH2CH3 | CH2CF3 | — | |
| —SO2CH3 | CH3 | H | H | A-5 | SCH3 | CH3 | — | |
| —SO2CH3 | CH3 | H | H | A-5 | SCH3 | CH2CH3 | — | |
| —SO2CH3 | CH3 | H | H | A-5 | SCH3 | CH2CF3 | — | |
| —SO2CH3 | CH3 | H | H | A-5 | SCH2CH3 | CH3 | — | |
| —SO2CH3 | CH3 | H | H | A-5 | SCH2CH3 | CH2CH3 | — | |
| —SO2CH3 | CH3 | H | H | A-5 | SCH2CH3 | CH2CF3 | — | |
| Br | CH3 | H | H | A-5 | OCH3 | CH3 | — | |
| Br | CH3 | H | H | A-5 | CH3 | CH2CF3 | — | |
| Br | CH3 | H | H | A-5 | SCH3 | CH2CH3 | — | |
| Br | CH3 | H | H | A-5 | SCH2CH3 | CH2CF3 | — | |
| SO2CH3 | CH3 | H | H | A-6 | — | — | OCH3 | |
| SO2CH3 | CH3 | H | H | A-6 | — | — | CH3 | |
| Br | CH3 | H | H | A-6 | — | — | OCH3 | |
| Br | CH3 | H | H | A-6 | — | — | CH3 | |

TABLE IVa

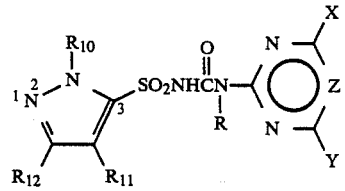

| R₁₀ | R₁₁ | R₁₂ | R | Z | X | Y | m.p. (°C.) |
|---|---|---|---|---|---|---|---|
| H | H | H | H | CH | CH₃ | OCH₃ | |
| CH₃ | H | H | H | CH | CH₃ | OCH₃ | |
| CH₃CH₂— | H | H | H | CH | CH₃ | OCH₃ | |
| CH₃CH₂CH₂— | H | H | H | CH | CH₃ | OCH₃ | |
| (CH₃)₂CH— | H | H | H | CH | CH₃ | OCH₃ | |
| CH₃(CH₂)₃— | H | H | H | CH | CH₃ | OCH₃ | |
| (CH₃)₂CHCH₂— | H | H | H | CH | CH₃ | OCH₃ | |
| CH₃—CH—CH₂CH₃ | H | H | H | CH | CH₃ | OCH₃ | |
| (CH₃)₃C— | H | H | H | CH | CH₃ | OCH₃ | |
| CH₂=CH—CH₂— | H | H | H | CH | CH₃ | OCH₃ | |
| CH₃CH=CH—CH₂— | H | H | H | CH | CH₃ | OCH₃ | |
| —CH₂—C≡CH | H | H | H | CH | CH₃ | OCH₃ | |
| CH₃—C≡C—CH₂— | H | H | H | CH | CH₃ | OCH₃ | |
| —CO₂CH₃ | H | H | H | CH | CH₃ | OCH₃ | |
| —CO₂CH₂CH₃ | H | H | H | CH | CH₃ | OCH₃ | |
| —CO₂CH₂CH₂CH₃ | H | H | H | CH | CH₃ | OCH₃ | |
| —CO₂CH(CH₃)₂ | H | H | H | CH | CH₃ | OCH₃ | |
| —CO₂CH₂CH=CH₂ | H | H | H | CH | CH₃ | OCH₃ | |
| —SO₂N(CH₃)₂ | H | H | H | CH | CH₃ | OCH₃ | |
| —SO₂N(CH₃)(CH₂CH₃) | H | H | H | CH | CH₃ | OCH₃ | |
| —SO₂N(CH₃CH₃)₂ | H | H | H | CH | CH₃ | OCH₃ | |
| —SO₂CH₃ | H | H | H | CH | CH₃ | OCH₃ | |
| —SO₂CF₃ | H | H | H | CH | CH₃ | OCH₃ | |
| —SO₂CH₂CH₃ | H | H | H | CH | CH₃ | OCH₃ | |
| —SO₂CH₂CH₂CH₃ | H | H | H | CH | CH₃ | OCH₃ | |
| —SO₂CH(CH₃)₂ | H | H | H | CH | CH₃ | OCH₃ | |
| —CH₂CH₃ | H | H | H | CH | CH₃ | CH₃ | |
| —CH₂CH₃ | H | H | H | CH | OCH₃ | OCH₃ | |
| —CH₂CH₃ | H | H | H | CH | Cl | OCH₃ | |
| —CH₂CH₃ | H | H | H | N | CH₃ | CH₃ | |
| —CH₂CH₃ | H | H | H | N | CH₃ | OCH₃ | |
| —CH₂CH₃ | H | H | H | N | OCH₃ | OCH₃ | |
| —CH₂CH₃ | H | H | H | N | CH₃O | —NHCH₃ | |
| —CH₂CH₃ | H | H | H | N | CH₃O | —N(CH₃)₂ | |
| —CO₂CH₃ | H | H | H | CH | CH₃ | CH₃ | |
| —CO₂CH₃ | H | H | H | CH | OCH₃ | OCH₃ | |
| —CO₂CH₃ | H | H | H | CH | Cl | OCH₃ | |
| —CO₂CH₃ | H | H | H | N | CH₃ | CH₃ | |
| —CO₂CH₃ | H | H | H | N | CH₃ | OCH₃ | |
| —CO₂CH₃ | H | H | H | N | CH₃ | OCH₂CH₃ | |
| —CO₂CH₃ | H | H | H | N | OCH₃ | OCH₃ | |
| —CO₂CH₃ | H | H | H | CH | Cl | NH₂ | |
| —SO₂N(CH₃)₂ | H | H | H | CH | CH₃ | CH₃ | |
| —SO₂N(CH₃)₂ | H | H | H | CH | OCH₃ | OCH₃ | |
| —SO₂N(CH₃)₂ | H | H | H | CH | Cl | OCH₃ | |
| —SO₂N(CH₃)₂ | H | H | H | N | CH₃ | CH₃ | |
| —SO₂N(CH₃)₂ | H | H | H | N | CH₃ | OCH₃ | |
| —SO₂N(CH₃)₂ | H | H | H | N | CH₃ | OCH₂CH₃ | |
| —SO₂N(CH₃)₂ | H | H | H | N | OCH₃ | N(CH₃)₂ | |
| CH₃ | —CO₂CH₂CH₂CH₃ | H | H | CH | OCH₃ | OCH₃ | |
| CH₃ | —CO₂CH₂CH=CH₂ | H | H | CH | CH₃ | CH₃ | |
| CH₃ | —SCH₃ | H | H | CH | Cl | OCH₃ | |
| CH₃ | —SCH₂CH₂CH₃ | H | H | N | OCH₃ | OCH₃ | |
| CH₃ | —SCH₂CH(CH₃)₂ | H | H | N | CH₃ | OCH₃ | |
| CH₃ | —SOCH₃ | H | H | N | OCH₃ | N(CH₃)₂ | |
| CH₃ | —SOCH₂CH₃ | H | H | CH | CH₃ | OCH₃ | |
| CH₃ | —SOCH₂CH₂CH₃ | H | H | CH | CH₃ | OCH₃ | |
| CH₃ | —SO₂CH₃ | H | H | CH | CH₃ | OCH₃ | |
| CH₃ | —SO₂CH₂CH₃ | H | H | CH | CH₃ | OCH₃ | |
| CH₃ | —SO₂CH₂CH₂CH₃ | H | H | CH | CH₃ | OCH₃ | |
| CH₃ | —SO₂N(CH₃)₂ | H | H | CH | CH₃ | OCH₃ | |
| CH₃ | —SO₂N(CH₃)(CH₂CH₃) | H | H | CH | CH₃ | OCH₃ | |
| CH₃ | —SO₂N(CH₂CH₃)₂ | H | H | CH | CH₃ | OCH₃ | |
| H | —CH₂CH₃ | H | H | CH | OCH₃ | OCH₃ | |
| H | —CH(CH₃)₂ | H | H | CH | CH₃ | CH₃ | |
| CH₃ | F | H | H | CH | CH₃ | OCH₃ | |
| H | Cl | H | H | CH | Cl | OCH₃ | |

TABLE IVa-continued

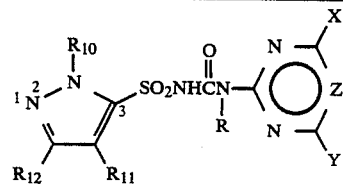

| R10 | R11 | R12 | R | Z | X | Y | m.p. (°C.) |
|---|---|---|---|---|---|---|---|
| CH3 | Br | H | H | N | CH3 | OCH3 | |
| H | NO2 | H | H | N | OCH3 | OCH3 | |
| CH3 | OCH3 | H | H | N | CH3O | N(CH3)2 | |
| CH3 | —OCH2CH3 | H | H | CH | CH3O | NHCH3 | |
| CH3 | —OCH2CH2CH3 | H | H | CH | CH3 | OCH3 | |
| H | —NO2 | H | H | CH | CH3 | OCH3 | |
| H | —CO2CH3 | H | H | CH | CH3 | OCH3 | |
| H | —CO2CH2CH3 | H | H | CH | CH3 | OCH3 | |
| CH3 | —CO2CH(CH3)2 | H | H | CH | CH3 | OCH3 | |
| H | Cl | H | H | CH | OCH3 | OCH3 | |
| CH3CH2— | Cl | H | H | CH | OCH3 | OCH3 | |
| CH3CH2— | OCH3 | H | H | CH | OCH3 | OCH3 | |
| CH3CH2— | NO2 | H | H | CH | OCH3 | OCH3 | |
| CH3CH2— | CH3 | H | H | CH | OCH3 | OCH3 | |
| CH3 | —CO2CH3 | H | H | CH | CH3 | CH3 | |
| CH3 | —CO2CH3 | H | H | CH | OCH3 | OCH3 | |
| CH3 | —CO2CH3 | H | H | CH | Cl | OCH3 | |
| CH3 | —CO2CH3 | H | H | CH | Cl | NH2 | |
| CH3 | —CO2CH3 | H | H | N | OCH3 | OCH3 | |
| CH3 | —CO2CH3 | H | H | N | CH3 | OCH3 | |
| CH3 | —CO2CH3 | H | H | N | CH3 | CH3 | |
| CH3 | —CO2CH3 | H | H | N | OCH3 | —NHCH3 | |
| CH3 | —CO2CH3 | H | H | N | OCH3 | —N(CH3)2 | |
| CH3 | —SO2N(CH3)2 | H | H | CH | OCH3 | OCH3 | |
| CH3 | —SO2N(CH3)2 | H | H | CH | CH3 | CH3 | |
| CH3 | —SO2N(CH3)2 | H | H | CH | Cl | OCH3 | |
| CH3 | —SO2N(CH3)2 | H | H | CH | Cl | NH2 | |
| CH3 | —SO2N(CH3)2 | H | H | N | OCH3 | OCH3 | |
| CH3 | —SO2N(CH3)2 | H | H | N | CH3 | OCH3 | |
| CH3 | —SO2N(CH3)2 | H | H | N | CH3 | CH3 | |
| CH3 | —SO2N(CH3)2 | H | H | N | CH3O | —NHCH3 | |
| CH3 | —SO2N(CH3)2 | H | H | N | CH3O | —N(CH3)2 | |
| CH3 | —SO2CH3 | H | H | CH | OCH3 | OCH3 | |
| CH3 | —SO2CH3 | H | H | CH | Cl | OCH3 | |
| CH3 | —SO2CH3 | H | H | N | OCH3 | —NHCH3 | |
| CH3 | —SO2CH3 | H | H | N | OCH3 | —N(CH3)2 | |
| CH3 | —CO2CH3 | H | H | CH | CH3 | —OCH2CH3 | |
| CH3 | —CO2CH3 | H | H | CH | CH3 | —CH2OCH3 | |
| CH3 | —CO2CH3 | H | H | CH | CH3 | —CH2(OCH3)2 | |
| CH3CH2— | —CO2CH3 | H | CH3 | CH | CH3 | OCH3 | |
| CH3CH2— | —CO2CH3 | H | CH3 | CH | CH3 | CH3 | |
| CH3CH2— | —CO2CH3 | H | CH3 | CH | OCH3 | OCH3 | |
| CH3CH2— | —CO2CH3 | H | CH3 | N | OCH3 | OCH3 | |
| CH3CH2— | —CO2CH3 | H | CH3 | N | OCH3 | CH3 | |
| —CH2CH3 | H | H | H | CH | OCF2H | CH3 | |
| —CH2CH3 | H | H | H | CH | OCF2H | OCH3 | |
| —CH2CH3 | H | H | H | N | OCF2H | CH3 | |
| —CH2CH3 | H | H | H | CH | SCF2H | CH3 | |
| —CH2CH3 | H | H | H | CH | SCF2H | OCH3 | |
| —CH2CH3 | H | H | H | CH | SCF2H | OCF3 | |
| —CH2CH3 | H | H | H | CH | CH3 | OCH2CF3 | |
| —CH2CH3 | H | H | H | CH | OCH3 | OCH2CF3 | |
| —CH2CH3 | H | H | H | CH | CH3 | OCF3 | |
| —CH2CH3 | H | H | H | CH | OCH3 | OCF3 | |
| —CH2CH3 | H | H | H | N | CH3 | OCF3 | |
| —CH2CH3 | H | H | H | CH | CH3 | OCF2CHClF | |
| —CH2CH3 | H | H | H | CH | CH3 | OCF2CF2H | |
| —CH2CH3 | H | H | H | CH | OCH3 | OCF2CF2H | |
| —CH2CH3 | H | H | H | N | CH3 | OCF2CF2H | |
| —CH2CH3 | H | H | H | CH | CH3 | OCF2CHFCF3 | |
| —CH2CH3 | H | H | H | CH | OCH3 | OCF2CHFCF3 | |
| —CH2CH3 | H | H | H | CH | OCF2H | CH2CH3 | |
| —CH2CH3 | H | H | H | CH | OCF2H | OCH2CH3 | |
| —CH2CH3 | H | H | H | CH | OCF2H | CH2OCH3 | |
| —CH2CH3 | H | H | H | CH | OCF2H | CH(OCH3)2 | |
| —CH2CH3 | H | H | H | CH | OCF2H | OCH2CF3 | |
| —CH2CH3 | H | H | H | CH | OCF2H | OCF3 | |
| —CH2CH3 | H | H | H | CH | OCF2H | NH2 | |
| —CH2CH3 | H | H | H | CH | OCF2H | NHCH3 | |
| —CH2CH3 | H | H | H | CH | OCF2H | N(CH3)2 | |
| —CH2CH3 | H | H | H | CH | OCF2H | OCF2H | |

TABLE IVa-continued

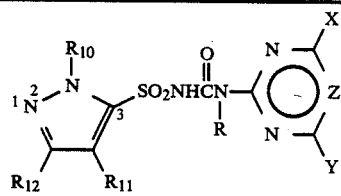

| R10 | R11 | R12 | R | Z | X | Y | m.p. (°C.) |
|---|---|---|---|---|---|---|---|
| —CH2CH3 | H | H | H | CH | OCF2H | OCF2CHClF | |
| —CH2CH3 | H | H | H | CH | OCF2H | OCF2CHBrF | |
| —CH2CH3 | H | H | H | CH | OCF2H | OCF2CF2H | |
| —CH2CH3 | H | H | H | CH | OCF2H | OCF2CHFCF3 | |
| —CH2CH3 | H | H | H | CH | CH3 | OCF2CF2H | |
| —CH2CH3 | H | H | H | N | OCF2H | CH2CH3 | |
| —CH2CH3 | H | H | H | N | OCF2H | CH2OCH3 | |
| —CH2CH3 | H | H | H | N | OCF2H | OCH2CF3 | |
| —CH2CH3 | H | H | H | N | OCF2H | NH2 | |
| —CH2CH3 | H | H | H | N | OCF2H | N(CH3)2 | |
| —CH2CH3 | H | H | H | N | OCF2H | OCF2CHBrF | |
| —CH2CH3 | H | H | H | N | OCF2H | OCF2CHFCF3 | |
| —CH2CH3 | H | H | H | N | OCF2H | OCF2H | |
| —CH2CH3 | H | H | H | N | CH3 | OCF2H | |

TABLE IVb

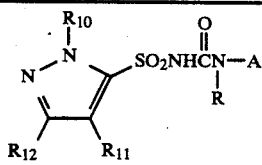

| R10 | R11 | R12 | R | A | Y' | m.p. (°C.) |
|---|---|---|---|---|---|---|
| CH2CH3 | H | H | H | A-2 | H | |
| CH2CH3 | H | H | H | A-2 | Cl | |
| CH2CH3 | H | H | H | A-2 | CH3 | |
| CH2CH3 | H | H | H | A-2 | OCH3 | |
| CH2CH3 | H | H | H | A-2 | OCF2H | |
| CH2CH3 | H | H | H | A-3 | H | |
| CH2CH3 | H | H | H | A-3 | Cl | |
| CH2CH3 | H | H | H | A-3 | CH3 | |

TABLE IVb-continued

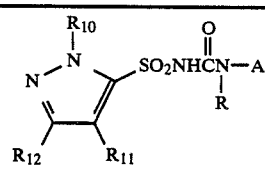

| R10 | R11 | R12 | R | A | Y' | m.p. (°C.) |
|---|---|---|---|---|---|---|
| CH2CH3 | H | H | H | A-3 | OCH3 | |
| CH2CH3 | H | H | H | A-3 | OCF2H | |
| CH2CH3 | H | H | H | A-4 | H | |
| CH2CH3 | H | H | H | A-4 | Cl | |
| CH2CH3 | H | H | H | A-4 | CH3 | |
| CH2CH3 | H | H | H | A-4 | OCH3 | |
| CH2CH3 | H | H | H | A-4 | OCF2H | |

TABLE IVc

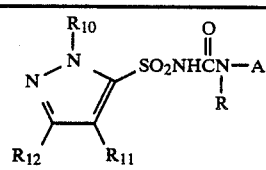

| R10 | R11 | R12 | R | A | X2 | Y2 | X3 | m.p. (°C.) |
|---|---|---|---|---|---|---|---|---|
| —CH2CH3 | H | H | H | A-5 | OCH3 | CH3 | — | |
| —CH2CH3 | H | H | H | A-5 | OCH3 | CH2CH3 | — | |
| —CH2CH3 | H | H | H | A-5 | OCH3 | CH2CF3 | — | |
| —CH2CH3 | H | H | H | A-5 | CH3 | CH3 | — | |
| —CH2CH3 | H | H | H | A-5 | CH3 | CH2CH3 | — | |
| —CH2CH3 | H | H | H | A-5 | CH3 | CH2CF3 | — | |
| —CH2CH3 | H | H | H | A-5 | CH2CH3 | CH3 | — | |
| —CH2CH3 | H | H | H | A-5 | CH2CH3 | CH2CH3 | — | |
| —CH2CH3 | H | H | H | A-5 | CH2CH3 | CH2CF3 | — | |
| —CH2CH3 | H | H | H | A-5 | OCH2CH3 | CH3 | — | |
| —CH2CH3 | H | H | H | A-5 | OCH2CH3 | CH2CH3 | — | |
| —CH2CH3 | H | H | H | A-5 | OCH2CH3 | CH2CF3 | — | |
| —CH2CH3 | H | H | H | A-5 | SCH3 | CH3 | — | |
| —CH2CH3 | H | H | H | A-5 | SCH3 | CH2CH3 | — | |
| —CH2CH3 | H | H | H | A-5 | SCH3 | CH2CF3 | — | |
| —CH2CH3 | H | H | H | A-5 | SCH2CH3 | CH3 | — | |
| —CH2CH3 | H | H | H | A-5 | SCH2CH3 | CH2CH3 | — | |
| —CH2CH3 | H | H | H | A-5 | SCH2CH3 | CH2CF3 | — | |
| —CH2CH3 | H | H | H | A-6 | — | — | OCH3 | |
| —CH2CH3 | H | H | H | A-6 | — | — | CH3 | |

TABLE Va

| $R_{11}$ | $R_{12}$ | R | Z | X | Y | m.p. (°C.) |
|---|---|---|---|---|---|---|
| H | H | H | CH | $CH_3$ | $OCH_3$ | |
| $CH_3$ | H | H | CH | $OCH_3$ | $OCH_3$ | |
| $CH_3CH_2$— | H | H | CH | $CH_3$ | $CH_3$ | |
| $CH_3CH_2CH_2$— | H | H | CH | Cl | $OCH_3$ | |
| $(CH_3)_2CH$— | H | H | N | $CH_3$ | $OCH_3$ | |
| F | H | H | N | $CH_3$ | $OCH_3$ | |
| Cl | H | H | N | $OCH_3$ | $OCH_3$ | |
| Br | H | H | N | $OCH_3$ | —$N(CH_3)_2$ | |
| $NO_2$ | H | H | N | $OCH_3$ | —$N(CH_3)_2$ | |
| $OCH_3$ | H | H | CH | $CH_3$ | $OCH_3$ | |
| —$OCH_2CH_3$ | H | H | N | $CH_3$ | $OCH_3$ | |
| —$OCH_2CH_2CH_3$ | H | H | N | $OCH_3$ | —$N(CH_3)_2$ | |
| —$OCH(CH_3)_2$ | H | H | CH | Cl | $OCH_3$ | |
| —$CO_2CH_3$ | H | H | CH | $OCH_3$ | $OCH_3$ | |
| —$CO_2CH_2CH_3$ | H | H | CH | $CH_3$ | $OCH_3$ | |
| —$CO_2CH_2CH_2CH_3$ | H | H | CH | $CH_3$ | $CH_3$ | |
| —$CO_2CH(CH_3)_2$ | H | H | CH | $OCH_3$ | $OCH_3$ | |
| —$CO_2CH_2CH=CH_2$ | H | H | CH | $CH_3$ | $OCH_3$ | |
| —$SCH_3$ | H | H | N | $OCH_3$ | $OCH_3$ | |
| —$SCH_2CH_3$ | H | H | N | $OCH_3$ | $OCH_3$ | |
| —$SCH_2CH_2CH_3$ | H | H | N | $OCH_3$ | $OCH_3$ | |
| —$SOCH_3$ | H | H | N | $OCH_3$ | $OCH_3$ | |
| —$CO_2CH_3$ | H | H | CH | $CH_3$ | $OCH_3$ | |
| —$CO_2CH_3$ | H | $CH_3$ | CH | $CH_3$ | $OCH_3$ | |
| —$CO_2CH_3$ | H | $CH_3$ | CH | $CH_3$ | $CH_3$ | |
| —$CO_2CH_3$ | H | $CH_3$ | CH | $OCH_3$ | $OCH_3$ | |
| —$CO_2CH_3$ | H | $CH_3$ | N | $OCH_3$ | $OCH_3$ | |
| —$CO_2CH_3$ | H | $CH_3$ | N | $CH_3$ | $OCH_3$ | |
| —$SO_2CH_3$ | H | H | CH | $CH_3$ | —$OCH_2CH_3$ | |
| —$SO_2CH_3$ | H | H | N | $OCH_3$ | $NH_2$ | |
| —$SO_2CH_3$ | H | H | N | $OCH_3$ | —$NHCH_3$ | |
| —$SO_2CH_3$ | H | H | N | $OCH_3$ | —$N(CH_3)_2$ | |
| —$SO_2CH_3$ | H | H | CH | $CH_3$ | —$CH_2OCH_3$ | |
| —$SO_2CH_3$ | H | H | CH | $CH_3$ | —$CH(OCH_3)_2$ | |
| —$SO_2CH_3$ | H | H | CH | $OCH_3$ | $OCH_3$ | |
| —$SO_2CH_2CH_3$ | H | H | CH | $OCH_3$ | $CH_3$ | |
| —$SO_2CH_2CH_2CH_3$ | H | H | N | $OCH_3$ | $OCH_3$ | |
| —$SO_2N(CH_3)_2$ | H | H | N | $CH_3$ | $OCH_3$ | |
| —$SO_2N(CH_3)(CH_2CH_3)$ | H | H | N | $OCH_3$ | —$N(CH_3)_2$ | |
| —$SO_2N(CH_2CH_3)_2$ | H | H | N | $OCH_3$ | $CH_3$ | |
| —$CO_2CH_3$ | $CH_3$ | H | CH | $CH_3$ | $OCH_3$ | |
| —$CO_2CH_3$ | H | H | CH | $CH_3$ | $CH_3$ | |
| —$CO_2CH_3$ | H | H | CH | $OCH_3$ | $OCH_3$ | |
| —$CO_2CH_3$ | H | H | CH | $CH_3$ | $OCH_3$ | |
| —$CO_2CH_3$ | H | H | N | $CH_3$ | $OCH_3$ | |
| —$CO_2CH_3$ | H | H | N | $OCH_3$ | $OCH_3$ | |
| —$CO_2CH_3$ | H | H | CH | $OCF_2H$ | $CH_3$ | |
| —$CO_2CH_3$ | H | H | CH | $OCF_2H$ | $OCH_3$ | |
| —$CO_2CH_3$ | H | H | N | $OCF_2H$ | $CH_3$ | |
| —$CO_2CH_3$ | H | H | CH | $SCF_2H$ | $CH_3$ | |
| —$CO_2CH_3$ | H | H | CH | $SCF_2H$ | $OCH_3$ | |
| —$CO_2CH_3$ | H | H | CH | $SCF_2H$ | $OCF_3$ | |
| —$CO_2CH_3$ | H | H | CH | $CH_3$ | $OCH_2CF_3$ | |
| —$CO_2CH_3$ | H | H | CH | $OCH_3$ | $OCH_2CF_3$ | |
| —$CO_2CH_3$ | H | H | CH | $CH_3$ | $OCF_3$ | |
| —$CO_2CH_3$ | H | H | CH | $OCH_3$ | $OCF_3$ | |
| —$CO_2CH_3$ | H | H | N | $CH_3$ | $OCF_3$ | |
| —$CO_2CH_3$ | H | H | CH | $CH_3$ | $OCF_2CHClF$ | |
| —$CO_2CH_3$ | H | H | CH | $CH_3$ | $OCF_2CF_2H$ | |
| —$CO_2CH_3$ | H | H | CH | $OCH_3$ | $OCF_2CF_2H$ | |
| —$CO_2CH_3$ | H | H | N | $CH_3$ | $OCF_2CF_2H$ | |
| —$CO_2CH_3$ | H | H | CH | $CH_3$ | $OCF_2CHFCF_3$ | |
| —$CO_2CH_3$ | H | H | CH | $OCH_3$ | $OCF_2CHFCF_3$ | |
| —$CO_2CH_3$ | H | H | CH | $OCF_2H$ | $CH_2CH_3$ | |
| —$CO_2CH_3$ | H | H | CH | $OCF_2H$ | $OCH_2CH_3$ | |
| —$CO_2CH_3$ | H | H | CH | $OCF_2H$ | $CH_2OCH_3$ | |
| —$CO_2CH_3$ | H | H | CH | $OCF_2H$ | $CH(OCH_3)_2$ | |
| —$CO_2CH_3$ | H | H | CH | $OCF_2H$ | $OCH_2CF_3$ | |
| —$CO_2CH_3$ | H | H | CH | $OCF_2H$ | $OCF_3$ | |
| —$CO_2CH_3$ | H | H | CH | $OCF_2H$ | $NH_2$ | |
| —$CO_2CH_3$ | H | H | CH | $OCF_2H$ | $NHCH_3$ | |

TABLE Va-continued

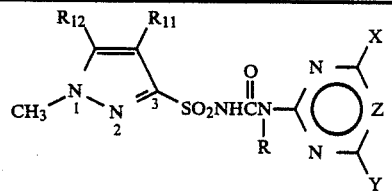

| R11 | R12 | R | Z | X | Y | m.p. (°C.) |
|---|---|---|---|---|---|---|
| —CO2CH3 | H | H | CH | OCF2H | N(CH3)2 | |
| —CO2CH3 | H | H | CH | OCF2H | OCF2H | |
| —CO2CH3 | H | H | CH | OCF2H | OCF2CHClF | |
| —CO2CH3 | H | H | CH | OCF2H | OCF2CHBrF | |
| —CO2CH3 | H | H | CH | OCF2H | OCF2CF2H | |
| —CO2CH3 | H | H | CH | OCF2H | OCF2CHFCF3 | |
| —CO2CH3 | H | H | CH | CH3 | OCF2CF2H | |
| —CO2CH3 | H | H | N | OCF2H | CH2CH3 | |
| —CO2CH3 | H | H | N | OCF2H | CH2OCH3 | |
| —CO2CH3 | H | H | N | OCF2H | OCH2CF3 | |
| —CO2CH3 | H | H | N | OCF2H | NH2 | |
| —CO2CH3 | H | H | N | OCF2H | N(CH3)2 | |
| —CO2CH3 | H | H | N | OCF2H | OCF2CHBrF | |
| —CO2CH3 | H | H | N | OCF2H | OCF2CHFCF3 | |
| —CO2CH3 | H | H | N | OCF2H | OCF2H | |
| —CO2CH3 | H | H | N | CH3 | OCF2H | |

TABLE Vb

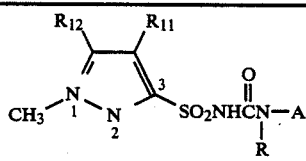

| R11 | R12 | R | A | Y' | m.p. (°C.) |
|---|---|---|---|---|---|
| CO2CH3 | H | H | A-2 | H | |
| CO2CH3 | H | H | A-2 | Cl | |
| CO2CH3 | H | H | A-2 | CH3 | |
| CO2CH3 | H | H | A-2 | OCH3 | |
| CO2CH3 | H | H | A-2 | OCF2H | |
| CO2CH3 | H | H | A-3 | H | |
| CO2CH3 | H | H | A-3 | Cl | |
| CO2CH3 | H | H | A-3 | CH3 | |

TABLE Vb-continued

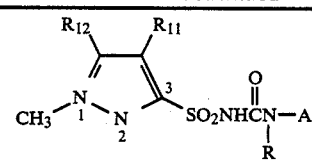

| R11 | R12 | R | A | Y' | m.p. (°C.) |
|---|---|---|---|---|---|
| CO2CH3 | H | H | A-3 | OCH3 | |
| CO2CH3 | H | H | A-3 | OCF2H | |
| CO2CH3 | H | H | A-4 | H | |
| CO2CH3 | H | H | A-4 | Cl | |
| CO2CH3 | H | H | A-4 | CH3 | |
| CO2CH3 | H | H | A-4 | OCH3 | |
| CO2CH3 | H | H | A-4 | OCF2H | |

TABLE Vc

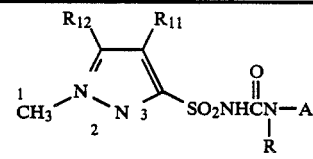

| R11 | R12 | R | A | X2 | Y2 | X3 | m.p.(°C.) |
|---|---|---|---|---|---|---|---|
| —CO2CH3 | H | H | A-5 | OCH3 | CH3 | — | |
| —CO2CH3 | H | H | A-5 | OCH3 | CH2CH3 | — | |
| —CO2CH3 | H | H | A-5 | OCH3 | CH2CF3 | — | |
| —CO2CH3 | H | H | A-5 | CH3 | CH3 | — | |
| —CO2CH3 | H | H | A-5 | CH3 | CH2CH3 | — | |
| —CO2CH3 | H | H | A-5 | CH3 | CH2CF3 | — | |
| —CO2CH3 | H | H | A-5 | CH2CH3 | CH3 | — | |
| —CO2CH3 | H | H | A-5 | CH2CH3 | CH2CH3 | — | |
| —CO2CH3 | H | H | A-5 | CH2CH3 | CH2CF3 | — | |
| —CO2CH3 | H | H | A-5 | OCH2CH3 | CH3 | — | |
| —CO2CH3 | H | H | A-5 | OCH2CH3 | CH2CH3 | — | |
| —CO2CH3 | H | H | A-5 | OCH2CH3 | CH2CF3 | — | |
| —CO2CH3 | H | H | A-5 | SCH3 | CH3 | — | |
| —CO2CH3 | H | H | A-5 | SCH3 | CH2CH3 | — | |
| —CO2CH3 | H | H | A-5 | SCH3 | CH2CF3 | — | |
| —CO2CH3 | H | H | A-5 | SCH2CH3 | CH3 | — | |
| —CO2CH3 | H | H | A-5 | SCH2CH3 | CH2CH3 | — | |
| —CO2CH3 | H | H | A-5 | SCH2CH3 | CH2CF3 | — | |
| —CO2CH3 | H | H | A-6 | — | — | OCH3 | |

TABLE Vc-continued

Structure: 1-methyl pyrazole with $R_{12}$ at position 4, $R_{11}$ at position 5 (on pyrazole ring numbered N1(CH3)-N2-C3), with C3 bearing $SO_2NHC(O)N(R)-A$

| $R_{11}$ | $R_{12}$ | R | A | $X^2$ | $Y^2$ | $X^3$ | m.p.(°C.) |
|---|---|---|---|---|---|---|---|
| —CO$_2$CH$_3$ | H | H | A-6 | — | — | CH$_3$ | |

TABLE VIa

Structure: pyrazole (N1-N2(R15)-C3(R14)=C4-C5(R13)) with C4 bearing $SO_2NHC(O)N(R)$– heterocycle containing N, Z, with substituents X and Y.

| $R_{13}$ | $R_{14}$ | $R_{15}$ | R | Z | X | Y | m.p.(°C.) |
|---|---|---|---|---|---|---|---|
| H | H | H | H | CH | CH$_3$ | OCH$_3$ | |
| CH$_3$— | H | H | H | CH | CH$_3$ | OCH$_3$ | |
| CH$_3$CH$_2$— | CH$_3$ | H | H | CH | CH$_3$ | OCH$_3$ | |
| CH$_3$CH$_2$CH$_2$— | H | H | H | CH | CH$_3$ | OCH$_3$ | |
| (CH$_3$)$_2$CH— | CH$_3$ | H | H | CH | CH$_3$ | OCH$_3$ | |
| CH$_3$O— | H | H | H | CH | CH$_3$ | OCH$_3$ | |
| CH$_3$CH$_2$O— | CH$_3$ | H | H | CH | CH$_3$ | OCH$_3$ | |
| CH$_3$CH$_2$CH$_2$O— | H | H | H | CH | CH$_3$ | OCH$_3$ | |
| F | H | H | H | CH | CH$_3$ | OCH$_3$ | |
| Cl | H | H | H | CH | CH$_3$ | OCH$_3$ | |
| Br | H | H | H | CH | CH$_3$ | OCH$_3$ | |
| NO$_2$ | H | H | H | CH | CH$_3$ | OCH$_3$ | |
| —CO$_2$CH$_3$ | H | H | H | CH | CH$_3$ | OCH$_3$ | |
| —CO$_2$CH$_2$CH$_3$ | H | H | H | CH | CH$_3$ | OCH$_3$ | |
| —CO$_2$CH$_2$CH$_2$CH$_3$ | H | H | H | CH | CH$_3$ | OCH$_3$ | |
| —CO$_2$CH$_2$CH=CH$_2$ | H | H | H | CH | CH$_3$ | OCH$_3$ | |
| —SCH$_3$ | H | H | H | CH | CH$_3$ | OCH$_3$ | |
| —SCH$_2$CH$_3$ | H | H | H | CH | CH$_3$ | OCH$_3$ | |
| —SCH$_2$CH$_2$CH$_3$ | H | H | H | CH | CH$_3$ | OCH$_3$ | |
| —SOCH$_3$ | H | H | H | CH | CH$_3$ | OCH$_3$ | |
| —SO$_2$CH$_3$ | H | H | H | CH | CH$_3$ | OCH$_3$ | |
| —SO$_2$CH$_2$CH$_3$ | H | H | H | CH | CH$_3$ | OCH$_3$ | |
| —SO$_2$CH$_2$CH$_2$CH$_3$ | H | H | H | CH | CH$_3$ | OCH$_3$ | |
| —SO$_2$N(CH$_3$)$_2$ | H | H | H | CH | CH$_3$ | OCH$_3$ | |
| —SO$_2$N(CH$_3$)(CH$_2$CH$_3$) | H | H | H | CH | CH$_3$ | OCH$_3$ | |
| —SO$_2$N(CH$_2$CH$_3$)$_2$ | H | H | H | CH | CH$_3$ | OCH$_3$ | |
| —CO$_2$CH$_3$ | H | H | H | CH | OCH$_3$ | OCH$_3$ | |
| —CO$_2$CH$_3$ | H | H | H | CH | CH$_3$ | CH$_3$ | |
| —CO$_2$CH$_3$ | H | H | H | CH | Cl | OCH$_3$ | |
| —CO$_2$CH$_3$ | H | H | H | CH | Cl | NH$_2$ | |
| —CO$_2$CH$_3$ | H | H | H | N | OCH$_3$ | OCH$_3$ | |
| —CO$_2$CH$_3$ | H | H | H | N | OCH$_3$ | CH$_3$ | |
| —CO$_2$CH$_3$ | H | H | H | N | OCH$_3$ | —NHCH$_3$ | |
| —CO$_2$CH$_3$ | H | H | H | N | OCH$_3$ | —N(CH$_3$)$_2$ | |
| —SO$_2$CH$_3$ | H | H | H | CH | OCH$_3$ | OCH$_3$ | |
| —SO$_2$CH$_3$ | H | H | H | CH | CH$_3$ | CH$_3$ | |
| —SO$_2$CH$_3$ | H | H | H | CH | Cl | OCH$_3$ | |
| —SO$_2$CH$_3$ | H | H | H | CH | Cl | NH$_2$ | |
| —SO$_2$CH$_3$ | H | H | H | N | CH$_3$ | CH$_3$ | |
| —SO$_2$CH$_3$ | H | H | H | N | OCH$_3$ | OCH$_3$ | |
| —SO$_2$CH$_3$ | H | H | H | N | CH$_3$ | OCH$_3$ | |
| —SO$_2$CH$_3$ | H | H | H | N | OCH$_3$ | NH$_2$ | |
| —SO$_2$N(CH$_3$)$_2$ | H | H | H | CH | OCH$_3$ | OCH$_3$ | |
| —SO$_2$N(CH$_3$)$_2$ | H | H | H | CH | CH$_3$ | CH$_3$ | |
| —SO$_2$N(CH$_3$)$_2$ | H | H | H | CH | Cl | OCH$_3$ | |
| —SO$_2$N(CH$_3$)$_2$ | H | H | H | CH | Cl | NH$_2$ | |
| —SO$_2$N(CH$_3$)$_2$ | H | H | H | N | CH$_3$O | —NHCH$_3$ | |
| —SO$_2$N(CH$_3$)$_2$ | H | H | H | N | CH$_3$O | —N(CH$_3$)$_2$ | |
| —SO$_2$N(CH$_3$)$_2$ | H | H | H | N | CH$_3$O | OCH$_3$ | |
| —SO$_2$N(CH$_3$)$_2$ | H | H | H | N | CH$_3$ | OCH$_3$ | |
| CH$_3$ | H | CH$_3$ | H | CH | CH$_3$ | OCH$_3$ | 207–210 |
| CH$_3$CH$_2$— | H | CH$_3$ | H | N | CH$_3$ | OCH$_3$ | |
| CH$_3$ | CH$_3$ | H | H | N | CH$_3$ | OCH$_3$ | |
| CH$_3$ | Cl | H | H | N | CH$_3$ | OCH$_3$ | |
| Cl | Cl | H | H | N | CH$_3$ | OCH$_3$ | |
| NO$_2$ | Cl | H | H | N | CH$_3$ | OCH$_3$ | |

TABLE VIa-continued

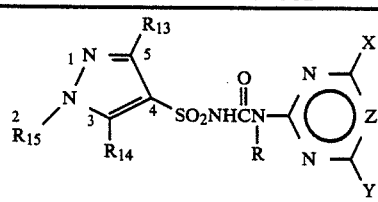

| $R_{13}$ | $R_{14}$ | $R_{15}$ | R | Z | X | Y | m.p.(°C.) |
|---|---|---|---|---|---|---|---|
| H | CH$_3$ | CH$_3$ | H | CH | CH$_3$ | OCH$_3$ | 179–181 |
| H | CH$_3$CH$_2$— | CH$_3$ | H | CH | CH$_3$ | OCH$_3$ | |
| H | CH$_3$CH$_2$CH$_2$— | CH$_3$ | H | CH | CH$_3$ | OCH$_3$ | |
| H | (CH$_3$)$_2$CH— | CH$_3$ | H | CH | CH$_3$ | OCH$_3$ | |
| H | —OCH$_3$ | CH$_3$ | H | CH | CH$_3$ | OCH$_3$ | |
| H | —OCH$_2$CH$_3$ | CH$_3$ | H | CH | CH$_3$ | OCH$_3$ | |
| H | —OCH$_2$CH$_2$CH$_3$ | CH$_3$ | H | CH | OCH$_3$ | OCH$_3$ | |
| H | F | CH$_3$ | H | CH | CH$_3$ | CH$_3$ | |
| H | Cl | CH$_3$ | H | CH | CH$_3$ | OCH$_3$ | |
| H | Br | CH$_3$ | H | CH | OCH$_3$ | OCH$_3$ | |
| H | NO$_2$ | CH$_3$ | H | CH | CH$_3$ | CH$_3$ | |
| H | —CO$_2$CH$_3$ | CH$_3$ | H | CH | OCH$_3$ | OCH$_3$ | |
| H | —CO$_2$CH$_2$CH$_3$ | CH$_3$ | H | CH | OCH$_3$ | CH$_3$ | |
| H | —SO$_2$CH$_3$ | CH$_3$ | H | N | OCH$_3$ | OCH$_3$ | |
| H | —SO$_2$CH$_2$CH$_3$ | CH$_3$ | H | N | CH$_3$ | OCH$_3$ | |
| H | —SO$_2$CH$_2$CH$_2$CH$_3$ | CH$_3$ | H | N | CH$_3$ | OCH$_3$ | |
| H | —SO$_2$N(CH$_3$)$_2$ | CH$_3$ | H | N | CH$_3$ | OCH$_3$ | |
| H | —SO$_2$(CH$_3$) | CH$_3$ | H | N | CH$_3$ | OCH$_3$ | |
| —CO$_2$CH$_3$ | H | H | CH$_3$ | CH | CH$_3$ | CH$_3$ | |
| —CO$_2$CH$_3$ | H | H | CH$_3$ | CH | CH$_3$ | OCH$_3$ | |
| —CO$_2$CH$_3$ | H | H | CH$_3$ | CH | OCH$_3$ | OCH$_3$ | |
| —CO$_2$CH$_3$ | H | H | CH$_3$ | N | OCH$_3$ | OCH$_3$ | |
| —CO$_2$CH$_3$ | H | H | CH$_3$ | N | OCH$_3$ | —N(CH$_3$)$_2$ | |
| —CO$_2$CH$_3$ | H | H | CH$_3$ | N | CH$_3$ | OCH$_3$ | |
| —CO$_2$CH$_3$ | H | H | CH$_3$ | N | CH$_3$ | CH$_3$ | |
| —SO$_2$CH$_3$ | H | H | H | CH | Cl | —NH$_2$ | |
| —SO$_2$CH$_3$ | H | H | H | CH | Cl | —NHCH$_3$ | |
| —SO$_2$CH$_3$ | H | H | H | N | CH$_3$ | —OCH$_2$CH$_3$ | |
| —SO$_2$CH$_3$ | H | H | H | N | CH$_3$ | —CH$_2$OCH$_3$ | |
| —SO$_2$CH$_3$ | H | H | H | N | CH$_3$ | —CH(OCH$_3$)$_2$ | |
| —CO$_2$CH$_3$ | H | H | H | CH | OCF$_2$H | CH$_3$ | |
| —CO$_2$CH$_3$ | H | H | H | CH | OCF$_2$H | OCH$_3$ | |
| —CO$_2$CH$_3$ | H | H | H | N | OCF$_2$H | CH$_3$ | |
| —CO$_2$CH$_3$ | H | H | H | CH | SCF$_2$H | CH$_3$ | |
| —CO$_2$CH$_3$ | H | H | H | CH | SCF$_2$H | OCH$_3$ | |
| —CO$_2$CH$_3$ | H | H | H | CH | SCF$_2$H | OCF$_3$ | |
| —CO$_2$CH$_3$ | H | H | H | CH | CH$_3$ | OCH$_2$CF$_3$ | |
| —CO$_2$CH$_3$ | H | H | H | CH | OCH$_3$ | OCH$_2$CF$_3$ | |
| —CO$_2$CH$_3$ | H | H | H | CH | CH$_3$ | OCF$_3$ | |
| —CO$_2$CH$_3$ | H | H | H | CH | OCH$_3$ | OCF$_3$ | |
| —CO$_2$CH$_3$ | H | H | H | N | CH$_3$ | OCF$_3$ | |
| —CO$_2$CH$_3$ | H | H | H | CH | CH$_3$ | OCF$_2$CHClF | |
| —CO$_2$CH$_3$ | H | H | H | CH | CH$_3$ | OCF$_2$CF$_2$H | |
| —CO$_2$CH$_3$ | H | H | H | CH | OCH$_3$ | OCF$_2$CF$_2$H | |
| —CO$_2$CH$_3$ | H | H | H | N | CH$_3$ | OCF$_2$CF$_2$H | |
| —CO$_2$CH$_3$ | H | H | H | CH | CH$_3$ | OCF$_2$CHFCF$_3$ | |
| —CO$_2$CH$_3$ | H | H | H | CH | OCH$_3$ | OCF$_2$CHFCF$_3$ | |
| —CO$_2$CH$_3$ | H | H | H | CH | OCF$_2$H | CH$_2$CH$_3$ | |
| —CO$_2$CH$_3$ | H | H | H | CH | OCF$_2$H | OCH$_2$CH$_3$ | |
| —CO$_2$CH$_3$ | H | H | H | CH | OCF$_2$H | CH$_2$OCH$_3$ | |
| —CO$_2$CH$_3$ | H | H | H | CH | OCF$_2$H | CH(OCH$_3$)$_2$ | |
| —CO$_2$CH$_3$ | H | H | H | CH | OCF$_2$H | OCH$_2$CF$_3$ | |
| —CO$_2$CH$_3$ | H | H | H | CH | OCF$_2$H | OCF$_3$ | |
| —CO$_2$CH$_3$ | H | H | H | CH | OCF$_2$H | NH$_2$ | |
| —CO$_2$CH$_3$ | H | H | H | CH | OCF$_2$H | NHCH$_3$ | |
| —CO$_2$CH$_3$ | H | H | H | CH | OCF$_2$H | N(CH$_3$)$_2$ | |
| —CO$_2$CH$_3$ | H | H | H | CH | OCF$_2$H | OCF$_2$H | |
| —CO$_2$CH$_3$ | H | H | H | CH | OCF$_2$H | OCF$_2$CHClF | |
| —CO$_2$CH$_3$ | H | H | H | CH | OCF$_2$H | OCF$_2$CHBrF | |
| —CO$_2$CH$_3$ | H | H | H | CH | OCF$_2$H | OCF$_2$CF$_2$H | |
| —CO$_2$CH$_3$ | H | H | H | CH | OCF$_2$H | OCF$_2$CHFCF$_3$ | |
| —CO$_2$CH$_3$ | H | H | H | CH | CH$_3$ | OCF$_2$CF$_2$H | |
| —CO$_2$CH$_3$ | H | H | H | N | OCF$_2$H | CH$_2$CH$_3$ | |
| —CO$_2$CH$_3$ | H | H | H | N | OCF$_2$H | CH$_2$OCH$_3$ | |
| —CO$_2$CH$_3$ | H | H | H | N | OCF$_2$H | OCH$_2$CF$_3$ | |
| —CO$_2$CH$_3$ | H | H | H | N | OCF$_2$H | NH$_2$ | |
| —CO$_2$CH$_3$ | H | H | H | N | OCF$_2$H | N(CH$_3$)$_2$ | |
| —CO$_2$CH$_3$ | H | H | H | N | OCF$_2$H | OCF$_2$CHBrF | |
| —CO$_2$CH$_3$ | H | H | H | N | OCF$_2$H | OCF$_2$CHFCF$_3$ | |
| —CO$_2$CH$_3$ | H | H | H | N | OCF$_2$H | OCF$_2$H | |
| —CO$_2$CH$_3$ | H | H | H | N | CH$_3$ | OCF$_2$H | |

TABLE VIa-continued

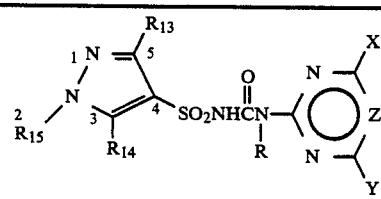

| R13 | R14 | R15 | R | Z | X | Y | m.p.(°C.) |
|---|---|---|---|---|---|---|---|
| —H | CH3 | CH3 | H | CH | OCH3 | OCH3 | 207–210° |
| —H | CH3 | CH3 | H | CH | CH3 | CH3 | 204–208° |
| —H | CH3 | CH3 | H | N | CH3 | OCH3 | 197–201° |
| —H | CH3 | CH3 | H | N | OCH3 | OCH3 | 174–179° |
| —H | CH3 | CH3 | H | N | CH3 | CH3 | 211–215° |
| —CH3 | H | CH3 | H | CH | OCH3 | OCH3 | 189–191° |
| —CH3 | H | CH3 | H | CH | CH3 | CH3 | 210–215° |
| —CH3 | H | CH3 | H | N | CH3 | OCH3 | 183–186° |
| —CH3 | H | CH3 | H | N | OCH3 | OCH3 | 187–189° |
| —CH3 | H | CH3 | H | N | CH3 | CH3 | 225–226° |

TABLE VIb

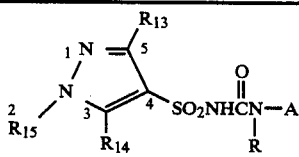

| R13 | R14 | R15 | R | A | Y' | m.p.(°C.) |
|---|---|---|---|---|---|---|
| CO2CH3 | H | H | H | A-2 | H | |
| CO2CH3 | H | H | H | A-2 | Cl | |
| CO2CH3 | H | H | H | A-2 | CH3 | |
| CO2CH3 | H | H | H | A-2 | OCH3 | |
| CO2CH3 | H | H | H | A-2 | OCF2H | |
| CO2CH3 | H | H | H | A-3 | H | |
| CO2CH3 | H | H | H | A-3 | Cl | |
| CO2CH3 | H | H | H | A-3 | CH3 | |
| CO2CH3 | H | H | H | A-3 | OCH3 | |
| CO2CH3 | H | H | H | A-3 | OCF2H | |
| CO2CH3 | H | H | H | A-4 | H | |
| CO2CH3 | H | H | H | A-4 | Cl | |
| CO2CH3 | H | H | H | A-4 | CH3 | |
| CO2CH3 | H | H | H | A-4 | OCH3 | |

TABLE VIb-continued

| R13 | R14 | R15 | R | A | Y' | m.p.(°C.) |
|---|---|---|---|---|---|---|
| CO2CH3 | H | H | H | A-4 | OCF2H | |

TABLE VIc

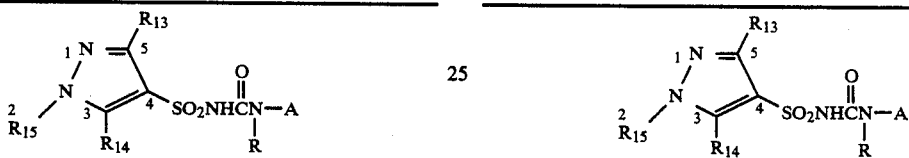

| R13 | R14 | R15 | R | A | X² | Y² | X³ | m.p.(°C.) |
|---|---|---|---|---|---|---|---|---|
| —CO2CH3 | H | H | H | A-5 | OCH3 | CH3 | — | |
| —CO2CH3 | H | H | H | A-5 | OCH3 | CH2CH3 | — | |
| —CO2CH3 | H | H | H | A-5 | OCH3 | CH2CF3 | — | |
| —CO2CH3 | H | H | H | A-5 | CH3 | CH3 | — | |
| —CO2CH3 | H | H | H | A-5 | CH3 | CH2CH3 | — | |
| —CO2CH3 | H | H | H | A-5 | CH3 | CH2CF3 | — | |
| —CO2CH3 | H | H | H | A-5 | CH2CH3 | CH3 | — | |
| —CO2CH3 | H | H | H | A-5 | CH2CH3 | CH2CH3 | — | |
| —CO2CH3 | H | H | H | A-5 | CH2CH3 | CH2CF3 | — | |
| —CO2CH3 | H | H | H | A-5 | OCH2CH3 | CH3 | — | |
| —CO2CH3 | H | H | H | A-5 | OCH2CH3 | CH2CH3 | — | |
| —CO2CH3 | H | H | H | A-5 | OCH2CH3 | CH2CF3 | — | |
| —CO2CH3 | H | H | H | A-5 | SCH3 | CH3 | — | |
| —CO2CH3 | H | H | H | A-5 | SCH3 | CH2CH3 | — | |
| —CO2CH3 | H | H | H | A-5 | SCH3 | CH2CF3 | — | |
| —CO2CH3 | H | H | H | A-5 | SCH2CH3 | CH3 | — | |
| —CO2CH3 | H | H | H | A-5 | SCH2CH3 | CH2CH3 | — | |
| —CO2CH3 | H | H | H | A-5 | SCH2CH3 | CH2CF3 | — | |
| —CO2CH3 | H | H | H | A-6 | — | — | OCH3 | |
| —CO2CH3 | H | H | H | A-6 | — | — | CH3 | |

FORMULATIONS

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid diluent(s). More specifically, they will contain these ingredients in the following approximate proportions:

TABLE VII

|  | Weight Percent* | | |
| --- | --- | --- | --- |
|  | Active Ingredient | Diluent(s) | Surfactant(s) |
| Wettable Powders | 20–90 | 0–74 | 1–10 |
| Oil Suspensions, Emulsions, Solutions, (including Emulsifiable Concentrates) | 3–50 | 40–95 | 0–15 |
| Aqueous Suspension | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, New Jersey, as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", Chemical Engineering, Dec. 4, 1967, pp. 147ff. and "Perry's Chemical Engineer's Handbook", 5th Ed., McGraw-Hill, New York, 1973, pp. 8–57ff.

For further information regarding the art of formulation, see for example:

H. M. Loux, U.S. Pat. No. 3,235,361, February 15, 1966, Col. 6, line 16 through Col. 7, line 19 and Examples 10 through 41;

R. W. Luckenbaugh, U.S. Pat. No. 3,309,192, March 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knusli, U.S. Pat. No. 2,891,855, June 23, 1959, Col. 3, line 66 through Col. 5, line 17 and Examples 1–4;

G. C. Klingman, "Weed Control as a Science", John Wiley and Sons, Inc., New York, 1961, pp. 81–96; and J. D. Fryer and S. A. Evans, "Weed Control Handbook", 5th Ed., Blackwell Scientific Publications, Oxford, 1968, pp. 101–103.

In the following examples, all parts are by weight unless otherwise indicated.

EXAMPLE 9

| Wettable Powder | |
| --- | --- |
| N-[(4,6-dimethylpyrimidin-2-yl)aminocarbonyl]-1-(1-methylethyl)-1H-imidazole-2-sulfonamide | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns, reblended, and packaged.

EXAMPLE 10

| Wettable Powder | |
| --- | --- |
| N-[(4-methoxy-6-methylpyrimidin-2-yl)aminocarbonyl]-1-(1-methylethyl)-1H-imidazole-2-sulfonamide | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

EXAMPLE 11

| Granule | |
| --- | --- |
| Wettable Powder of Example 10 | 5% |
| attapulgite granules (U.S.S. 20–40 mesh; 0.84–0.42 mm) | 95% |

A slurry of wettable powder containing ≈25% solids is sprayed on the surface of attapulgite granules in a double-cone blender. The granules are dried and packaged.

EXAMPLE 12

| Extruded Pellet | |
| --- | --- |
| N-[(4,6-dimethoxypyrimidin-2-yl)aminocarbonyl]-1-(1-methylethyl)-1H-imidazole-2-sulfonamide | 25% |
| anhydrous sodium sulfate | 10% |
| crude calcium ligninsulfonate | 5% |

| Extruded Pellet | |
|---|---|
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S. Ser. No. 20 sieve (0.84 mm openings). The granules held on a U.S. Ser. No. 40 sieve (0.42 mm openings) may be packaged for use and the fines recycled.

EXAMPLE 13

| Oil Suspension | |
|---|---|
| N-[(4,6-dimethylpyrimidin-2-yl)aminocarbonyl]-1-ethyl-1H-imidazole-2-sulfonamide | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 14

| Wettable Powder | |
|---|---|
| N-[(4-methoxy-6-methylpyrimidin-2-yl)aminocarbonyl]-1-ethyl-1H-imidazole-2-sulfonamide | 20% |
| sodium alkylnapthalenesulfonate | 4% |
| sodium ligninsulfonate | 4% |
| low viscosity methyl cellulose | 3% |
| attapulgite | 69% |

The ingredients are thoroughly blended. After grinding in a hammer-mill to produce particles essentially all below 100 microns, the material is reblended and sifted through a U.S. Ser. No. 50 sieve (0.3 mm opening) and packaged.

EXAMPLE 15

| Low Strength Granule | |
|---|---|
| N-[(4,6-dimethoxypyrimidin-2-yl)aminocarbonyl]-1-ethyl-1H-imidazole-2-sulfonamide | 1% |
| N,N-dimethylformamide | 9% |
| attapulgite granules (U.S.S. 20–40 sieve) | 90% |

The active ingredient is dissolved in the solvent and the solution is sprayed upon dedusted granules in a double cone blender. After spraying of the solution has been completed, the blender is allowed to run for a short period and then the granules are packaged.

EXAMPLE 16

| Aqueous Suspension | |
|---|---|
| N-[4,6-dimethylpyrimidin-2-yl)aminocarbonyl]-1- | 40% |
| (1-methylethyl)-1H-imidazole-2-sulfonamide | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE 17

| Solution | |
|---|---|
| N-[(4-methoxy-6-methylpyrimidin-2-yl)aminocarbonyl]-1-(1-methylethyl)-1H-imidazole-2-sulfonamide, sodium salt | 5% |
| water | 95% |

The salt is added directly to the water with stirring to produce the solution, which may then be packaged for use.

EXAMPLE 18

| Low Strength Granule | |
|---|---|
| N-[(4,6-dimethoxypyrimidin-2-yl)aminocarbonyl]-1-(1-methylethyl)-1H-imidazole-2-sulfonamide | 0.1% |
| attapulgite granules (U.S.S. 20–40 mesh) | 99.9% |

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 19

| Granule | |
|---|---|
| N-[(4,6-dimethylpyrimidin-2-yl)aminocarbonyl]-1-ethyl-1H-imidazole-2-sulfonamide | 80% |
| wetting agent | 1% |
| crude ligninsulfonate salt (containing 5–20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14–100 mesh (1410–149 microns), and packaged for use.

EXAMPLE 20

| High Strength Concentrate | |
|---|---|
| N-[(4-methoxy-6-methylpyrimidin-2-yl)aminocarbonyl]-1-ethyl-1H-imidazole-2-sulfonamide | 99% |
| silica aerogel | 0.5% |
| synthetic amorphous silica | 0.5% |

The ingredients are blended and ground in a hammer-mill to produce a material essentially all passing a U.S. Ser. No. 50 screen (0.3 mm opening). The concentrate may be formulated further if necessary.

EXAMPLE 21

| Wettable Powder | |
|---|---|
| N-[(4,6-dimethoxypyrimidin-2-yl)aminocarbonyl]-1-ethyl-1H-imidazole-2-sulfonamide | 90% |
| dioctyl sodium sulfosuccinate | 0.1% |
| synthetic fine silica | 9.9% |

The ingredients are blended and ground in a hammer-mill to produce particles essentially all below 100 microns. The material is sifted through a U.S. Ser. No. 50 screen and then packaged.

EXAMPLE 22

| Wettable Powder | |
|---|---|
| N-[(4,6-dimethylpyrimidin-2-yl)aminocarbonyl]-1-(1-methylethyl)-1H-imidazole-2-sulfonamide | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

EXAMPLE 23

| Oil Suspension | |
|---|---|
| N-[(4-methoxy-6-methylpyrimidin-2-yl)aminocarbonyl]-1-(1-methylethyl)-1H-imidazole-2-sulfonamide | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

UTILITY

Test results indicate that the compounds of the present invention are powerful herbicides. Many of them have utility for broad-spectrum pre- and/or post-emergence weed control in areas where complete control of all vegetation is desired, such as around fuel storage tanks, ammunition depots, industrial storage areas, parking lots, drive-in theaters, around billboards, highway and railroad structures. Alternatively, the subject compounds should be useful to modify plant growth.

The rates of application for the compounds of the invention are determined by a number of factors, including their use as plant growth modifiers or as herbicides, the crop species involved, the types of weeds to be controlled, weather and climate, formulations selected, mode of application, amount of foliage present etc. In general terms, the subject compounds should be applied at levels of around 0.02 to 10 kg/ha, the lower rates being suggested for use on lighter soils and/or those having a low organic matter content, for plant growth modification or for situations where only short-term persistence is required.

The compounds of the invention may be used in combination with any other commerical herbicide, examples of which are those of the triazine, triazole, uracil, urea, amide, diphenylether, carbamate and bipyridylium types.

The herbicidal properties of the subject compounds were discovered in a number of greenhouse tests. The test procedures and results follow.

Although some of the compounds do not exhibit a high degree of activity at the rate tested, it is expected that these compounds will exhibit herbicidal effects at higher rates.

TEST A

Seeds of crabgrass (Digitaria sp.), barnyard-grass (Echinochloa crusgalli), wild oats (Avena fatua), sicklepod (Cassia obtusifolia), morningglory (Ipomoea sp.), cocklebur (Xanthium sp.), sorghum, corn, soybean, rice, wheat and nutsedge tubers (Cyperus rotundus) were planted in a growth medium and treated pre-emergence with the chemicals dissolved in a nonphytotoxic solvent. At the same time, cotton having five leaves (including cotyledonary ones), bush beans with the third trifoliolate leaf expanding, crabgrass, barnyard-grass and wild oats with two leaves, sicklepod with three leaves (including cotyledonary ones), morningglory and cocklebur with four leaves (including the cotyledonary ones), sorghum and corn with four leaves, soybean with two cotyledonary leaves, rice with three leaves, wheat with one leaf, and nutsedge with three to five leaves were sprayed. Treated plants and controls were maintained in a greenhouse for sixteen days, whereupon all species were compared to controls and visually rated for response to treatment. The ratings are based on a numerical scale extending from 0=no injury, to 10=complete kill. The accompanying descriptive symbols have the following meanings:

C=chlorosis/necrosis;
D=defoliation;
E=emergence inhibition;
G=growth retardation;
H=formative effects;
U=unusual pigmentation;
X=axillary stimulation; and
6Y=abscised buds or flowers.

The ratings for the compounds tested by this procedure are presented in Table A. It will be seen that, at the low rates of application selected for this test, the compounds tested have utility for plant growth modification, and also are highly active herbicides.

Compounds
Compound 1
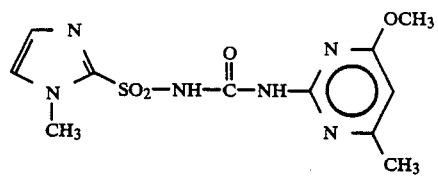
Compound 2
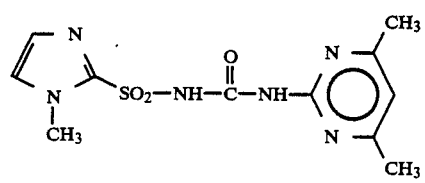
Compound 3
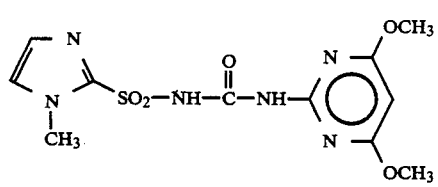
Compound 4
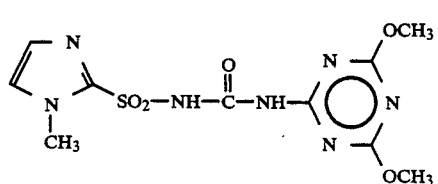
Compound 5
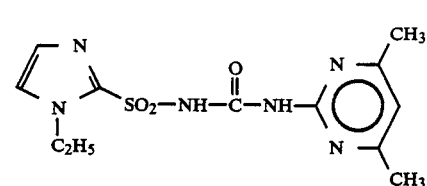
Compound 6
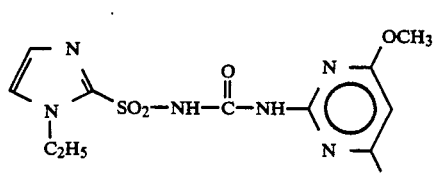
Compound 7
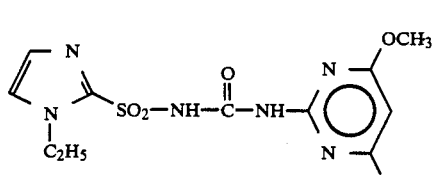
-continued
Compounds
Compound 8
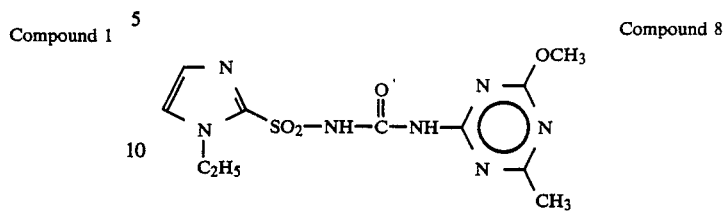
Compound 9
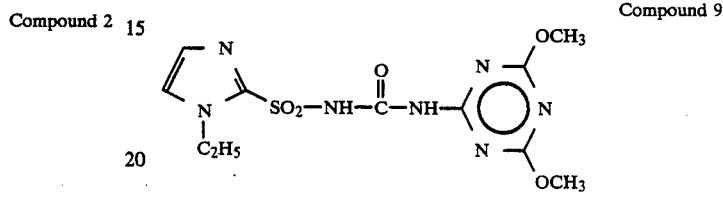
Compound 10
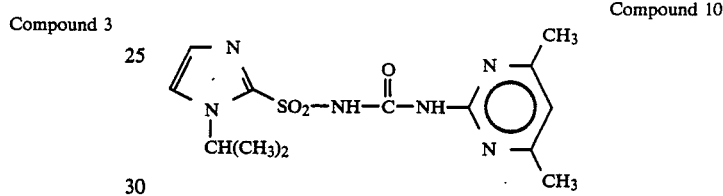
Compound 11
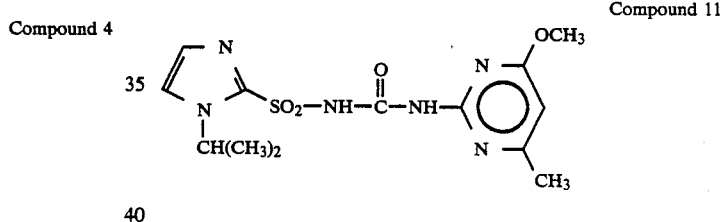
Compound 12
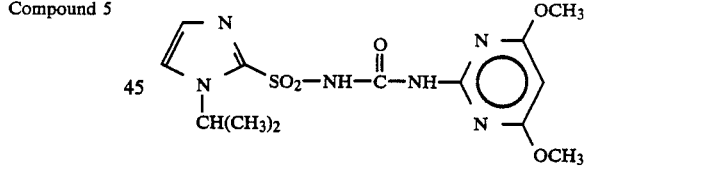
Compound 13
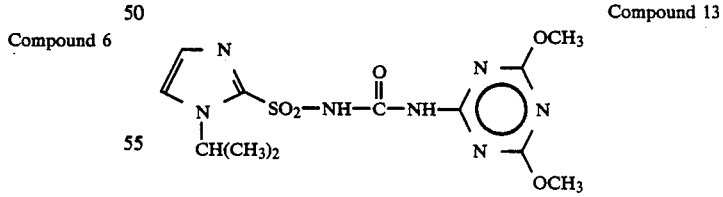
Compound 14
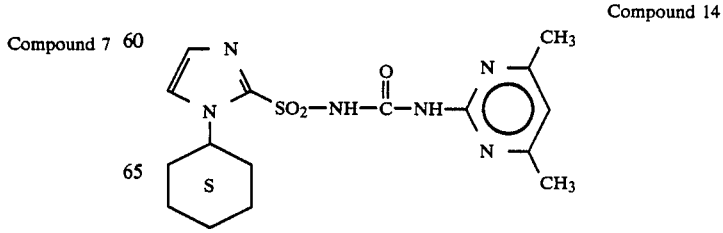

-continued
Compounds
Compound 15
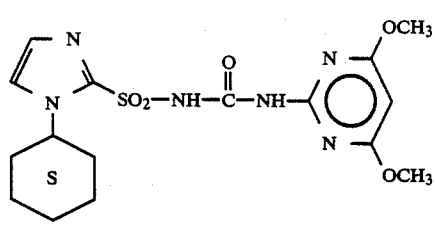
Compound 16
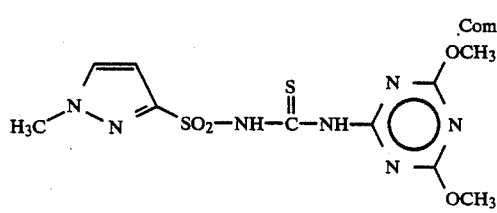
Compound 17
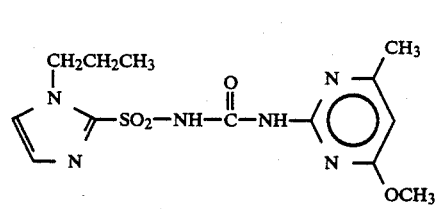
Compound 18
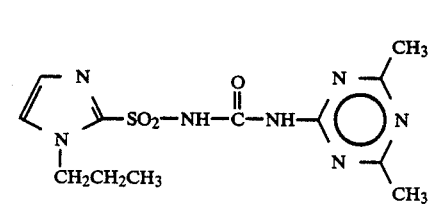
Compound 19
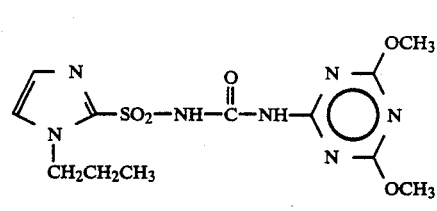
Compound 20
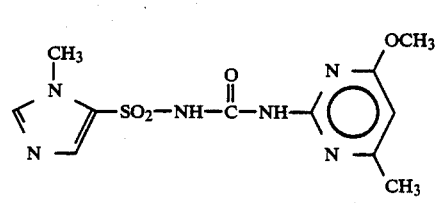
Compound 21
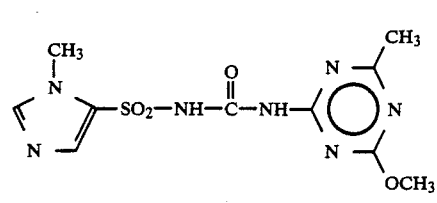
-continued
Compounds
Compound 22
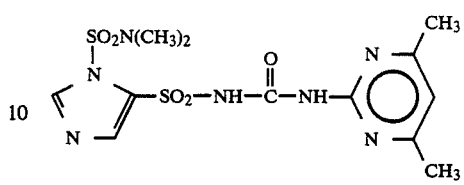
Compound 23
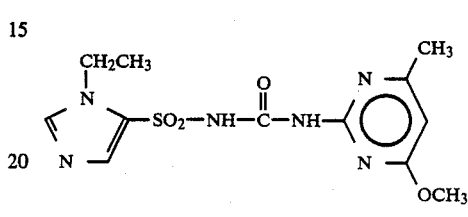
Compound 24
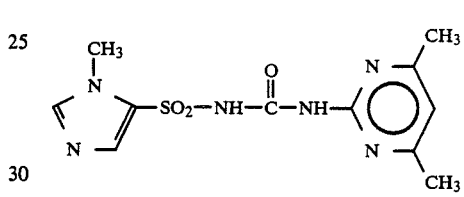
Compound 25
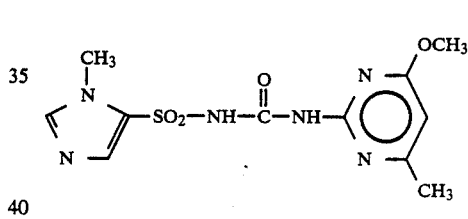
Compound 26
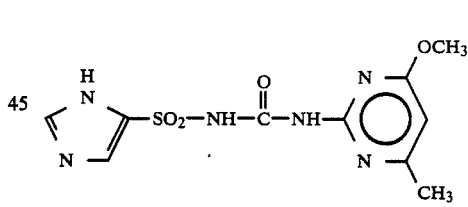
Compound 27
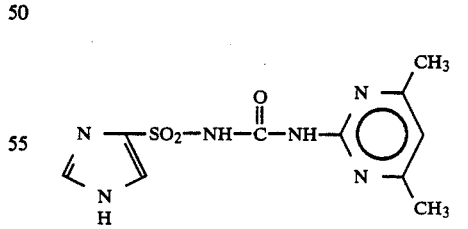
Compound 28
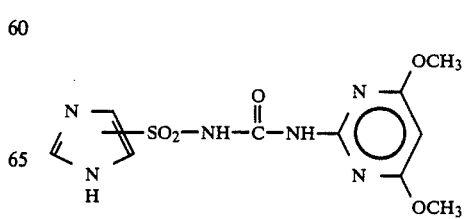

-continued
Compounds

Compound 29
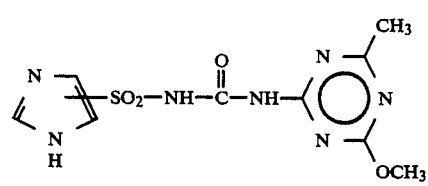

Compound 30
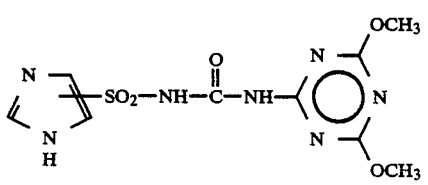
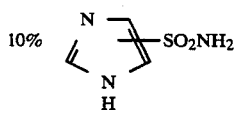
10%

Compound 31
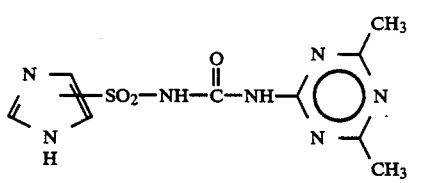
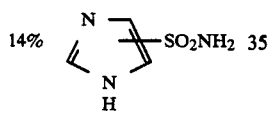
14%

Compound 32
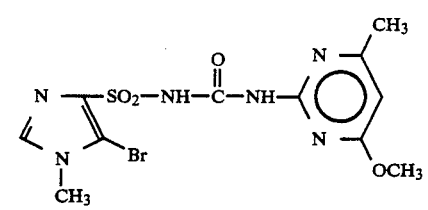

Compound 33
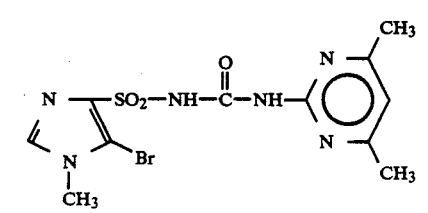

-continued
Compounds

Compound 34
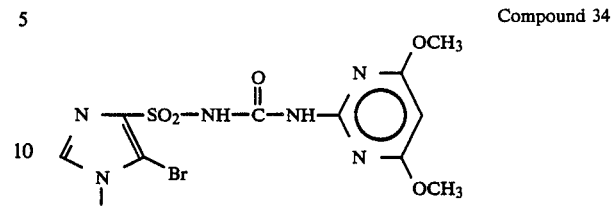

Compound 35
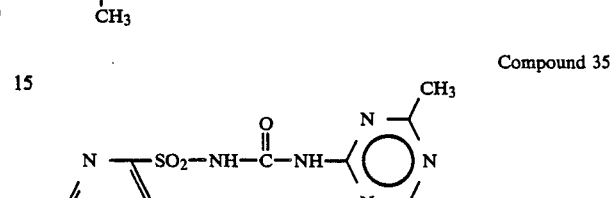

Compound 36
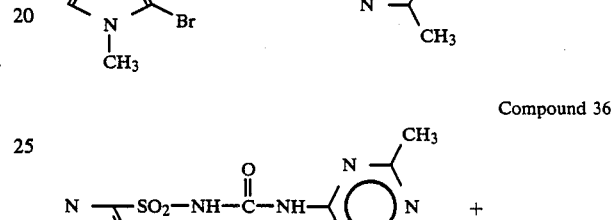
25%

Compound 37
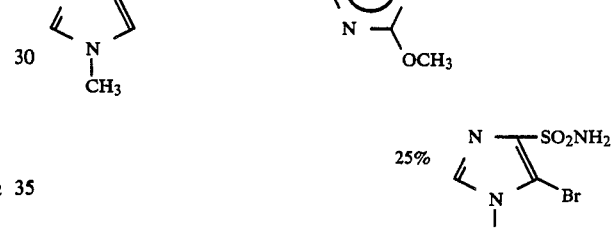

Compound 38
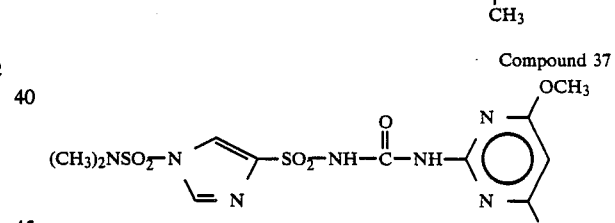

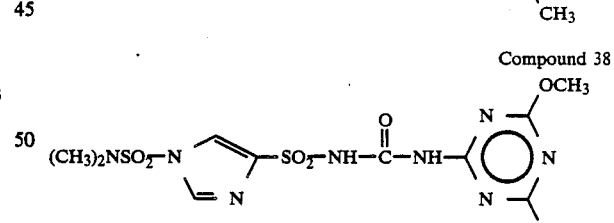

TABLE A

| Rate kg/ha | Cmpd. 1 0.4 | Cmpd. 2 0.4 | Cmpd. 3 0.4 | Cmpd. 4 0.4 | Cmpd. 5 0.05 | Cmpd. 6 0.05 | Cmpd. 7 0.05 | Cmpd. 8 0.05 |
|---|---|---|---|---|---|---|---|---|
| | | | POST-EMERGENCE | | | | | |
| Bush bean | 9C | 5C,6G,6Y | 9C | 0 | 9C | 9C | 9C | 1C |
| Cotton | 2U,4C,9G | 5C,8G | 5C,9G | 0 | 4C,9G | 5C,9G | 5C,9G | 0 |
| Morningglory | 6C,9G | 4C,9H | 9C | 0 | 5C,9G | 9C | 9C | 0 |
| Cocklebur | 9C | 2C,8G | 10C | 0 | 5C,9G | 9C | 9C | 0 |
| Sicklepod | 5C,9G | 2C | 5C,8G | 0 | 5C,9G | 9C | 9C | 0 |
| Nutsedge | 2C,9G | 2C,8G | 4C,9G | 0 | 4C,9G | 6C,9G | 9C | 0 |
| Crabgrass | 2C,8G | 2C,7G | 2C,8G | 0 | 2C,9G | 6C,9G | 9C | 0 |
| Barnyardgrass | 9C | 3C,9H | 9C | 2G | 10C | 9C | 9C | 0 |

TABLE A-continued

| | | | | | | | | |
|---|---|---|---|---|---|---|---|---|
| Wild Oats | 3C,9G | 2C,9H | 9G,5X | 3G | 5C,9G | 5C,9G | 2C,9G | 0 |
| Wheat | 2C,9G | 2C,9G | 6G | 2G | 3U,9G | 2U,9G | 3C,9G | 0 |
| Corn | 4U,9G | 1C,5G | 7U,9G | 0 | 3U,9G | 5U,9C | 4U,9G | 0 |
| Soybean | 6C,9G | 1C,4G | 6C,9G | 0 | 9C | 9C | 9C | 0 |
| Rice | 6C,9G | 5C,9G | 6C,9G | 2C,6G | 2U,9G | 4C,9G | 5C,9G | 0 |
| Sorghum | 4U,9G | 3U,9G | 2U,9G | 0 | 9C | 5U,9C | 3U,9C | 0 |

PRE-EMERGENCE

| | | | | | | | | |
|---|---|---|---|---|---|---|---|---|
| Morningglory | 9C | 9G | 10C | 0 | 9G | 9C | 9C | 5G |
| Cocklebur | 9H | 9H | 9H | 0 | 9H | 9H | 9H | 0 |
| Sicklepod | 2C,9G | 2C,4G | 9G | 0 | 2C,9G | 5C,9G | 5C,9G | 2G |
| Nutsedge | 10E | 2C,7G | 10E | 0 | 10E | 10E | 10E | 0 |
| Crabgrass | 9G,5C | 2C,7G | 2C,7G | 0 | 3C,8G | 3C,8G | 3C,8G | 0 |
| Barnyardgrass | 5C,9H | 5C,9H | 5C,9H | 0 | 4C,9H | 6C,9H | 5C,9H | 2C |
| Wild Oats | 5C,9H | 3C,8G | 5C,9H | 0 | 5C,9H | 6C,9H | 5C,9H | 0 |
| Wheat | 3C,9H | 2C,9H | 2C,9H | 2G | 9H | 10E | 9H | 0 |
| Corn | 5C,9G | 2C,8H | 9G | 3G | 9G | 10E | 10E | 2C |
| Soybean | 9H | 2C | 9H | 0 | 9H | 9H | 9H | 0 |
| Rice | 10E | 9H | 10E | 9H | 10E | 10E | 10E | 3C,4G |
| Sorghum | 5C,9H | 2C,9H | 10H | 0 | 5C,9H | 7C,9H | 5C,9H | 3G |

| | Cmpd. 9 | Cmpd. 10 | Cmpd. 11 | Cmpd. 12 | Cmpd. 13 | Cmpd. 14 | Cmpd. 15 | Cmpd. 16 |
|---|---|---|---|---|---|---|---|---|
| Rate kg/ha | 0.05 | 0.05 | 0.05 | 0.05 | 0.05 | 0.05 | 0.05 | 0.4 |

POST-EMERGENCE

| | | | | | | | | |
|---|---|---|---|---|---|---|---|---|
| Bush bean | 3C,9G,6Y | 9C | 9C | 9C | 5C,9G,6Y | 2C,2H | 9C | 0 |
| Cotton | 1C | 6C,9G | 5C,9G | 5C,9G | 2C,8G | 2C,5G | 2C,5G | 0 |
| Morningglory | 1C,3G | 4C,9G | 9C | 5C,9G | 2C | 2C | 2C,8G | 0 |
| Cocklebur | 1C,5H | 5C,9G | 10C | 10C | 1H | 1C | 3C,9H | 0 |
| Sicklepod | 1C | 2C,6G | 7G | 2C,8G | 1C | 0 | 2C,5G | 0 |
| Nutsedge | 0 | 2C,7G | 2C,7G | 2C,8G | 0 | 0 | 2G | 0 |
| Crabgrass | 0 | 1C,5G | 2C,4H | 2C,5G | 0 | 0 | 0 | 0 |
| Barnyardgrass | 2C,3H | 6C,9G | 5C,9H | 5C,9H | 1H | 0 | 2C,7H | 0 |
| Wild Oats | 2C,5G | 5C,9G | 5C,9H | 2C,9G | 0 | 0 | 2G | 0 |
| Wheat | 0 | 8G | 7G | 9G | 0 | 0 | 0 | 0 |
| Corn | 2C,8H | 2U,9G | 2U,9H | 5U,9C | 0 | 0 | 2C,5G | 0 |
| Soybean | 0 | 5C,9G | 4C,9H | 9C | 1C,5H | 0 | 3C,9H | 0 |
| Rice | 4C,9G | 6C,9G | 5C,9G | 6C,9G | 4C,9G | 3G | 7G | 5G |
| Sorghum | 4C,9H | 6C,9G | 4U,9G | 10C | 3C,9H | 2G | 3C,9H | 1C,3H |

PRE-EMERGENCE

| | | | | | | | | |
|---|---|---|---|---|---|---|---|---|
| Morningglory | 2C | 9G | 9C | 9G | 0 | 0 | 1C,9G | 0 |
| Cocklebur | — | 10E | 9H | 9H | 0 | 0 | — | 0 |
| Sicklepod | 5G | 4C,9G | 4C,9G | 3C,9G | 0 | 0 | 2C,7G | 0 |
| Nutsedge | 0 | 10E | 9G | 10E | 0 | 0 | 2C,7G | 0 |
| Crabgrass | 0 | 4G,2C | 2C,5G | 3C,9G | 1C | 0 | 1C | 0 |
| Barnyardgrass | 2C,5H | 5C,9H | 5C,9H | 9H | 0 | 0 | 3C,8G | 0 |
| Wild Oats | 2C,8G | 4C,8H | 5C,9H | 5C,9H | 0 | 0 | 1C,7G | 0 |
| Wheat | 2C,8G | 8H | 3C,9H | 3C,9H | 2G | 0 | 1C,7G | 0 |
| Corn | 2C,9H | 4C,7G | 9H | 9H | 2C | 0 | 3C,9H | 0 |
| Soybean | 2G | 4C,7H | 8H | 9H | 2C | 0 | 7H | 0 |
| Rice | 10E | 10E | 10E | 10E | 3C | 3G | 3C,7H | 0 |
| Sorghum | 2C,9H | 4C,9G | 5C,9H | 2C,9H | 3C | 0 | 3C,8H | 0 |

| | Compound 17 | Cmpd. 18 | Cmpd. 19 | Cmpd. 20 | Cmpd. 21 | Cmpd. 22 | Cmpd. 23 |
|---|---|---|---|---|---|---|---|
| Rate g/ha | 50 | 50 | 50 | 50 | 50 | 50 | 400 | 50 |

POST-EMERGENCE

| | | | | | | | | |
|---|---|---|---|---|---|---|---|---|
| Bush bean | 3C,9G,6Y | 9C | 3C,6H,6Y | 5C,9G,6Y | 4C,5G,6Y | 4C,7G,6Y | 4C,5H,6Y | 2C,4C,6Y |
| Cotton | 0 | 5C,9G | 0 | 1C | 1C | 2C,2H | 1C | 2C |
| Morningglory | 3C,8G | 9C | 0 | 2C,4G | 2C,4G | 2C,2H | 2C | 2C,4G |
| Cocklebur | 3C,8G | 9C | 2G | 2C | 2C,6G | 3C,8G | 1C | 2C,2H |
| Sicklepod | 1C | 9C | 0 | 2C | 2C | 2G | 0 | 0 |
| Nutsedge | 1C | 2C,8G | 0 | 0 | 2G | 0 | 0 | 0 |
| Crabgrass | 0 | 2C,8G | 0 | 0 | 2G | 2C,2G | 2G | 2C,9G |
| Barnyardgrass | 1C,2H | 9C | 1H | 0 | 2C,7H | 2C,4H | 1H | 5C,9H |
| Wild Oats | 0 | 2C,9G | 5G | 2C,8G | 5C,9G | 0 | 0 | 5C,7H |
| Wheat | 0 | 3C,9G | 2C,5G | 6G | 9C | 0 | 0 | 9C |
| Corn | 2C,7H | 2U,9G | 2C,9G | 0 | 4C,9H | 3C,9H | 2C,4G | 5G |
| Soybean | 5G | 5C,9G | 0 | 2C,9G | 3C,9G,5X | 4C,6G | 0 | 3C,8G,8X |
| Rice | 6G | 5C,9G | 5C,9G | 5C,9G | 5C,9G | 2C,7G | 2C,5G | 2C,9G |
| Sorghum | 4G | 4C,9G | 2C,8H | 2C,9G | 4C,9G | 4C,9H | 2C,5G | 2C,9G |
| Sugar beet | 2G | 5C,9G | 0 | 4C,9G | 3C,7G | 4C,6G | 2C | 0 |

PRE-EMERGENCE

| | | | | | | | | |
|---|---|---|---|---|---|---|---|---|
| Morningglory | 5G | 9C | 0 | 5G | 0 | | 2G | 2C | 0 |
| Cocklebur | 9H | 9H | 0 | 0 | 0 | | 0 | 5G | 0 |
| Sicklepod | 5G | 9G | 0 | 2C,9G | 0 | | 2G | 2G | 0 |
| Nutsedge | 0 | 10E | 0 | 0 | 0 | | 0 | 0 | 0 |
| Crabgrass | 0 | 2C,8G | 0 | 2C | 0 | | 2G | 2G | 2C,5G |
| Barnyardgrass | 2C,2H | 2C,9H | 0 | 2C,4G | 0 | | 1C | 1C | 2H |
| Wild Oats | 3G | 5C,9H | 0 | 2C,9G | 0 | | 2G | 2G | 2C,7G |
| Wheat | 0 | 5C,9H | 0 | 2C,9G | 0 | | 0 | 2G | 5C,9G |
| Corn | 2G | 10H | 0 | 2C,9G | 1C | | 2C,5G | 2C | 1C |
| Soybean | 2C | 9H | 0 | 3C,3H | 1C | | 0 | 0 | 0 |
| Rice | 3C,5G | 10E | 0 | 10E | 0 | | 1C | 2C,9G | 2G |

TABLE A-continued

| | | | | | | | | |
|---|---|---|---|---|---|---|---|---|
| Sorghum | 0 | 4C,9H | 0 | 3C,9H | 2G | 2C,7G | 3C,7G | 2C |
| Sugar beet | 9G | 5C,9G | 0 | 5C,9G | 3H | 6G | 3G | 3H |

| Rate g/ha | Cmpd. 24 50 | Cmpd. 25 50 | Cmpd. 26 50 | Cmpd. 27 50 | Cmpd. 28 50 | Cmpd. 29 50 | Cmpd. 30 50 | Cmpd. 31 50 |
|---|---|---|---|---|---|---|---|---|
| POST-EMERGENCE | | | | | | | | |
| Bush bean | 0 | 1C | 5C,8G,6Y | — | — | — | — | — |
| Cotton | 0 | 0 | 1C | 0 | 4C,6H | 0 | 0 | 0 |
| Morningglory | 0 | 1C,2H | 3C,8G | 0 | 3C,8G | 1C | 0 | 0 |
| Cocklebur | 0 | 2C,8G | 2C,9H | 0 | 4C,9H | 0 | 0 | 0 |
| Sicklepod | 0 | 1C | 3C | 0 | 4C,9G | 0 | 0 | 0 |
| Nutsedge | 0 | 0 | 8G | 0 | 2C,9G | 0 | 0 | 0 |
| Crabgrass | 0 | 0 | 2C,9G | 0 | 3C,9G | 0 | 0 | 0 |
| Barnyardgrass | 0 | 0 | 9C | 0 | 3C,9H | 0 | 0 | 0 |
| Wild Oats | 0 | 0 | 5C,9G | 0 | 4C,9G | 0 | 0 | 0 |
| Wheat | 0 | 0 | 6C,9G | 0 | 4C,9G | 0 | 0 | 0 |
| Corn | 0 | 0 | 2C,9G | 0 | 4U,9G | 0 | 0 | 0 |
| Soybean | 0 | 2H | 4C,8G | 0 | 2C,8G | 0 | 0 | 0 |
| Rice | 0 | 0 | 5C,9G | 0 | 5C,9G | 0 | 0 | 0 |
| Sorghum | 0 | 0 | 5C,9G | 0 | 4C,9G | 0 | 0 | 0 |
| Sugar beet | 0 | 2C,7G | 3C,6G | 0 | 5C,9H | 0 | 0 | 0 |
| PRE-EMERGENCE | | | | | | | | |
| Morningglory | 0 | 2C | 5G | 0 | 8G | 0 | 0 | 0 |
| Cocklebur | 0 | — | 5H | 0 | 2C,8H | 0 | 0 | 0 |
| Sicklepod | 0 | 2G | 2G | 0 | 5G | 0 | 0 | 0 |
| Nutsedge | 0 | 0 | 0 | 0 | 9G | 0 | 0 | 0 |
| Crabgrass | 0 | 2G | 2C,4G | 0 | 2C,6G | 0 | 0 | 0 |
| Barnyardgrass | 0 | 2C | 4C,9H | 0 | 5C,9H | 0 | 0 | 0 |
| Wild Oats | 0 | 0 | 2C,9G | 0 | 3C,8H | 0 | 0 | 0 |
| Wheat | 0 | 0 | 6C,9H | 0 | 4C,9H | 0 | 0 | 0 |
| Corn | 0 | 0 | 2C,9G | 0 | 9G | 0 | 0 | 0 |
| Soybean | 0 | 0 | 1C,1H | 0 | 1C | 0 | 0 | 0 |
| Rice | 0 | 2C | 9H | 0 | 10E | 0 | 0 | 0 |
| Sorghum | 0 | 2G | 5C,9H | 0 | 4C,9H | 0 | 0 | 0 |
| Sugar beet | 0 | 6G | 8G | 0 | 2C,8G | 0 | 0 | 0 |
| Cotton | — | — | — | 0 | 6G | 0 | 0 | 0 |

| Rate g/ha | Cmpd. 32 50 | Cmpd. 33 50 | Cmpd. 34 50 | Cmpd. 35 50 | Cmpd. 36 50 | Cmpd. 37 50 | Cmpd. 38 50 |
|---|---|---|---|---|---|---|---|
| POST-EMERGENCE | | | | | | | |
| Bush bean | — | — | — | — | — | 0 | 0 |
| Cotton | 5C,9G | 3C,4H | 4C,9G | 0 | 0 | 0 | 0 |
| Morningglory | 9C | 1C,3G | 9C | 0 | 0 | 0 | 0 |
| Cocklebur | 2C,9G | 0 | 5C,9G | 0 | 0 | 0 | 0 |
| Sicklepod | 5C,9G | 0 | 5C,9G | 0 | 0 | 0 | 0 |
| Nutsedge | 4C,9G | 6G | 9G | 0 | 0 | 0 | 5G |
| Crabgrass | 3C,8G | 2C,5H | 2C,9G | 0 | 0 | 0 | 0 |
| Barnyardgrass | 3C,8G | 2C,8G | 3C,9H | 0 | 0 | 0 | 0 |
| Wild Oats | 4C,9G | 10C | 3C,9G | 0 | 0 | 0 | 0 |
| Wheat | 5C,9G | 2U,9G | 9C | 0 | 0 | 0 | 0 |
| Corn | 4C,9G | 3C,8G | 4U,9G | 0 | 0 | 0 | 0 |
| Soybean | 3C,9G | 5C,9G | 9C | 0 | 0 | 0 | 0 |
| Rice | 5C,9G | 3C,9G | 5C,9G | 0 | 0 | 0 | 0 |
| Sorghum | 5C,9G | 2C,8G | 4C,9G | 0 | 0 | 0 | 0 |
| Sugar beet | 9C | 2C,6H | 5C,9G | 0 | 0 | 0 | 0 |
| PRE-EMERGENCE | | | | | | | |
| Morningglory | 9G | 0 | 9G | 0 | 0 | 0 | 0 |
| Cocklebur | 8G | 0 | 9H | 0 | 0 | 0 | 0 |
| Sicklepod | 4C,9G | 0 | 9G | 0 | 0 | 0 | 0 |
| Nutsedge | 2C | 0 | 9G | 0 | 0 | 0 | 5G |
| Crabgrass | 1C | 0 | 7G | 0 | 0 | 0 | 0 |
| Barnyardgrass | 2C,3G | 0 | 2C,7H | 0 | 0 | 0 | 0 |
| Wild Oats | 5C,8H | 1C,3G | 3C,8G | 0 | 0 | 0 | 0 |
| Wheat | 6C,9H | 5C,9H | 2C,8H | 0 | 0 | 0 | 0 |
| Corn | 5C,9H | 8G | 2C,9G | 0 | 0 | 0 | 0 |
| Soybean | 4C,9H | 0 | 8H | 0 | 0 | 0 | 0 |
| Rice | 10E | 9H | 10E | 0 | 0 | 0 | 0 |
| Sorghum | 5C,9G | 2C,5G | 5C,9H | 0 | 0 | 0 | 0 |
| Sugar beet | 5C,9G | 3H | 4C,9G | 0 | 0 | 0 | 0 |
| Cotton | 7G | 0 | 9G | 0 | 0 | 0 | 0 |

TEST B

Two plastic bulb pans were filled with fertilized and limed Fallsington silt loam soil. One pan was planted with corn, sorghum, Kentucky bluegrass and several grass weeds. The other pan was planted with cotton, soybeans, purple nutsedge (*Cyperus rotundus*), and several broadleaf weeds. The following grass and broadleaf weeds were planted: crabgrass (*Digitaria sanguinalis*), barnyardgrass (*Echinochloa crusgalli*), wild oats (*Avena fatua*), johnsongrass (*Sorghum halepense*), dallisgrass (*Paspalum dilatatum*), giant foxtail (*Setaria faberii*), cheatgrass (*Bromus secalinus*), mustard (*Brassica arvensis*), cocklebur (*Xanthium pensylvanicum*), pigweed (Amaranthus retroflexus), morningglory (Ipomoea hederacea), sicklepod (Cassia obtusifolia), teaweed (Sida spinosa), velvetleaf (Abutilon theophrasti), and jimsonweed (Datura stramonium). A 12.5 cm diameter plastic pot was also filled with prepared soil and planted with rice and wheat. Another 12.5 cm pot was planted with sugar beets. The above four containers were treated pre-emergence with several test compounds within the scope of the invention.

Twenty-eight days after treatment, the plants were evaluated and visually rated for response to the chemical treatments utilizing the rating system described previously for Test A. The data are summarized in Table B. Note that the compounds tested are highly active herbicides and retard the growth of several plant species.

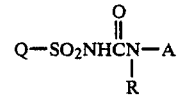

where
R is H or CH$_3$;
Q is

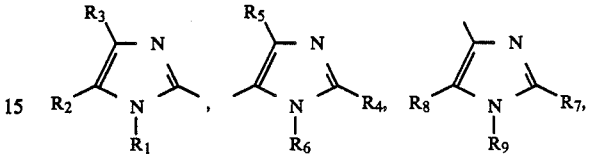

TABLE B

PRE-EMERGENCE ON FALLSINGTON SILT LOAM

|  | Compound 1 | | Compound 2 | | Compound 3 | | Compound 5 | | Compound 6 | |
|---|---|---|---|---|---|---|---|---|---|---|
| Rate kg/ha | .03 | .120 | .03 | .120 | .03 | .120 | .03 | .120 | .03 | .120 |
| Crabgrass | 5G | 7G,3H | 0 | 0 | 4G | 6G | 5G | 8G,3H | 7G | 8G,3H |
| Barnyardgrass | 6G | 9G,5C | 0 | 3G | 7G | 8G,3C | 7G,5H | 10C | 9G,8C | 10C |
| Sorghum | 8G,5H | 10C | 5G,3H | 6G,5H | 6G,5H | 7G,5H | — | — | — | — |
| Wild Oats | 6G,3H | 7G,5H | 0 | 4G | 4G | 6G | 7G,3H | 8G,6C | 8G,5H | 8G,3H |
| Johnsongrass | 8G,5H | 9G,5H | 0 | 4G | 6G,3H | 8G,5H | 9G,8C | 9G,8C | 8G,3H | 7G,3C |
| Dallisgrass | 3G | 8G,3H | 0 | 2G | 2G | 5G | 8G | 9G,8C | 9G,8C | 9G,8C |
| Giant foxtail | 4G,3H | 9G,5H | 0 | 2G | 4G,3H | 6G,5H | 9G,8C | 9G,9C | 9G,9C | 9G,9C |
| Ky. bluegrass | 5G | 7G,7C | 0 | 0 | 5G | 7G,5C | 8G,8C | 10C | 10C | 10C |
| Cheatgrass | 5G | 10C | 0 | 3G | 0 | 3G | 7G,8C | 9G,9C | 10C | 8G,7C |
| Sugar beets | 7G,5C | 9G,8C | 0 | 0 | 6G,4C | 9G,9C | 7G,5H | 10C | 9G,9C | 10C |
| Corn | 3G | 5G | 0 | 0 | 3G | 6G,3H | 6G,3H | 10C | 10C | 10C |
| Mustard | 9G,9C | 10C | 0 | 7G,3H | 7G,5C | 9G,9C | 8G,8C | 10C | 10C | 10C |
| Cocklebur | 5G | 6G,3H | 0 | 0 | 3G | 5G | 7G,3C | 7G,5H | 7G | 7G,5H |
| Pigweed | 9G,9C | 9G,9C | 0 | 0 | 5G | 8G,8C | 8G,5C | 10C | 8G,8C | 10E |
| Nutsedge | 0 | 8G | 0 | 0 | 0 | 8G | 8G | 10E | 8G | 9G |
| Cotton | 4G | 8G,5H | 0 | 0 | 0 | 7G,5H | 4G,5H | 8G,5H | 8G,5H | 9G,5H |
| Morningglory | 8G,3C | 8G,6C | 0 | 3G | 3G | 9G,6C | 7G,5H | 9G,5C | 9G,7C | 8G,7C |
| Sicklepod | 8G | 8G,6C | 0 | 0 | 8G,3H | 9G,5C | 6G | 9G,7C | 9G,7C | 9G,9C |
| Teaweed | 3G | 7G,3C | 0 | 0 | 0 | 5G,5H | 6G | 6G | 6G,3H | 8G,5H |
| Velvetleaf | 5G,5H | 9G,9C | 0 | 0 | 7G,5H | 9G,9C | 7G,5H | 8G,8C | 6G,5H | 9G,7C |
| Jimsonweed | 3G | 9G,9C | 0 | 0 | 4G | 8G,5C | 5G | 8G,8C | 8G,8C | 9G,9C |
| Soybean | 0 | 8G,5H | 0 | 0 | 0 | 3G,2H | 6G,5H | 9G,5H | 9G,5H | 9G,5H |
| Rice | 10C | 10E | 4G | 3G,2H | 6G,3H | 10E | 10E | 10E | 10E | 10E |
| Wheat | 3G | 6G | 0 | 0 | 0 | 3G | 5G | 9G,9C | 8G,7C | 10C |

|  | Compound 7 | | Compound 9 | | Compound 10 | | Compound 11 | | Compound 12 | |
|---|---|---|---|---|---|---|---|---|---|---|
| Rate kg/ha | .03 | .120 | .03 | .120 | .03 | .120 | .03 | .120 | .03 | .120 |
| Crabgrass | 7G | 8G,3H | 0 | 0 | 0 | 2G | 0 | 6G | 3G | 4G |
| Barnyardgrass | 9G,8C | 9G,9C | 0 | 0 | 4G | 9G,3H | 9G,3H | 9G,9C | 9G,5H | 9G,9C |
| Sorghum | — | — | 0 | 5G,3H | 8G,3H | 9G,9C | 10E | 10C | 10E | 10E |
| Wild Oats | 7G,3H | 7G,3H | 2G | 3G | 7G | 8G | 8G | 8G,3C | 7G | 7G,3C |
| Johnsongrass | 8G,5H | 8G,8C | 0 | 0 | 8G,3H | 10C | 8G,3H | 8G,3H | 8G,4C | 8G,8C |
| Dallisgrass | 9G,8C | 9G,7C | 0 | 2G | 0 | 8G,3H | 6G | 8G,3H | 6G | 8G |
| Giant foxtail | 9G,7C | 9G,9C | 0 | 2G | 0 | 5G | 6G,3H | 9G,5H | 8G,5H | 9G,8C |
| Ky. bluegrass | 10C | 10C | 2G | 5G | 0 | 7G,5H | 8G,8C | 10C | 8G,8C | 10C |
| Cheatgrass | 10C | 10C | 4G | 2G | 6G | 8G,8C | 8G,8C | 9G,9C | 10E | 10E |
| Sugar beets | 10C | 10C | 2G | 4G | 5G,3H | 10C | 9G,8C | 10C | 10C | 10C |
| Corn | 9G,9C | 10C | 5G | 5G | 2G | 5G,2H | 5G,2C | 10C | 7G,5H | 9G,9C |
| Mustard | 10C | 10C | 3G | 4G | 7G,3H | 9G,9C | 10C | 10C | 9G,9C | 10C |
| Cocklebur | 7G,5H | 8G,5H | 0 | 0 | 0 | 9G,9C | 8G,3H | 8G,8C | 8G,8C | 9G,9C |
| Pigweed | 10C | 10E | — | — | 8G,8C | 10C | 10E | 10E | 9G,9C | 10C |
| Nutsedge | 10E | 10E | 0 | 4G | 6G | 10E | 9G | 9G | 10E | 10E |
| Cotton | 8G,5H | 9G,5H | 0 | 2G | 0 | 6G,5H | 6G,3H | 7G,5H | 7G,5H | 8G,3H |
| Morningglory | 9G,7C | 9G,9C | 0 | 0 | 3G,3H | 6G,5H | 9G,7C | 9G,8C | 9G,8C | 9G,9C |
| Sicklepod | 9G,9C | 9G,9C | 0 | 4G | 3G | 6G | 7G | 9G,9C | 8G,4C | 9G,7C |
| Teaweed | 7G | 8G,5C | 2G | 2G | 3G | 6G,3H | 5G | 8G,3H | 7G | 8G,3H |
| Velvetleaf | 9G,7C | 9G,9C | 0 | 2G | — | 8G,7C | 7G,5H | 9G,9C | 9G,9C | 10C |
| Jimsonweed | 10C | 9G,8C | 0 | 0 | 0 | 8G,7C | 8G,5C | 9G,7C | 8G,5C | 9G,7C |
| Soybean | 9G,5H | 9G,9C | 0 | 0 | 0 | 4G,2H | 4G,3H | 7G,5H | 8G,5H | 9G,5H |
| Rice | 10E | 10E | 5G | 10C | 8G,5H | 10E | 10E | 10E | 10E | 10E |
| Wheat | 5G | 9G,9C | 0 | 0 | 0 | 4G | 3G | 7G | 5G | 7G |

What is claimed is:

1. A compound of the formula:

-continued

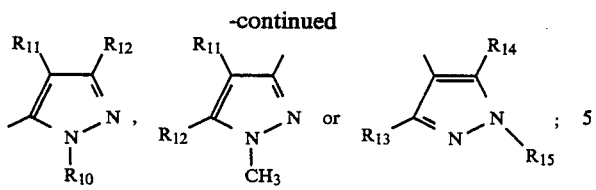

$R_1$ is H, $C_1$–$C_8$ alkyl, $C_3$–$C_6$ alkenyl, $C_5$–$C_6$ cycloalkyl, $C_5$–$C_6$ cycloalkenyl, $C_3$–$C_6$ alkynyl, $C_4$–$C_7$ cycloalkylalkyl, $(R_{17}CH)_nC(O)R_{16}$, $(R_{17}CH)_nCO_2R_{18}$, $(R_{17}CH)_nCOSR_{19}$, $(R_{17}CH)_nCONR_{20}R_{21}$, $(R_{17}CH)_nSO_2NR_{20}R_{21}$, $(R_{17}CH)_nSO_2R_{22}$,

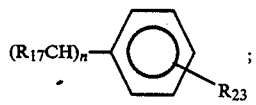

or $C_1$–$C_6$ alkyl substituted either with
(a) 1–3 atoms of F, Br or Cl; or
(b) $OR_{16}$;
provided that,
(1) the total number of carbon atoms in $R_1$ is less than or equal to 8; and
(2) if $R_1$ is other than $C_1$–$C_3$ alkyl, then $R_3$ must be H;
$R_2$, $R_3$ and $R_4$ are independently H or $CH_3$;
$R_5$ is H, $C_1$–$C_4$ alkyl, $-OR_6$, $NO_2$, F, Cl, Br, $CO_2R_{24}$, $S(O)_mR_{25}$ or $SO_2NR_{20}R_{21}$;
$R_6$ is H, $C_1$–$C_4$ alkyl, $C_3$–$C_4$ alkenyl, $C_3$–$C_4$ alkynyl, $CO_2R_{18}$, $SO_2NR_{20}R_{21}$, $SO_2R_{22}$ or $C_1$–$C_4$ alkyl substituted with (a) 1–3 atoms of F, Cl or Br; or (b) $OCH_3$;
provided that,
(1) when $R_5$ is other than H, $CH_3$, $OCH_3$ or $NO_2$, then $R_6$ is H or $CH_3$; and
(2) when $R_6$ is $CO_2R_{18}$, $SO_2NR_{20}R_{21}$ or $SO_2R_{22}$, then $R_5$ is H, $CH_3$, $OCH_3$ or $NO_2$;
$R_7$ is H or $CH_3$;
$R_8$ is H, $C_1$–$C_4$ alkyl, $-OR_{16}$, $NO_2$, F, Cl, Br, $CO_2R_{24}$, $S(O)_mR_{25}$ or $SO_2NR_{20}R_{21}$;
$R_9$ is $CH_3$ or $C_2H_5$;
$R_{10}$ is H, $C_1$–$C_4$ alkyl, $C_3$–$C_4$ alkenyl, $C_3$–$C_4$ alkynyl, $CO_2R_{24}$, $SO_2NR_{20}R_{21}$ or $SO_2R_{22}$;
$R_{11}$ is H, $C_1$–$C_3$ alkyl, F, Cl, Br, $NO_2$, $-OR_{16}$, $CO_2R_{24}$, $S(O)_mR_{25}$ or $SO_2NR_{20}R_{21}$; provided that, when $R_{10}$ is other than $C_1$–$C_3$ alkyl, then $R_{11}$ is H, Cl, $OCH_3$, $NO_2$ or $CH_3$;
$R_{12}$ is H or $CH_3$;
$R_{13}$ and $R_{14}$ are independently H, $C_1$–$C_3$ alkyl $-OR_{16}$, F, Cl, Br, $NO_2$, $CO_2R_{24}$, $S(O)_mR_{25}$ or $SO_2NR_{20}R_{21}$; provided that, when either of $R_{13}$ or $R_{14}$ is $CO_2R_{24}$, $S(O)_mR_{25}$ or $SO_2NR_{20}R_{21}$, then the other is H, Cl, $CH_3$, $OCH_3$ or $NO_2$;
$R_{15}$ is H or $CH_3$;
$R_{16}$ is $C_1$–$C_3$ alkyl;
$R_{17}$ is H or $CH_3$;
$R_{18}$ is $C_1$–$C_4$ alkyl, $C_3$–$C_4$ alkenyl, $C_3$–$C_4$ alkynyl, $CH_2CH_2Cl$ or $CH_2CH_2OCH_3$;
$R_{19}$ is $C_1$–$C_4$ alkyl, $C_3$–$C_4$ alkenyl, $C_3$–$C_4$ alkynyl or $CH_2CH_2OCH_3$;
$R_{20}$ and $R_{21}$ are independently $CH_3$ or $C_2H_5$;
$R_{22}$ is $C_1$–$C_3$ alkyl or $CF_3$;
$R_{23}$ is H, Cl, Br, $CH_3$, F, $CF_3$, $OCH_3$ or $NO_2$;
$R_{24}$ is $C_1$–$C_3$ alkyl or allyl;

$R_{25}$ is $C_1$–$C_3$ alkyl;
m is 0, 1 or 2;
n is 0 or 1;
A is

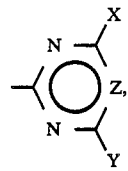

X is $CH_3$, $OCH_3$, Cl, F, $OCF_2H$ or $SCF_2H$;
Y is $CH_3$, $C_2H_5$, $OCH_3$, $OC_2H_5$, $CH_2OCH_3$, $CH(OCH_3)_2$, $OCH_2CF_3$, $OCF_3$, $NH_2$, $NHCH_3$, $N(CH_3)_2$ or $GCF_2T$ where G is O or S and T is H, CHClF, CHBrF, $CF_2H$ or $CHFCF_3$;
Z is CH;
$Y_1$ is H, Cl, $CH_3$, $OCH_3$ or $OCF_2H$;
$X_2$ is $OCH_3$, $CH_3$, $CH_2CH_3$, $OCH_2CH_3$, $SCH_3$ or $SCH_2CH_3$;
$Y_2$ is $CH_3$, $CH_2CH_3$ or $CH_2CF_3$;
$X_3$ is $OCH_3$ or $CH_3$;
provided that,
when X is Cl or F, then Z is CH and Y is $OCH_3$, $NH_2$, $NHCH_3$ or $N(CH_3)_2$;
and agriculturally suitable salts thereof.

2. A compound of claim 1 where
A is

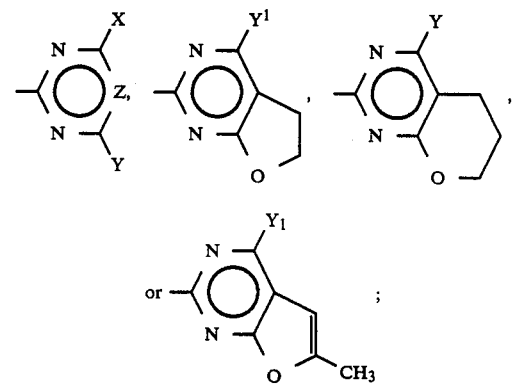

X is $CH_3$, $OCH_3$ or Cl;
Y is $CH_3$, $C_2H_5$, $OCH_3$, $OC_2H_5$, $CH_2OCH_3$, $CH(OCH_3)_2$, $NH_2$, $NHCH_3$ or $N(CH_3)_2$;
Z is CH or N;
$Y_1$ is H, Cl, $CH_3$ or $OCH_3$;
$X_2$ is $OCH_3$ or $CH_3$; and
$Y_2$ is $CH_3$.

3. Compounds of claim 1 where Q is

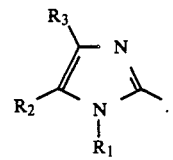

4. Compounds of claim 3 where R is H.
5. Compounds of claim 4 where X is $CH_3$, $OCH_3$, $OCF_2H$ or Cl and Y is $CH_3$, $OCH_3$ or $OCF_2H$.

6. Compounds of claim 5 where $R_1$ is H or $C_1$–$C_4$ alkyl, and $R_3$ is H.

7. Compounds of claim 1 where Q is

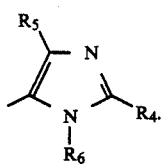

8. Compounds of claim 7 where R is H.

9. Compounds of claim 8 where $R_4$ is H.

10. Compounds of claim 9 where X is $CH_3$, $OCH_3$, $OCF_2H$ or Cl and Y is $CH_3$, $OCH_3$ or $OCF_2H$.

11. Compounds of claim 10 where $R_5$ is H, $CH_3$, $OCH_3$, Cl, $NO_2$, $CO_2R_{24}$ or $SO_2NR_{20}R_{21}$ and $R_6$ is H or $C_1$–$C_4$ alkyl.

12. Compounds of claim 1 where Q is

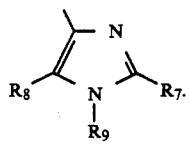

13. Compounds of claim 12 where R is H.

14. Compounds of claim 13 where $R_7$ is H.

15. Compounds of claim 14 where X is $CH_3$, $OCH_3$, $OCF_2H$ or Cl and Y is $CH_3$, $OCH_3$ or $OCF_2H$.

16. Compounds of claim 15 where $R_8$ is Br, $C_1$–$C_4$ alkyl, $OCH_3$, Cl, $NO_2$, $CO_2R_{24}$, $S(O)_mR_{25}$ or $SO_2NR_{20}R_{21}$.

17. Compounds of claim 1 where Q is

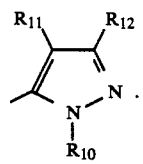

18. Compounds of claim 17 where R is H.

19. Compounds of claim 18 where X is $CH_3$, $OCH_3$, $OCF_2H$ or Cl and Y is $CH_3$, $OCH_3$ or $OCF_2H$.

20. Compounds of claim 1 where Q is

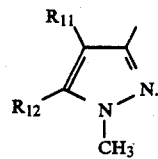

21. Compounds of claim 20 where R is H.

22. Compounds of claim 21 where X is $CH_3$, $OCH_3$, $OCF_2H$ or Cl and Y is $CH_3$, $OCH_3$ or $OCF_2H$.

23. Compounds of claim 22 where $R_1$ is H, $CH_3$, $OCH_3$, Cl, Br, $NO_2$, $CO_2CH_3$, $SO_2CH_3$ or $SO_2N(CH_3)_2$.

24. Compounds of claim 1 where Q is

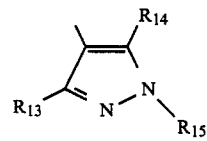

25. Compounds of claim 24 where R is H.

26. Compounds of claim 25 where X is $CH_3$, $OCH_3$, $OCF_2H$ or Cl and Y is $CH_3$, $OCH_3$ or $OCF_2H$.

27. The compound of claim 1 which is N-[(4,6-dimethylpyrimidin-2-yl)aminocarbonyl]-1-(1-methylethyl)-1H-imidazole-2-sulfonamide.

28. The compound of claim 1 which is N-[(4-methoxy-6-methylpyrimidin-2-yl)aminocarbonyl]-1-(1-methylethyl)-1H-imidazole-2-sulfonamide.

29. The compound of claim 1 which is N-[(4,6-dimethoxypyrimidin-2-yl)aminocarbonyl]-1-(1-methylethyl)-1H-imidazole-2-sulfonamide.

30. The compound of claim 1 which is N-[(4,6-dimethylpyrimidin-2-yl)aminocarbonyl]-1-ethyl-1H-imidazole-2-sulfonamide.

31. The compound of claim 1 which is N-[(4-methoxy-6-methylpyrimidin-2-yl)aminocarbonyl]-1-ethyl-1H-imidazole-2-sulfonamide.

32. The compound of claim 1 which is N-[(4,6-dimethoxypyrimidin-2-yl)aminocarbonyl]-1-ethyl-1H-imidazole-2-sulfonamide.

33. The compound of claim 1 which is N-[(4,6-dimethoxypyrimidin-2-yl)aminocarbonyl]-5-bromo-1-methyl-1H-imidazole-4-sulfonamide.

34. A composition suitable for controlling the growth of undesired vegetation comprising an effective amount of a compound of claim 1 and at least one of the following: surfactant, solid or liquid diluent.

35. A composition suitable for controlling the growth of undesired vegetation comprising an effective amount of a compound of claim 2 and at least one of the following: surfactant, solid or liquid diluent.

36. A composition suitable for controlling the growth of undesired vegetation comprising an effective amount of a compound of claim 3 and at least one of the following: surfactant, solid or liquid diluent.

37. A composition suitable for controlling the growth of undesired vegetation comprising an effective amount of a compound of claim 4 and at least one of the following: surfactant, solid or liquid diluent.

38. A composition suitable for controlling the growth of undesired vegetation comprising an effective amount of a compound of claim 5 and at least one of the following: surfactant, solid or liquid diluent.

39. A composition suitable for controlling the growth of undesired vegetation comprising an effective amount of a compound of claim 6 and at least one of the following: surfactant, solid or liquid diluent.

40. A composition suitable for controlling the growth of undesired vegetation comprising an effective amount of a compound of claim 7 and at least one of the following: surfactant, solid or liquid diluent.

41. A composition suitable for controlling the growth of undesired vegetation comprising an effective amount of a compound of claim 8 and at least one of the following: surfactant, solid or liquid diluent.

42. A composition suitable for controlling the growth of undesired vegetation comprising an effective amount of a compound of claim 9 and at least one of the following: surfactant, solid or liquid diluent.

43. A composition suitable for controlling the growth of undesired vegetation comprising an effective amount of a compound of claim 10 and at least one of the following: surfactant, solid or liquid diluent.

44. A composition suitable for controlling the growth of undesired vegetation comprising an effective amount of a compound of claim 11 and at least one of the following: surfactant, solid or liquid diluent.

45. A method for controlling the growth of undesired vegetation which comprises applying to the locus to be protected an effective amount of a compound of claim 1.

46. A method for controlling the growth of undesired vegetation which comprises applying to the locus to be protected an effective amount of a compound of claim 2.

47. A method for controlling the growth of undesired vegetation which comprises applying to the locus to be protected an effective amount of a compound of claim 3.

48. A method for controlling the growth of undesired vegetation which comprises applying to the locus to be protected an effective amount of a compound of claim 4.

49. A method for controlling the growth of undesired vegetation which comprises applying to the locus to be protected an effective amount of a compound of claim 5.

50. A method for controlling the growth of undesired vegetation which comprises applying to the locus to be protected an effective amount of a compound of claim 6.

51. A method for controlling the growth of undesired vegetation which comprises applying to the locus to be protected an effective amount of a compound of claim 7.

52. A method for controlling the growth of undesired vegetation which comprises applying to the locus to be protected an effective amount of a compound of claim 8.

53. A method for controlling the growth of undesired vegetation which comprises applying to the locus to be protected an effective amount of a compound of claim 9.

54. A method for controlling the growth of undesired vegetation which comprises applying to the locus to be protected an effective amount of a compound of claim 10.

55. A method for controlling the growth of undesired vegetation which comprises applying to the locus to be protected an effective amount of a compound of claim 11.

56. The compound of claim 18 where $R_{10}$ is $CH_3$, $R_{12}$ is H, $R_{11}$ is $COOR_{24}$, $R_{24}$ is $CH_3$, X is $OCH_3$ and Y is $OCH_3$.

57. A composition suitable for controlling the growth of undesired vegetation comprising an effective amount of the compound of claim 56 and at least one of the following: surfactant and solid or liquid diluent.

58. A method for controlling the growth of undesired vegetation which comprises applying to the locus to be protected an effective amount of a compound of claim 56.

59. A compound represented by the formula

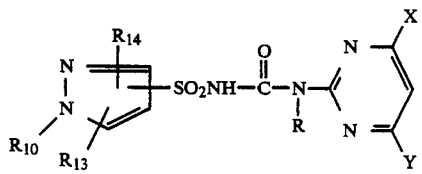

wherein $R_{10}$ is hydrogen, $C_1$-$C_4$ alkyl, $C_3$-$C_4$ alkenyl, $C_3$-$C_4$ alkynyl, $CO_2$-lower alkyl, $CO_2$ allyl, $SO_2N$ (lower alkyl)$_2$, $SO_2NH$ lower alkyl, $SO_2CF_3$; $R_{13}$ is hydrogen, $C_1$-$C_3$ alkyl, halo, $NO_2$, lower alkoxy, $CO_2$-lower alkyl, $CO_2$-lower alkenyl, S-lower alkyl, SO-lower alkyl, $SO_2N$ (lower alkyl)$_2$; $R_{14}$ is hydrogen, $C_1$-$C_3$ alkyl; R is hydrogen, methyl; X is methyl, methoxy, Cl, $OCF_2H$, $SCF_2H$; Y is methyl, ethyl, methoxy, ethoxy, $NHCH_3$, $N(CH_3)_2$, $NH_2$, $CH_2OCH_3$, $CH(OCH_3)_2$, $OCH_2CF_3$, $OCF_3$, $OCF_2CHClF$, $OCF_2$, $CF_2H$, $OCF_2CHFCF_3$, $OCF_2H$, $OCF_2CHBrF$; and agriculturally suitable salts thereof.

60. A herbicidal composition which comprises a pyrazole sulfonamide defined in claim 59 as an active ingredient.

61. A method for controlling the growth of undesired vegetation which comprises applying to the locus to be protected an effective amount of a compound of claim 59/are suggested for the purpose of interference.

62. A compound represented by the formula

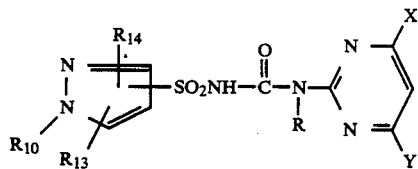

wherein R is H or $CH_3$; X is $CH_3$, $OCH_3$, Cl, F, $OCF_2H$ or $SCF_2H$; Y is $CH_3$, $C_2H_5$, $OCH_3$, $OC_2H_5$, $CH_2OCH_3$, $CH(OCH_3)_2$, $OCH_2F_3$, $OCF_3$, $NH_2$, $NHCH_3$, $N(CH_3)_2$ or $GCF_2T$ where G is O or S and T is H, CHClF, CHBrF, $CF_2H$ or $CHFCF_3$; $R_{10}$ is hydrogen, $C_1$-$C_4$ alkyl, $C_3$-$C_4$ alkenyl, $C_3$-$C_4$ alkynyl, $CO_2$ $C_1$-$C_3$ alkyl, $CO_2$ allyl, $SO_2N(CH_3)_2$, $SO_2N(C_2H_5)_2$, $SO_2N(CH_3)C_2H_5$, $SO_2$ $C_1$-$C_3$ alkyl, $SO_2CF_3$; and $R_{13}$ and $R_{14}$ independently are hydrogen, $C_1$-$C_3$ alkyl, F, Cl, Br, $NO_2$, $C_1$-$C_3$ alkoxy, $CO_2$ $C_1$-$C_3$ alkyl, $CO_2$ allyl, $SC_1$-$C_3$ alkyl, SO $C_1$-$C_3$ alkyl, $SO_2$ $C_1$-$C_3$ alkyl, $SO_2N(CH_3)_2$, $SO_2N(CH_3)C_2H_5$, or $SO_2N(C_2H_5)_2$; provided that when either of $R_{13}$ or $R_{14}$ is $CO_2$ $C_1$-$C_3$ alkyl, $CO_2$ allyl, $SC_1$-$C_3$ alkyl, SO $C_1$-$C_3$ alkyl, $SO_2$ $C_1$-$C_3$ alkyl, $SO_2N(CH_3)_2$, $SO_2N(CH_3)C_2H_5$, $SO_2N(C_2H_5)_2$, then the other is hydrogen, Cl, CH$_3$, OCH$_3$ or NO$_2$, and agriculturally suitable salts thereof.

63. A herbicidal composition which comprises a pyrazole sulfonamide defined in claim 62 as an active ingredient.

64. A method for controlling the growth of undesired vegetation which comprises applying to the locus to be protected an effective amount of a compound of claim 62.

65. A compound represented by the formula

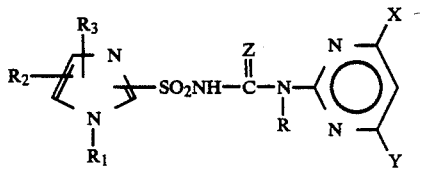

wherein
Z is O or S;
R is H or CH$_3$;
R$_1$ is H, C$_1$–C$_8$ alkyl, C$_3$–C$_6$ alkenyl, C$_5$–C$_6$ cycloalkyl, C$_5$–C$_6$ cycloalkenyl, C$_3$–C$_6$ alkynyl, C$_4$–C$_7$ cycloalkylalkyl, (R$_{17}$CH)$_m$C(O)C$_1$–C$_3$ alkyl, (R$_{17}$CH)$_n$CO$_2$R$_{18}$, (R$_{17}$CH)$_m$COSR$_{19}$, (R$_{17}$CH)$_n$CON(C$_1$–C$_2$ alkyl)$_2$, (R$_{17}$CH)$_n$SO$_2$R$_{22}$,

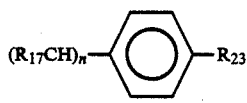

or C$_1$–C$_6$ alkyl substituted either with
(a) 1–3 atoms of F, Br or Cl; or
(b) O(C$_1$–C$_3$ alkyl);
R$_{17}$ is H or CH$_3$;
R$_{18}$ is C$_1$–C$_4$ alkyl, C$_3$–C$_4$ alkenyl, C$_3$–C$_4$ alkynyl, C$_3$–C$_4$ alkynyl, CH$_2$CH$_2$Cl or CH$_2$CH$_2$OCH$_3$;
R$_{19}$ is C$_1$–C$_4$ alkyl, C$_3$–C$_4$ alkenyl, C$_3$–C$_4$ alkynyl or CH$_2$CH$_2$OCH$_3$;
R$_{22}$ is CH$_3$, C$_2$H$_5$;
R$_{23}$ is H, Cl, Br, CH$_3$, F, CF$_3$, OCH$_3$ or NO$_2$;
R$_2$ is H or CH$_3$;
R$_3$ is H, C$_1$–C$_4$ alkyl, C$_3$–C$_4$ alkenyl, C$_3$–C$_4$ alkynyl, CO$_2$R$_{18}$, S(O)$_m$(C$_1$–C$_3$ alkyl), SO$_2$N(C$_1$–C$_2$ alkyl)$_2$, SO$_2$R$_{22}$ or C$_1$–C$_4$ alkyl substituted either with
(a) 1–3 atoms of F, Cl or Br, or
(b) OCH$_3$;
n is 0 or 1;
m is 0, 1 or 2;
X is CH$_3$, OCH$_3$, Cl, F, OCF$_2$H, SCF$_2$H;
Y is CH$_3$, C$_2$H$_5$, OCH$_3$, OC$_2$H$_5$, CH$_2$OCH$_3$, CH(OCH$_3$)$_2$, OCH$_2$F$_3$, OCF$_3$, NH$_2$, NH(CH)$_2$ or GCF$_2$T where G is O or S and T is H, CHClF, CHBrF, CF$_2$H or CHFCF$_3$; and agriculturally suitable salts thereof.

66. A herbicidal composition which comprises a imidazole sulfonamide defined in claim 65 as an active ingredient.

67. A method for controlling the growth of undesired vegetation which comprises applying to the locus to be protected an effective amount of a compound of claim 65.

68. A compound represented by the formula

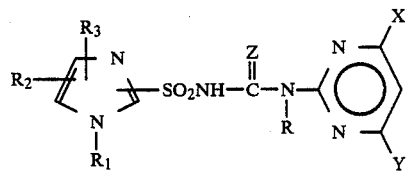

and agriculturally suitable salts thereof; wherein
Z is O;
R is H or CH$_3$;
R$_1$ is H, C$_1$–C$_8$ alkyl, C$_3$–C$_6$ alkenyl, C$_5$–C$_6$ cycloalkyl, C$_5$–C$_6$ cycloalkenyl, C$_3$–C$_6$ alkynyl, C$_4$–C$_7$ cycloalkylalkyl, (R$_{17}$CH)$_n$C(O)C$_1$–C$_3$ alkyl, (R$_{17}$CH)$_n$CO$_2$R$_{18}$, (R$_{17}$CH)$_n$COSR$_{19}$, (R$_{17}$CH)$_n$CONR$_{20}$R$_{21}$, (R$_{17}$CH)$_n$SO$_2$NR$_{20}$R$_{21}$, (R$_{17}$CH)$_n$SO$_2$R$_{22}$,

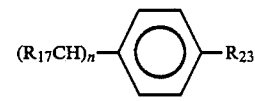

or C$_1$–C$_6$ alkyl substituted either with
(a) 1–3 atoms of F, Br or Cl; or
(b) O(C$_1$–C$_3$ alkyl); provided that (1) the total number of carbon atoms in R$_1$ are less than or equal to 8; and (2) when the sulfonylurea bridge is in the 2-position and
R$_1$ is other than C$_1$–C$_3$ alkyl, then R$_3$ must be H;
R$_{17}$ is H or CH$_3$;
R$_{18}$ is C$_1$–C$_4$ alkyl, C$_3$–C$_4$ alkenyl, C$_3$–C$_4$ alkynyl, CH$_2$CH$_2$Cl or CH$_2$CH$_2$OCH$_3$;
R$_{19}$ is C$_1$–C$_4$ alkyl, C$_3$–C$_4$ alkenyl, C$_3$–C$_4$ alkynyl or CH$_2$CH$_2$OCH$_3$;
R$_{20}$ and R$_{21}$ are independently CH$_3$ or C$_2$H$_5$;
R$_{22}$ is C$_1$–C$_3$ alkyl or CF$_3$;
R$_{23}$ is H, Cl, Br, CH$_3$, F, CF$_3$, OCH$_3$ or NO$_2$;
R$_{24}$ is C$_1$–C$_3$ alkyl or allyl;
R$_2$ is H or CH$_3$;
R$_3$ is H or CH$_3$, C$_1$–C$_4$ alkyl, OR$_6$, NO$_2$, F, Cl, Br, CO$_2$R$_{24}$, S(O)$_m$(C$_1$–C$_3$ alkyl) or SO$_2$NR$_{20}$R$_{21}$;
n is 0 or 1;
m is 0, 1 or 2;
X is CH$_3$, OCH$_3$, Cl, F, OCF$_2$H, SCF$_2$H;
Y is CH$_3$, C$_2$H$_5$, OCH$_3$, OC$_2$H$_5$, CH$_2$OCH$_3$, CH(OCH$_3$)$_2$, OCH$_2$F$_3$, OCF$_3$, NH$_2$, NHCH$_3$, N(CH$_3$)$_2$ or GCF$_2$T where G is O or S and T is H, CHClF, CHBrF, CF$_2$H or CHFCF$_3$; provided that
(1) when the sulfonylurea bridge is at the 2-position, then R$_3$ is H or CH$_3$;
(2) when the sulfonylurea bridge is at the 5-position, then R$_2$ is at the 2-position and R$_1$ is H, C$_1$–C$_4$ alkyl, C$_3$–C$_4$ alkenyl, C$_3$–C$_4$ alkynyl, CO$_2$R$_{18}$, SO$_2$NR$_{20}$R$_{21}$, SO$_2$R$_{22}$ or C$_1$–C$_4$ alkyl substituted with (a) 1–3 atoms of F, Cl or Br, or (b) OCH$_3$;
(3) when the sulfonylurea bridge is at the 4-position, then R$_2$ is at the 2-position, R$_1$ is CH$_3$ or C$_2$H$_5$, and R$_3$ is H, C$_1$–C$_4$ alkyl, OR$_{16}$, NO$_2$, F, Cl, Br, CO$_2$R$_{24}$, S(O)$_m$R$_{25}$ or SO$_2$NR$_{20}$R$_{21}$;
(4) when the sulfonylurea bridge is at the 5-position and R$_3$ is other than H, CH$_3$, OCH$_3$ or NO$_2$, then R$_1$ is H or CH$_3$; and
(5) when the sulfonylurea bridge is at the 5-position and R$_1$ is CO$_2$R$_{18}$, SO$_2$NR$_{20}$R$_{21}$ or SO$_2$R$_{22}$, then R$_3$ is H, CH$_3$, OCH$_3$ or NO$_2$.

(6) when X is Cl or F, then Y is OCH$_3$, NH$_2$, NHCH$_3$ or N(CH$_3$)$_2$.

69. A herbicidal composition which comprises an imidazine sulfonamide defined in claim 68 as an active ingredient.

70. A method for controlling the growth of undesired vegetation which comprises applying to the locus to be protected an effective amount of a compound of claim 68.

71. The compound of claim 18 where R$_{10}$ is CH$_3$, R$_{12}$ is H, R$_{11}$ is COOR$_{24}$, R$_{24}$ is C$_1$-C$_3$ alkyl, X is CH$_3$ or OCH$_3$, and Y is CH$_3$ or OCH$_3$.

72. A herbicidal composition which comprises a pyrazole sulfonamide defined in claim 71 as an active ingredient.

73. A method of controlling the growth of undesired vegetation which comprises applying to the locus to be protected an effective amount of a compound of claim 71.

74. The compound of claim 71 where R$_{24}$ is CH$_3$, X is CH$_3$ and Y is CH$_3$.

75. A herbicidal composition which comprises a pyrazole sulfonamide defined in claim 74 as an active ingredient.

76. A method of controlling the growth of undesired vegetation which comprises applying to the locus to be protected an effective amount of a compound of claim 74.

77. The compound of claim 71 where R$_{24}$ is —CH$_2$CH$_2$CH$_3$, X is OCH$_3$ and Y is OCH$_3$.

78. A herbicidal composition which comprises a pyrazole sulfonamide defined in claim 77 as an active ingredient.

79. A method of controlling the growth of undesired vegetation which comprises applying to the locus to be protected an effective amount of a compound of claim 77.

80. The compound of claim 71 where R$_{24}$ is —CH(CH$_3$)$_2$, X is CH$_3$ and Y is OCH$_3$.

81. A herbicidal composition which comprises a pyrazole sulfonamide defined in claim 80 as an active ingredient.

82. A method of controlling the growth of undesired vegetation which comprises applying to the locus to be protected an effective amount of a compound of claim 80.

* * * * *

UNITED STATES PATENT AND TRADEMARK OFFICE
CERTIFICATE OF CORRECTION

PATENT NO. : 4,931,081
DATED : June 5, 1990
INVENTOR(S) : Anthony D. Wolf

It is certified that error appears in the above-identified patent and that said Letters Patent is hereby corrected as shown below:

Claim 1, delete

"$Y_1$ is H Cl $CH_3$ $OCH_3$ or $OCF_2H$,
$X_2$ is $OCH_3$, $CH_3$, $CH_2CH_3$, $OCH_2CH_3$,
    $SCH_3$ or $SCH_2CH_3$;
$Y_2$ is $CH_3$, $CH_2CH_3$ or $CH_2CF_3$;
$X_3$ is $OCH_3$ or $CH_3$;"

Claim 2, delete

"A is

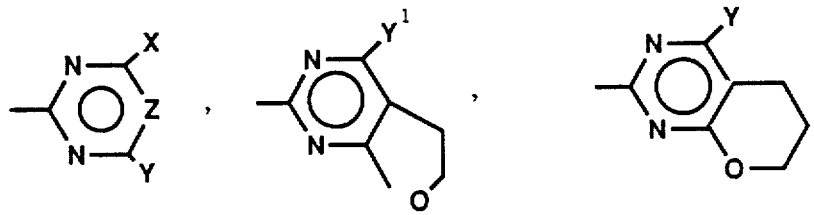

or 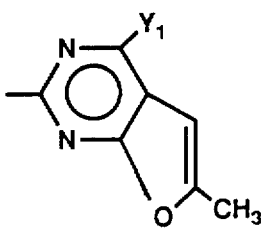 ;

"

UNITED STATES PATENT AND TRADEMARK OFFICE
CERTIFICATE OF CORRECTION

PATENT NO. : 4,931,081

DATED : June 5, 1990

INVENTOR(S) : Anthony D. Wolf

It is certified that error appears in the above-identified patent and that said Letters Patent is hereby corrected as shown below:

"Z is CH or N $Y_1$ is H, Cl, $CH_3$ or $OCH_3$ $X_2$ is $OCH_3$ or $CH_3$ and $Y_2$ is $CH_3$".

Claim 59, delete from the definition of Y the substituent "$OCF_2$".

Claim 61, after "59" delete -- / --.

Claim 62 and 65 delete from the definition of Y the substituent "$OCH_2F_3$" and substitute therefore -- $OCH_2CF_3$ --.

Claim 65, delete from the definition of $R_{18}$ the substituents "$C_3$-$C_4$ alkynyl", delete from the definition of Y the substituent "$NH(CH)_2$" and substitute therefore -- $NHCH_3$ --.

Signed and Sealed this

Fifteenth Day of October, 1991

Attest:

HARRY F. MANBECK, JR.

Attesting Officer

Commissioner of Patents and Trademarks